(12) United States Patent
Yamazoe et al.

(10) Patent No.: US 11,887,288 B2
(45) Date of Patent: Jan. 30, 2024

(54) IMAGE PROCESSING APPARATUS, IMAGE PROCESSING METHOD, AND STORAGE MEDIUM

(71) Applicant: CANON KABUSHIKI KAISHA, Tokyo (JP)

(72) Inventors: Manabu Yamazoe, Tokyo (JP); Yoshihiko Iwase, Kanagawa (JP); Riuma Takahashi, Tokyo (JP); Hiroki Uchida, Tokyo (JP); Ritsuya Tomita, Kanagawa (JP)

(73) Assignee: Canon Kabushiki Kaisha, Tokyo (JP)

( * ) Notice: Subject to any disclaimer, the term of this patent is extended or adjusted under 35 U.S.C. 154(b) by 165 days.

(21) Appl. No.: 17/468,297

(22) Filed: Sep. 7, 2021

(65) Prior Publication Data

US 2021/0398259 A1    Dec. 23, 2021

Related U.S. Application Data

(63) Continuation of application No. PCT/JP2019/044244, filed on Nov. 12, 2019.

(30) Foreign Application Priority Data

Mar. 11, 2019  (JP) .................. 2019-044263
Mar. 11, 2019  (JP) .................. 2019-044265
(Continued)

(51) Int. Cl.
  *G06T 5/50*     (2006.01)
  *G16H 30/40*    (2018.01)
  (Continued)

(52) U.S. Cl.
  CPC .............. *G06T 5/50* (2013.01); *G06N 20/00* (2019.01); *G06T 5/001* (2013.01); *G06T 11/60* (2013.01);
  (Continued)

(58) Field of Classification Search
  CPC . G06T 5/50; G06T 5/001; G06T 11/60; G06T 2207/10101; G06T 2207/20081;
  (Continued)

(56) References Cited

U.S. PATENT DOCUMENTS 10,660,514 B2   5/2020  Ohta
10,716,467 B2   7/2020  Uchida
(Continued)

FOREIGN PATENT DOCUMENTS

CN   102802505 A   11/2012
CN   104080400 A   10/2014
(Continued)

OTHER PUBLICATIONS

Kurihara, Satoshi et al.; Anomaly Detection of Fundus Image Using Image Completion; Electronic Committee Research Material; Sep. 27, 2018; ST 2018; pp. 105-109.
(Continued)

*Primary Examiner* — Jitesh Patel
(74) *Attorney, Agent, or Firm* — Canon U.S.A., Inc. IP Division

(57) ABSTRACT

An image processing apparatus includes display control means for displaying, on display means, a blend image obtained by performing blend processing at a variable transmissivity in accordance with an instruction of an operator using an optical coherence tomography (OCT) image and an OCT angiography (OCTA) image of mutually corresponding regions in a subject that are acquired by an OCT, setting means for setting a region of interest in the displayed blend image, and execution means for executing processing on the set region of interest in at least one image of the OCT image and the OCTA image.

20 Claims, 17 Drawing Sheets

(30) Foreign Application Priority Data

Mar. 29, 2019 (JP) ................................ 2019-068895
Oct. 3, 2019 (JP) ................................ 2019-183351

(51) Int. Cl.
- G06N 20/00 (2019.01)
- G06T 11/60 (2006.01)
- G06T 5/00 (2006.01)

(52) U.S. Cl.
CPC ... G16H 30/40 (2018.01); *G06T 2207/10101* (2013.01); *G06T 2207/20081* (2013.01); *G06T 2207/20221* (2013.01); *G06T 2210/41* (2013.01)

(58) Field of Classification Search
CPC ....... G06T 2207/20221; G06T 2210/41; G06T 2207/20084; G06T 2207/30041; G06T 2207/30101; G06T 5/002; G06T 5/007; G06T 7/0012; G06T 7/11; G06N 20/00; G06N 3/044; G06N 3/045; G06N 3/048; G06N 3/047; G06N 3/084; G16H 30/40; G16H 50/20

See application file for complete search history.

(56) References Cited

U.S. PATENT DOCUMENTS

| | | | |
|---|---|---|---|
| 11,026,570 B2 | 6/2021 | Machida | |
| 2009/0097728 A1 | 4/2009 | Lee et al. | |
| 2012/0050308 A1* | 3/2012 | Nakano | G06T 5/50 345/592 |
| 2014/0015856 A1* | 1/2014 | Xiao | G06T 11/00 345/629 |
| 2016/0063720 A1 | 3/2016 | Han | |
| 2018/0012359 A1 | 1/2018 | Prentasic et al. | |
| 2018/0018757 A1 | 1/2018 | Suzuki | |
| 2018/0144447 A1 | 5/2018 | Tate | |
| 2018/0153396 A1 | 6/2018 | Uchida | |
| 2018/0199807 A1 | 7/2018 | Ohta | |
| 2019/0000311 A1* | 1/2019 | Machida | A61B 3/1233 |
| 2019/0008482 A1* | 1/2019 | Kuroiwa | A61B 8/488 |

FOREIGN PATENT DOCUMENTS

| | | |
|---|---|---|
| CN | 104471389 A | 3/2015 |
| JP | H01170438 A | 7/1989 |
| JP | H1131214 A | 2/1999 |
| JP | 2001014444 A | 1/2001 |
| JP | 2008-119195 A | 5/2008 |
| JP | 2008119195 A | 5/2008 |
| JP | 2010-164351 A | 7/2010 |
| JP | 2011171843 A | 9/2011 |
| JP | 2011200635 A | 10/2011 |
| JP | 2012045298 A | 3/2012 |
| JP | 2014002497 A | 1/2014 |
| JP | 2015-129987 A | 7/2015 |
| JP | 2015-160105 A | 9/2015 |
| JP | 2016209147 A | 12/2016 |
| JP | 2017006179 A | 1/2017 |
| JP | 2017-047113 A | 3/2017 |
| JP | 2017-158962 A | 9/2017 |
| JP | 2017158687 A | 9/2017 |
| JP | 2017-189608 A | 10/2017 |
| JP | 2017189608 A | 10/2017 |
| JP | 2017-221555 A | 12/2017 |
| JP | 2018-5841 A | 1/2018 |
| JP | 2018007078 A | 1/2018 |
| JP | 2018084982 A | 5/2018 |
| JP | 2018-089301 A | 6/2018 |
| JP | 2018089160 A | 6/2018 |
| JP | 2018-114068 A | 7/2018 |
| JP | 2018-138159 A | 9/2018 |
| JP | 2018-153611 A | 10/2018 |
| JP | 2019025044 A | 2/2019 |
| WO | 2009107770 A1 | 9/2009 |
| WO | 2010050333 A1 | 5/2010 |
| WO | 2017030276 A1 | 2/2017 |
| WO | 2017/143300 A1 | 8/2017 |
| WO | WO-2017155015 A1 * | 9/2017 ........... A61B 3/0025 |

OTHER PUBLICATIONS

Akira Hasegawa; "Noise reduction processing by AI—PixelShine"; INNERVISION; Jun. 25, 2017; vol. 32, No. 7; pp. 31-34.

* cited by examiner

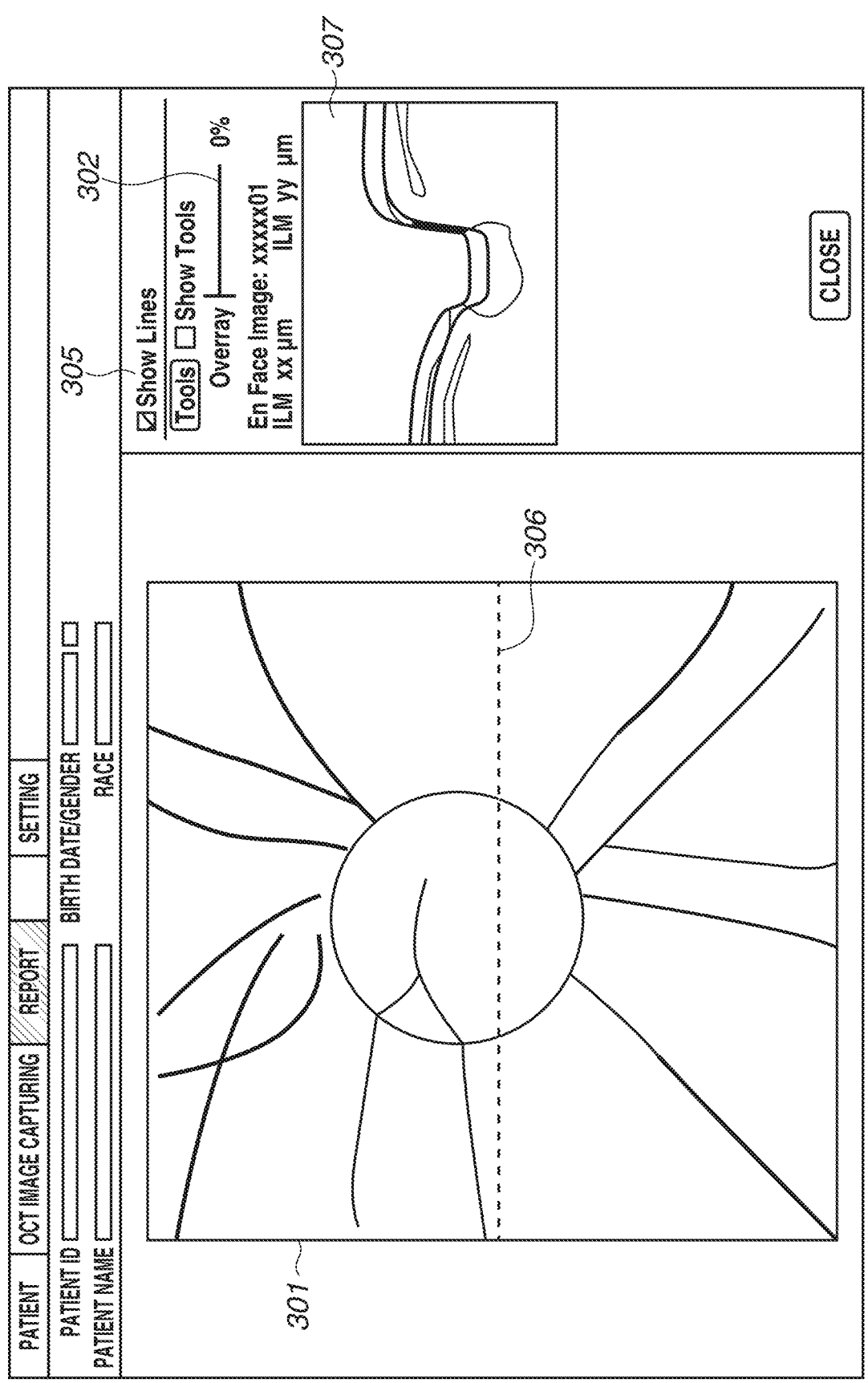

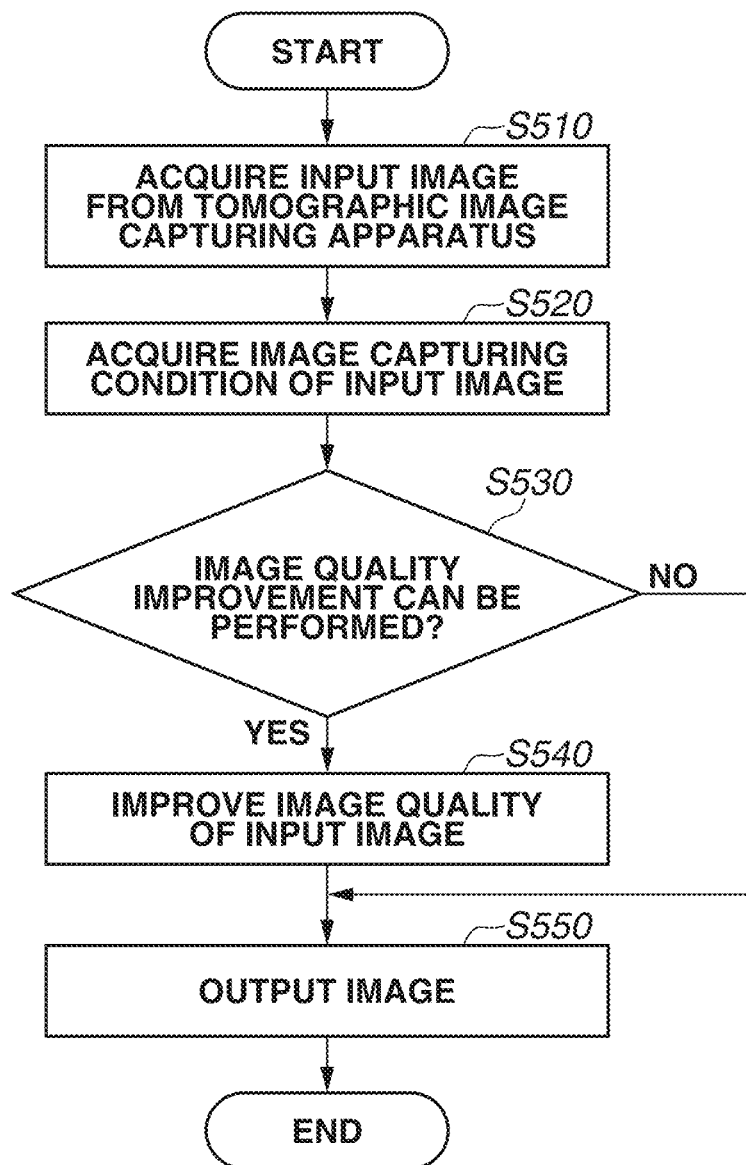

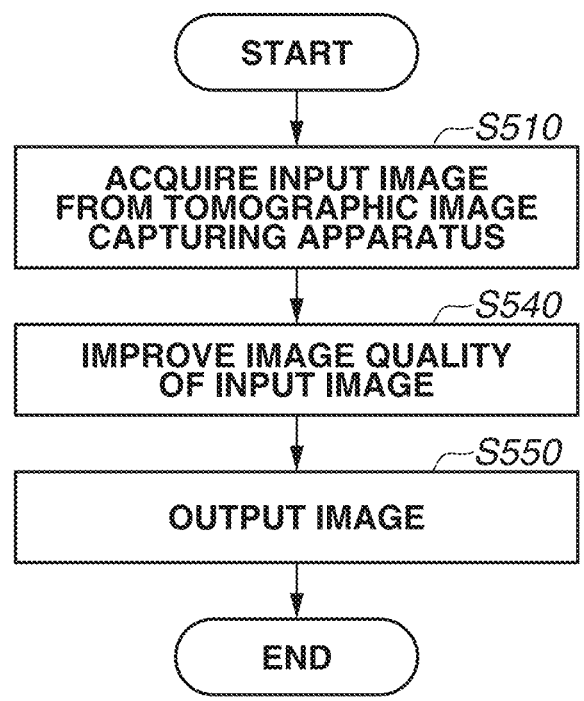

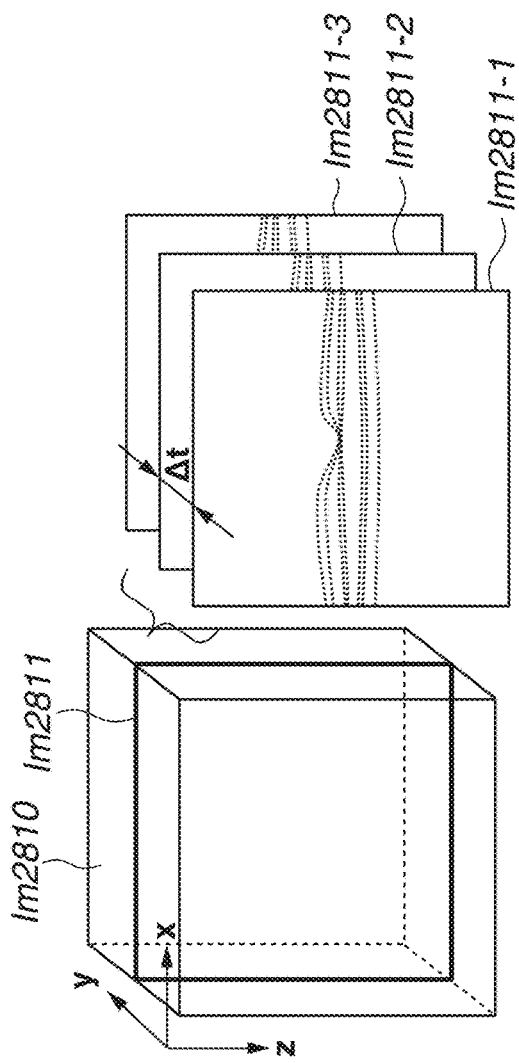
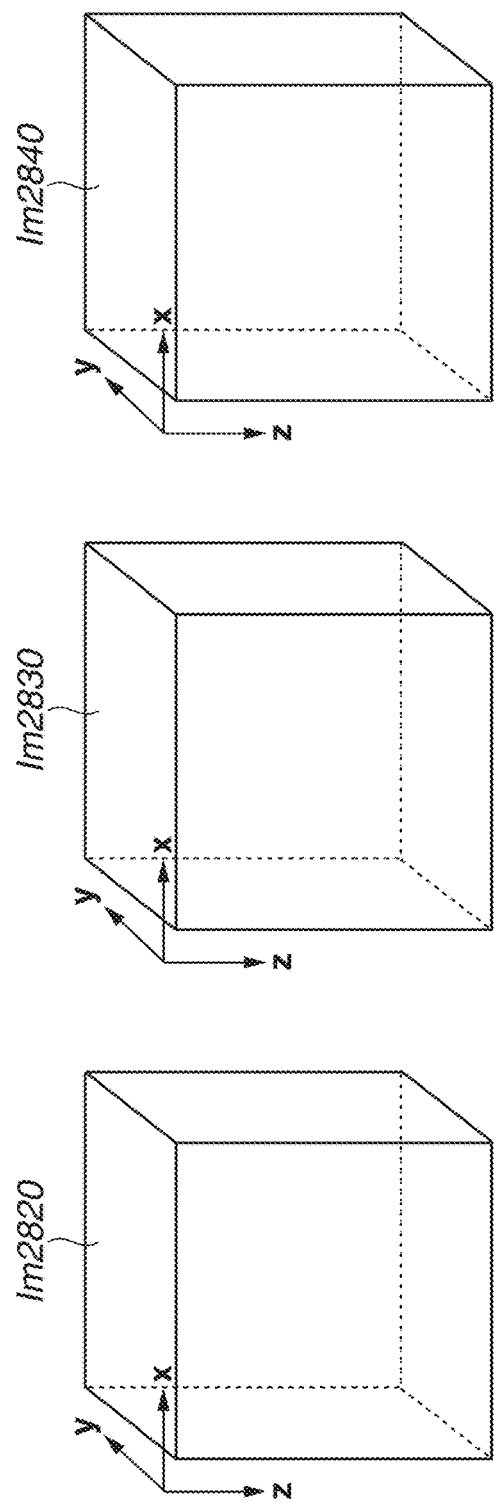
FIG.12A
FIG.12B

FIG.14A

IMAGE PROCESSING APPARATUS, IMAGE PROCESSING METHOD, AND STORAGE MEDIUM

CROSS-REFERENCE TO RELATED APPLICATIONS

This application is a Continuation of International Patent Application No. PCT/JP2019/044244, filed Nov. 12, 2019, which claims the benefit of Japanese Patent Application Nos. 2019-044263 and 2019-044265, filed on 11 Mar. 2019, Japanese Patent Application No. 2019-044263, filed Mar. 11, 2019, Japanese Patent Application No. 2019-068895, filed Mar. 29, 2019, and Japanese Patent Application No. 2019-183351, filed Oct. 3, 2019, all of which are hereby incorporated by reference herein in their entirety.

BACKGROUND OF THE INVENTION

Field of the Invention

The present invention relates to an image processing apparatus, an image processing method, and a storage medium that perform processing on a tomographic image of a subject that is acquired by an optical coherence tomography (OCT).

Background Art

A medical tomographic image capturing apparatus, such as an optical coherence tomography (OCT), can three-dimensionally observe a state of the inside of a retinal layer, and is useful in the diagnosis of ophthalmic retinal disease, such as age-related macular degeneration (AMD). In recent years, methods for acquiring images at high speed by OCTs used in clinical sites are broadly divided into two methods: a spectral domain OCT (SD-OCT) that acquires an interferogram with a spectroscope using a broadband light source, and a swept source OCT (SS-OCT) that uses a method of measuring spectral interference with a single-channel light detector by using a high-speed wavelength swept light source as a light source. In recent OCTs of both methods, an OCT angiography (OCTA) for imaging blood vessels without using contrast agent has attracted attention. The OCTA generates motion contrast data from an OCT image acquired by an OCT. The motion contrast data is data indicating a temporal change in measurement target that is detected by repeatedly capturing images of the same cross-section of the measurement target using an OCT. The motion contrast data is calculated from a difference, a ratio, or correlation of temporal changes in a phase, a vector, and an intensity of a complex OCT signal.

In general, it is becoming customary to display an OCTA image as an OCTA front image converted into a two-dimensional image by projecting three-dimensional motion contrast data calculated from an acquired three-dimensional OCT image, onto a two-dimensional plane. PTL1 discusses a technique of generating a two-dimensional front image by designating a range in a depth direction of motion contrast data to be projected for displaying an OCTA image.

CITATION LIST

Patent Literature

PTL1: Japanese Patent Application Laid-Open No. 2017-6179

SUMMARY OF THE INVENTION

Nevertheless, analysis processing of OCT data or motion contrast data can bear improvements in various aspects. For example, it has been sometimes difficult to make an appropriate setting only by using front images when a region of interest serving as a target of analysis processing of OCT data or motion contrast data is set.

The present invention has been devised in view of the above-described issues, and one of the objects is to make a region of interest serving as a target of analysis processing, desirably settable.

An image processing apparatus according to an aspect of the present invention includes display control means for displaying, on display means, a blend image obtained by performing blend processing at a variable transmissivity in accordance with an instruction of an operator using an optical coherence tomography (OCT) image and an OCT angiography (OCTA) image of mutually corresponding regions in a subject that are acquired by an OCT, setting means for setting a region of interest in the displayed blend image, and execution means for executing analysis or processing on the set region of interest in at least one image of the OCT image and the OCTA image.

Further features of the present invention will become apparent from the following description of exemplary embodiments with reference to the attached drawings.

BRIEF DESCRIPTION OF THE DRAWINGS

FIG. 3A is a diagram illustrating a display screen displaying a front image of an optive nerve head, and a display screen displaying a blend image obtained by transmission processing.

FIG. 7 is a flowchart illustrating an example of an image processing flow according to the fourth exemplary embodiment.

FIG. 8 is a flowchart illustrating another example of an image processing flow according to the fourth exemplary embodiment.

FIG. 12A illustrates an example of a teaching image related to image quality improvement processing. FIG. 12B illustrates an example of a teaching image related to image quality improvement processing.

FIG. 14A illustrates an example of a user interface according to the fifth exemplary embodiment.

DESCRIPTION OF THE EMBODIMENTS

First Exemplary Embodiment

The description will be given of a case where an image processing apparatus according to the present exemplary embodiment performs analysis processing while setting an analysis position and an analysis region with reference to a front image of OCT data for analysis of the OCTA data. Hereinafter, an image processing system having an image processing apparatus according to a first exemplary embodiment of the present invention will be described with reference to the drawings.

(Configuration of Image Processing Apparatus)

Figure 1:
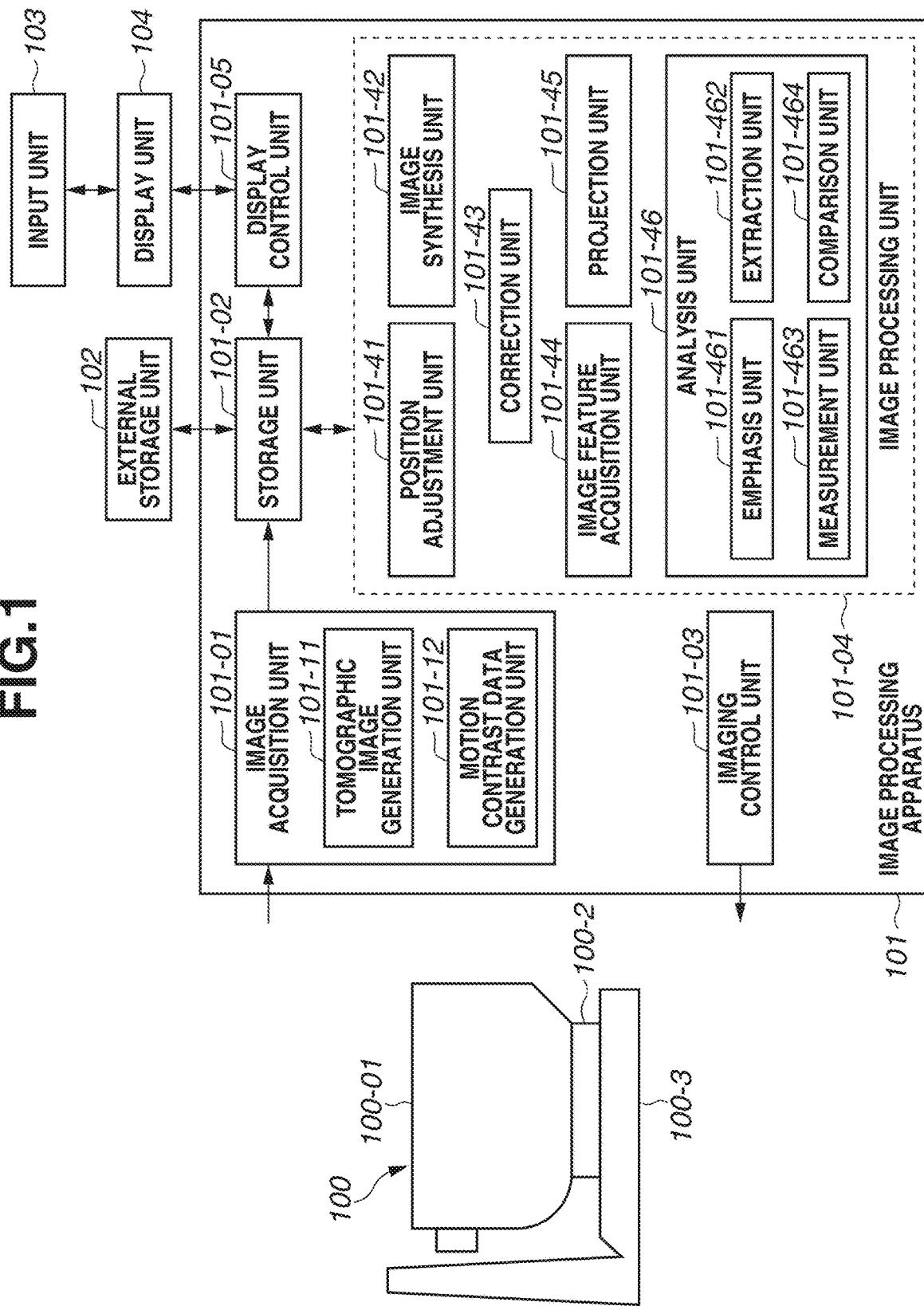
FIG. 1 is a block diagram illustrating a configuration of an image processing apparatus according to a first exemplary embodiment.

A configuration of an image processing apparatus 101 of the present exemplary embodiment and connection with another device will be described with reference to FIG. 1. The image processing apparatus 101 is a personal computer (PC) connected to a tomographic image capturing apparatus 100. Functions included in functional blocks corresponding to an image acquisition unit 101-01, an imaging control unit 101-03, an image processing unit 101-04, and a display control unit 101-05 are implemented by a calculation processing apparatus central processing unit (CPU) (not illustrated) executing software modules stored in a storage unit 101-02. It should be appreciated that the present invention is not limited to such a PC configuration. For example, the image processing unit 101-04 may be implemented by dedicated hardware, such as an application specific integrated circuit (ASIC), and the display control unit 101-05 may be implemented by using a dedicated processor, such as a graphics processing unit (GPU) that is different from a CPU. Furthermore, the tomographic image capturing apparatus 100 and the image processing apparatus 101 may be connected via a network, or an external storage unit 102 may also be placed on the network such that data can be shared by a plurality of image processing apparatuses.

The image acquisition unit 101-01 is a functional block that acquires signal data of a scanning laser ophthalmoscope (SLO) fundus image or a tomographic image obtained by capturing an image of a subject using the tomographic image capturing apparatus 100 to generate an image. The image acquisition unit 101-01 includes a tomographic image generation unit 101-11 and a motion contrast data generation unit 101-12. The tomographic image generation unit 101-11 acquires signal data (interference signal) of a tomographic image captured by the tomographic image capturing apparatus 100 to generate a tomographic image by performing signal processing, and stores the generated tomographic image into the storage unit 101-02. The motion contrast data generation unit 101-12 generates motion contrast data based on a plurality of tomographic images of the same region (regions in a subject that correspond to each other) that have been generated by the tomographic image generation unit 101-11.

First of all, the tomographic image generation unit 101-11 generates a tomographic image for one cluster, by performing frequency conversion, fast Fourier Transform (FFT), and absolute value conversion (acquisition of amplitude) on an interference signal acquired by the image acquisition unit 101-01.

Next, the position adjustment unit 101-41 aligns positions of tomographic images belonging to the same cluster, and performs overlay processing. An image feature acquisition unit 101-44 acquires layer boundary data from the overlaid tomographic images. In the present exemplary embodiment, a variable shape model is used as an acquisition method of a layer boundary, but any known layer boundary acquisition method may be used. Here, acquisition processing of a layer boundary is not essential. For example, in a case where a motion contrast image is to be generated only in three-dimension and a two-dimensional motion contrast image projected in a depth direction is not to be generated, acquisition processing of a layer boundary can be omitted. The motion contrast data generation unit 101-12 calculates a motion contrast between neighboring tomographic images in the same cluster. In the present exemplary embodiment, the motion contrast data generation unit 101-12 obtains a decorrelation value Mxy as a motion contrast based on the following formula (1), $$Mxy = 1 - 2 \times \frac{Axy \times Bxy}{Axy^2 + Bxy^2}, \tag{1}$$

In the formula (1), Axy denotes an amplitude at a position (x, y) of tomographic image data A (of complex number data having subjected to FFT processing), and Bxy denotes an amplitude at the same position of tomographic data B as the position (x, y). A relation of $0 \leq Mxy \leq 1$ is satisfied, and as a difference between the both amplitude values of Axy and Bxy becomes larger, a value of Mxy becomes closer to 1. An image having, as pixel values, averages of motion contrast values obtained by performing decorrelation calculation processing as represented by Formula (1) between arbitrary neighboring tomographic images (belonging to the same cluster) is generated as a final motion contrast image. The number of the obtained motion contrast values is obtained by subtracting one from the number of tomographic images per cluster.

In this example, a motion contrast is calculated based on an amplitude of complex number data having been subjected to FFT processing, but a calculation method of a motion contrast is not limited to the above-described method. For example, a motion contrast may be calculated based on phase information of complex number data, or may be calculated based on information regarding both an amplitude and a phase. Alternatively, a motion contrast may be calculated based on a real part and an imaginary part of complex number data.

In addition, in the present exemplary embodiment, a decorrelation value is calculated as a motion contrast, but the calculation method of a motion contrast is not limited thereto. For example, a motion contrast may be calculated based on a difference between two values, or a motion contrast may be calculated based on a ratio between the two values.

Furthermore, in the above description, a final motion contrast image is acquired by obtaining an average value of a plurality of acquired decorrelation values. However, the present invention is not limited to this. For example, an image having, as a pixel value, a median value or the maximum value of a plurality of acquired decorrelation values may be generated as a final motion contrast image.

The imaging control unit 101-03 is a functional block that performs imaging control of the tomographic image capturing apparatus 100. The imaging control includes designating a setting of an image capturing parameter for the tomographic image capturing apparatus 100, and issuing a start or end instruction of image capturing. The image processing unit 101-04 is a functional block including the position adjustment unit 101-41, a synthesis unit 101-42, a correction unit 101-43, the image feature acquisition unit 101-44, a projection unit 101-45, and an analysis unit 101-46. The synthesis unit 101-42 includes, for example, a synthesis method designation unit, a same modality image synthesis unit, and different types of modality image synthesis units. The synthesis unit 101-42 synthesizes a plurality of two-dimensional images into one image. Specifically, the synthesis method designation unit designates types of synthesis target images (tomographic images, motion contrast images, or a tomographic image and a motion contrast image), and a synthesis processing method (overlay, combining. or juxtaposed display). The same modality image synthesis unit performs synthesis processing between tomographic images or motion contrast images. The plural modality image synthesis unit performs synthesis processing between a tomographic image and a motion contrast image. The synthesis unit 101-42 is an example of an image quality improvement means that improves the image quality of motion contrast data. Also in the present exemplary embodiment, for example, image quality improvement processing to be performed using machine learning in a fourth exemplary embodiment to be described below can be applied as processing to be performed by the image quality improvement means, aside from processing to be performed by the synthesis unit 101-42. The correction unit 101-43 performs processing of suppressing projection artifact generated in a motion contrast image. The projection artifact is a phenomenon in which a motion contrast in retina surface layer blood vessels is shown on a deep layer side (retina deep layer or retina outer layer/choroid), and a high decorrelation value is obtained in a region on the deep layer side where blood vessels do not exist. For example, the correction unit 101-43 performs processing of reducing projection artifact in synthesized motion contrast data. In other words, the correction unit 101-43 is an example of a processing unit that performs processing of reducing projection artifact on synthesized motion contrast data. The projection unit 101-45 projects a tomographic image or motion contrast image in a depth range that is based on a boundary position acquired by the image feature acquisition unit 101-44, and generates a brightness front image (brightness tomographic image) or a motion contrast front image. At this time, projection may be performed in any depth range. In the present exemplary embodiment, however, two types of front synthesis motion contrast images are generated in a depth range of the retina surface layer and the retina outer layer. As the projection method, either one of maximum intensity projection (MIP) and average intensity projection (AIP) can be selected. A projection range for generating a motion contrast front image can be changed by an operator selecting a depth range from a predetermined depth range set displayed on a selection list (not illustrated). Alternatively, the projection range can be changed by changing a type and an offset position of a layer boundary to be used for designation of a projection range, from a user interface, or by operating moving layer boundary data overlaid on a tomographic image, from an input unit 103. A motion contrast image to be displayed on a display unit 104 is not limited to a motion contrast front image, and a three-dimensionally rendered three-dimensional motion contrast image may be displayed. Furthermore, above-described projection method or whether to perform projection artifact suppression processing may be changed from a user interface, such as a context menu. For example, a motion contrast image having been subjected to projection artifact suppression processing may be displayed on the display unit 104 as a three-dimensional image. The analysis unit 101-46 is a functional block including an emphasis unit 101-461, an extraction unit 101-462, a measurement unit 101-463, and a comparison unit 101-464. The extraction unit 101-462 acquires, from a tomographic image, layer boundaries of retina and choroid, boundaries of the front surface and the back surface of a cribriform plate, and positions of a central fovea and an optive nerve head center. The extraction unit 101-462 extracts a blood vessel region from a motion contrast front image. The measurement unit 101-463 calculates a measured value, such as a blood vessel density, using the extracted blood vessel region and blood vessel center line data acquired by thinning the blood vessel region.

The image processing apparatus 101 is connected with the tomographic image capturing apparatus 100, the external storage unit 102, the input unit 103, and the display unit 104 via an interface. The image processing apparatus 101 performs control of a stage unit 100-2 and control of an alignment operation. The external storage unit 102 stores, in association, programs for tomographic image capturing, information regarding a subject's eye (name, age, gender, etc. of a patient), captured images (tomographic image and SLO image/OCTA image) and synthetic images, image capturing parameters, image data and measurement data of past inspections, and parameters set by an operator.

The input unit 103 is, for example, a mouse, a keyboard, or a touch operation screen for issuing an instruction to a computer, and an operator issues instructions to the image processing apparatus 101 and the tomographic image capturing apparatus 100 via the input unit 103. The display unit 104 is, for example, a monitor, and may be provided with a touch user interface (UI).

(Configuration of Tomographic Image Capturing Apparatus)

The tomographic image capturing apparatus 100 is an apparatus for capturing a tomographic image of an eye. Configurations of a measurement optical system and a spectroscope of the tomographic image capturing apparatus 100 according to the present exemplary embodiment will be described with reference to FIG. 2.

In the present exemplary embodiment, a spectral domain OCT (SD-OCT) is used as the tomographic image capturing apparatus 100. The tomographic image capturing apparatus 100 is not limited to this. For example, a swept source OCT (SS-OCT) may be used.

The measurement optical system 100-1 is an optical system for acquiring an anterior eye segment image, an SLO fundus image, and a tomographic image of a subject's eye. The stage unit 100-2 makes the measurement optical system 100-1 movable forward and backward, and leftward and rightward. A base unit 100-3 incorporates a spectroscope described below.

Figure 2:
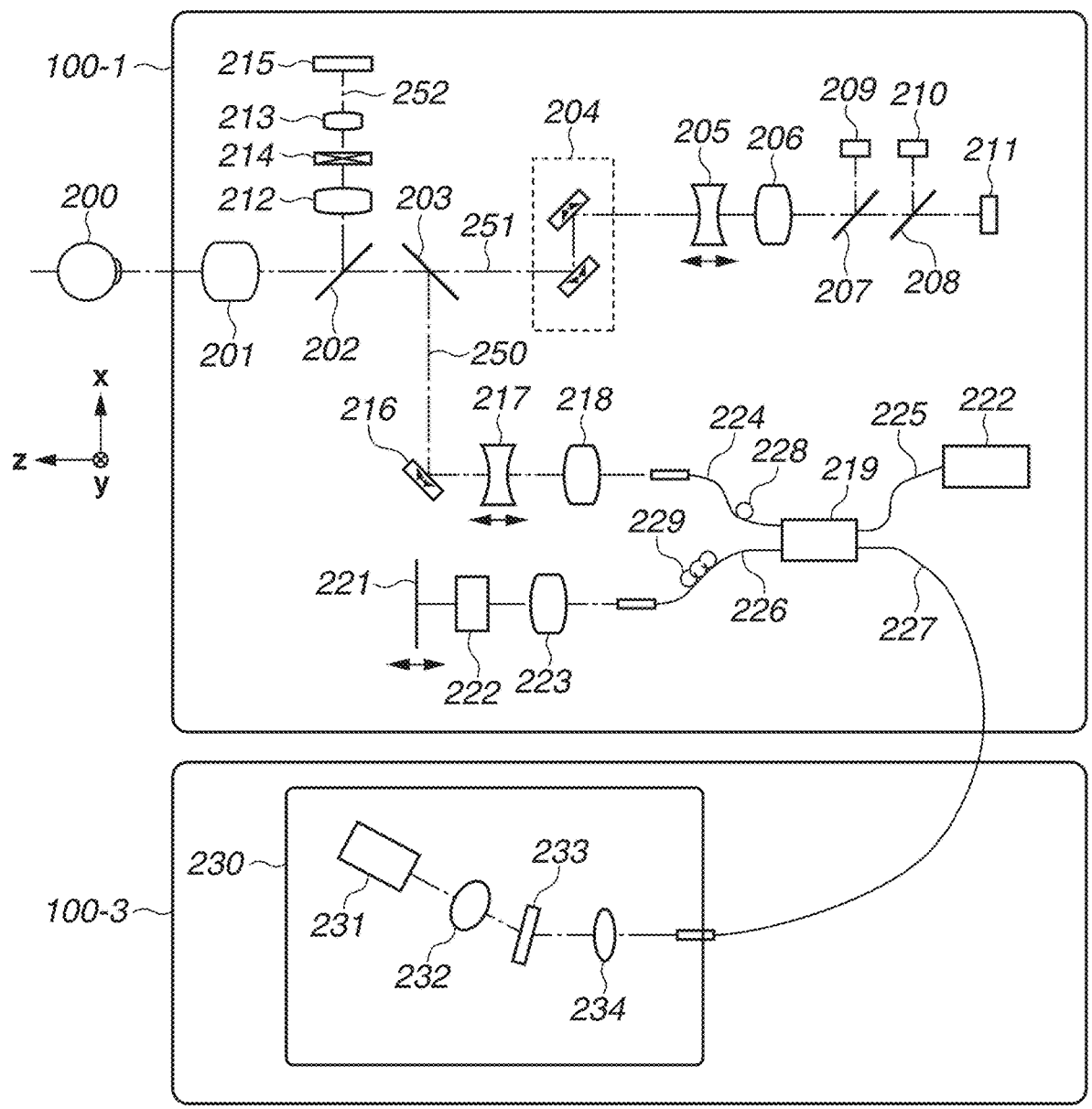
FIG. 2 is a diagram illustrating a tomographic image capturing apparatus according to the first exemplary embodiment.

The inside of the measurement optical system 100-1 will now be described. An objective lens 201 is installed to face the subject's eye 200, and a first dichroic mirror 202 and a second dichroic mirror 203 are arranged on an optical axis of the objective lens 201. These dichroic mirrors separate an optical path for each wavelength band into an optical path 250 for an OCT optical system, an optical path 251 for an SLO optical system and a fixation lamp, and an optical path 252 for anterior eye observation. The optical path 251 for an SLO optical system and a fixation lamp includes an SLO scanning unit 204, lenses 205 and 206, a mirror 207, a third dichroic mirror 208, an avalanche photodiode (APD) 209, an SLO light source 210, and a fixation lamp 211. The mirror 207 is a prism obtained by evaporating a perforated mirror or a hollow mirror, and separates light into illumination light emitted by the SLO light source 210 and return light from the subject's eye. The third dichroic mirror 208 separates an optical path by wavelength band into an optical path of the SLO light source 210 and an optical path of the fixation lamp 211. The SLO scanning unit 204 scans the subject's eye 200 with light emitted from the SLO light source 210, and includes an X scanner for scanning in an X direction and a Y scanner for scanning in a Y direction. In the present exemplary embodiment, the X scanner includes a polygonal mirror to perform high-speed scanning, and the Y scanner includes a galvano mirror. The lens 205 is driven by a motor (not illustrated), for focusing of the SLO optical system and the fixation lamp 211. The SLO light source 210 emits light having a wavelength in the vicinity of 780 nm. The APD 209 detects return light from the subject's eye. The fixation lamp 211 emits visible light and prompt visual fixation of a subject. Light emitted from the SLO light source 210 is reflected on the third dichroic mirror 208, passes through the mirror 207, passes through the lenses 206 and 205, and is used to scan the subject's eye 200 by the SLO scanning unit 204. After returning through the same route as illumination light, return light from the subject's eye 200 is reflected by the mirror 207, guided to the APD 209, and an SLO fundus image is obtained. Light emitted from the fixation lamp 211 passes through the third dichroic mirror 208 and the mirror 207, passes through the lenses 206 and 205, forms a predetermined shape at an arbitrary position on the subject's eye 200 using the SLO scanning unit 204, and prompts a visual fixation of the subject. On the optical path 252 for anterior eye observation, lenses 212 and 213, a split prism 214, and a charge-coupled device (CCD) 215 for anterior eye segment observation that detects infrared light are arranged. The CCD 215 has sensitivity to light in a wavelength of light (not illustrated) emitted for anterior eye segment observation. Specifically, the CCD 215 has sensitivity to light in a wavelength in the vicinity of 970 nm. The split prism 214 is arranged at a position conjugated with a pupil of the subject's eye 200, and the split prism 214 can detect a distance in a Z-axis direction (optical axis direction) of the measurement optical system 100-1 with respect to the subject's eye 200, as a split image of an anterior eye segment. As described above, the optical path 250 of an OCT optical system includes an OCT optical system, and the optical path 250 is provided for capturing a tomographic image of the subject's eye 200. More specifically, the optical path 250 is provided for acquiring an interference signal for forming a tomographic image. An XY scanner 216 is provided for scanning the subject's eye 200 with light. FIG. 2 illustrates the XY scanner 216 having one mirror. However, the XY scanner 216 is a galvano mirror that performs scanning in XY two directions. A lens 217 out of lenses 217 and 218 is driven by a motor (not illustrated), for focusing light from an OCT light source 220 that is emitted from a fiber 224 connected to an optical coupler 219, on the subject's eye 200. By the focusing, return light from the subject's eye 200 enters the fiber 224 while simultaneously forming an image at a leading end of the fiber 224 in a spot shape. An optical path from the OCT light source 220, and configurations of a reference optical system and a spectroscope will now be described. The optical path includes the OCT light source 220, a reference mirror 221, a dispersion compensation glass 222, a lens 223, an optical coupler 219, single-mode optical fibers 224 to 227 integrally connected to an optical coupler, and a spectroscope 230. These components constitute a Michelson interferometer. Light emitted from the OCT light source 220 passes through the optical fiber 225, and are separated via the optical coupler 219 into measurement light on the optical fiber 224 side and reference light on the optical fiber 226 side. The measurement light is emitted onto the subject's eye 200 serving as an observation target, through the above-described OCT optical system optical path, and reaches the optical coupler 219 through the same optical path by reflection and scattering caused by the subject's eye 200. In contrast, the reference light reaches the reference mirror 221 via the optical fiber 226, the lens 223, and the dispersion compensation glass 222 inserted for compensation for wavelength dispersion of measurement light and reference light, and is reflected. Then, the reference light returns through the same optical path and reaches the optical coupler 219. The measurement light and the reference light are combined by the optical coupler 219 to become interfering light. Interference occurs when an optical path length of the measurement light and an optical path length of the reference light become approximately the same. The reference mirror 221 is held to be adjustable in an optical axis direction by a motor and a drive mechanism (not illustrated), and the optical path length of the reference light can be made consistent with the optical path length of the measurement light. The interfering light is guided to the spectroscope 230 via the optical fiber 227. In addition, polarization adjustment units 228 and 229 are respectively provided in the optical fibers 224 and 226, and perform polarization adjustment. These polarization adjustment units include several looped portions of optical fibers. By rotating the looped portions about a longer direction of the fibers, the fibers are twisted, and polarization states of the measurement light and the reference light can be individually adjusted and synchronized. The spectroscope 230 includes lenses 232 and 234, a diffraction grating 233, and a line sensor 231.

The interfering light emitted from the optical fiber 227 becomes parallel light via the lens 234, and then, the parallel light is dispersed by the diffraction grating 233, and formed on the line sensor 231 by the lens 232. Next, the periphery of the OCT light source 220 will be described. The OCT light source 220 is a super luminescent diode (SLD), which is a typical low coherent light source. The center wavelength of the OCT light source 220 is 855 nm, and the wavelength bandwidth is about 100 nm. The bandwidth affects resolution in an optical axis direction of a tomographic image to be obtained, the bandwidth is therefore an important parameter. In this example, the SLD is selected as a type of the light source, but the light source is only required to be capable of emitting low coherent light, and amplified spontaneous emission (ASE) can be used. In consideration of measurement of an eye, near-infrared light is suitable for the center wavelength. The center wavelength also affects resolution in a traverse direction of a tomographic image to be obtained, it is thus desirable that the center wavelength is as short as possible. For both reasons, the center wavelength is set to 855 nm. In the present exemplary embodiment, the Michelson interferometer is used as the interferometer, but a Mach-Zehnder interferometer may be used. In accordance with a light amount difference between the measurement light and the reference light, the Mach-Zehnder interferometer is desirably used in a case where the light amount difference is large, and the Michelson interferometer is desirably used in a case where the light amount difference is relatively small.

(Analysis Processing of OCTA Data)

Hereinafter, analysis processing targeting OCT motion contrast data will be specifically described. Terms to be used in the description of the exemplary embodiment will be briefly defined. First of all, information regarding three-dimensional volume data will be described as OCT data or OCTA data. Next, two-dimensional information that can be extracted from volume data will be described as an OCT image or an OCTA image. In particular, an image created by projecting volume data in a designated range in the depth direction will be described as an OCT front image or an OCTA front image. In addition, two-dimensional information including data in the depth direction will be described as a tomographic image.

FIG. 3A illustrates an OCTA front image 301 of an optive nerve head (ONH). A slide bar 302 indicates a transmissivity of 0% as a default value, which is a transmissivity of an OCT front image described below. In this example, as the transmissivity indicated by the slide bar 302, a lastly-set transmissivity may be stored, or a transmissivity may be returned to a default value of 0% when the OCTA front image is switched to another OCTA front image.

It is known that a vascular function of an ONH is closely related to the progress status of glaucoma, and it is said that quantitatively analyzing a vascular dysfunction has a large clinical value. Nevertheless, it is a bit difficult to set a boundary of a neural canal opening (NCO) on an OCTA front image. Because the visibility of the NCO is enhanced in an OCT front image, it becomes easier to set an analysis region. For evaluating a role of an ONH circulatory failure in glaucoma, it becomes important to acquire reliable information for microcirculation.

Figure 3B:
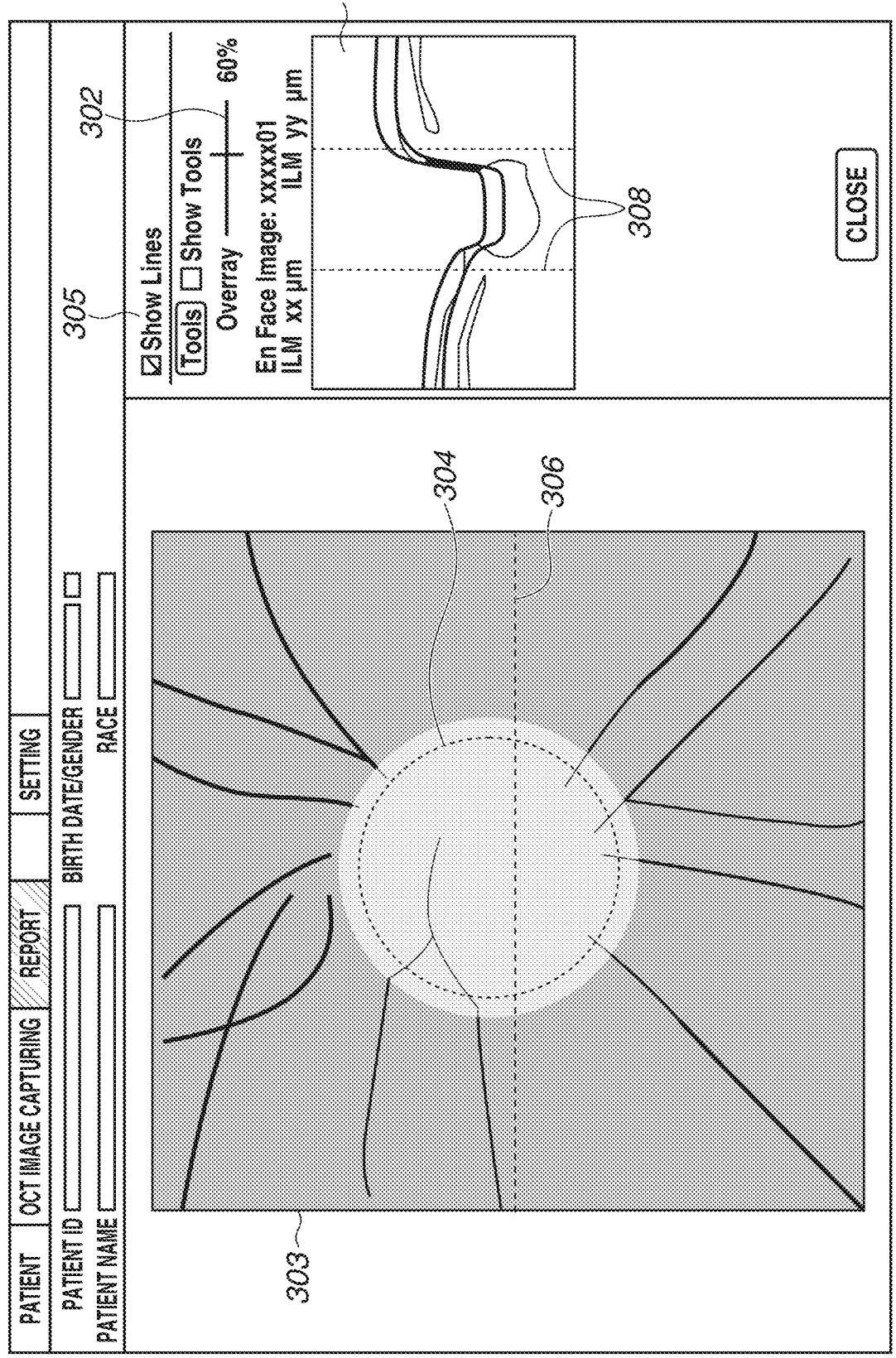
FIG. 3B is a diagram illustrating a display screen displaying a front image of an optive nerve head, and a display screen displaying a blend image obtained by transmission processing.
Figure 4:
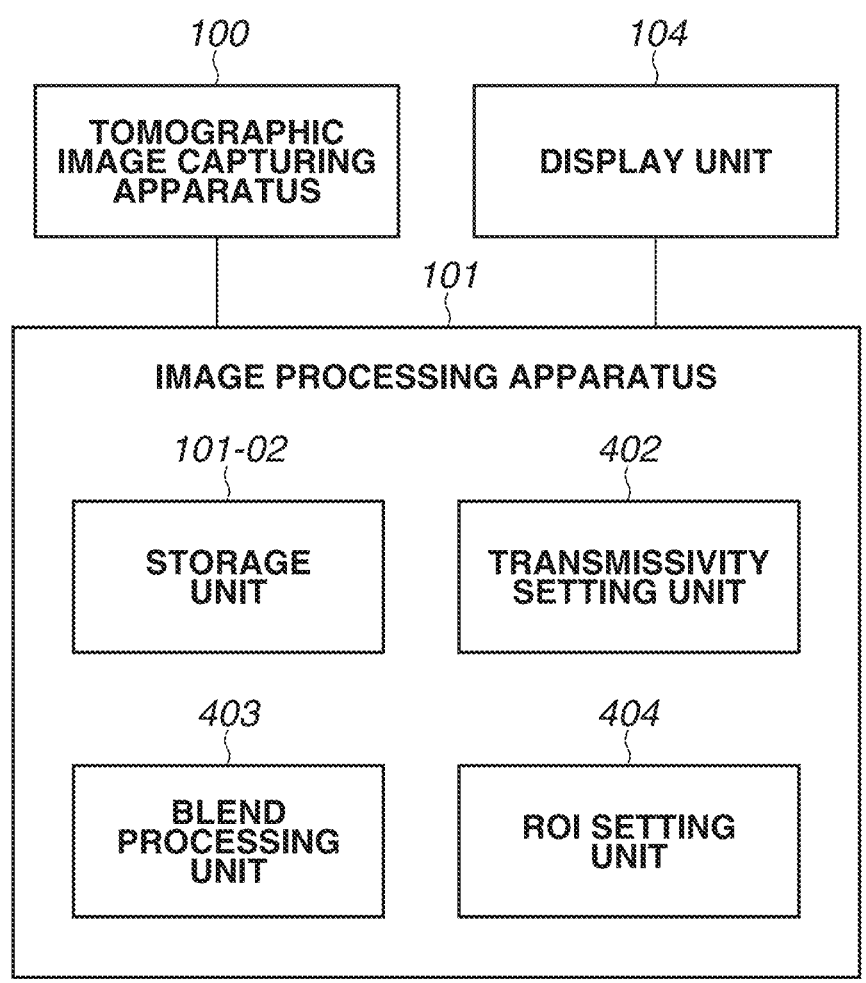
FIG. 4 is a block diagram illustrating a configuration of an image processing apparatus according to the first exemplary embodiment.

FIG. 3B illustrates an example case where an operator sets the slide bar 302 to 60%. An image 303 generated based on a set transmissivity is displayed using an OCTA front image and a second OCT front image that is different from the OCTA front image. In other words, a blend image having been subjected to blend processing based on a variable transmissivity is generated using an OCT image and an OCT image of the same point of a subject that have been acquired by the optical coherence tomography. Analysis processing is then executed on a set analysis region 304. Specifically, the image processing system of the image processing apparatus 101 of the present exemplary embodiment will be described with reference to FIGS. 1 and 4. First of all, when an operator designates an OCTA front image in a designated range in the depth direction as a target image, an OCTA front image and an OCT front image serving as a second medical image that are stored in the storage unit 101-02 are acquired. The OCTA front image, the OCT front image, and the range in the depth direction need not always coincide with each other. An operator can also designate different ranges in the depth direction. In the transmissivity setting unit 402, an operator sets a transmissivity based on a position set by the slide bar 302, and determines a transmission coefficient α

(0≤α≤1) for a second medical image (in this example, OCT front image). At this time, transmission processing performs weighted average of two images for each pixel using typical alpha blend processing. The blend processing is executed by performing, for example, weighted average processing of pixel values of mutually corresponding positions of an OCT image and an OCTA image.

$$(\text{transparent image}) = (\text{first medical image}) \times (1-\alpha) + (\text{second medical image}) \times \alpha \qquad (2)$$

A blend processing unit 403 generates a blend image (hereinafter, described as a transparent image) that is based on the above-described formula (2), and the display control unit 101-05 displays the generated blend image on the display unit 104. While checking the transparent image displayed on the display unit 104, the operator may change a transmissivity until the transparent image becomes a desired transparent image. Alternatively, the operator may change a range in the depth direction of the image while checking a visibility.

Next, an ROI setting unit 404 sets a region of interest (ROI) to be analyzed on the transparent image. ROI information may be set as parameters, such as a center position and a size, or may be set as a general shape (e.g., circle, ellipse, or rectangle). Alternatively, ROI information may be set as a region having a spline curve formed by a plurality of control points, as a free region. It is sufficient that ROI information is displayed with being superimposed on a transparent image. Furthermore, to check whether a set ROI is a desired region, the operator can update a transparent image by changing a transmissivity in a state in which ROI information is displayed in a superimposed manner. In this manner, it is possible to adjust a state of microcirculation or the visibility of an NCO boundary by appropriately changing the transmissivity of the OCT front image.

Lastly, the analysis unit 101-46, which is an example of an execution unit that executes processing on a region of interest in an image, executes various types of image analysis. The type of analysis may be designated by an operator, or may be preset analysis. The extraction unit 101-462 extracts a feature amount of an image suitable for the type of analysis, and the measurement unit 101-463 performs various types of measurement. An analysis result is displayed on the display unit 104. The operator designates, for example, blood vessel extraction processing that is based on the set ROI information. The extraction unit 101-462 executes blood vessel extraction by performing determination processing for a blood vessel region and a non-blood vessel region, using an OCTA front image. As an example of the determination processing, it is sufficient that pixels satisfying a predetermined threshold value are extracted as a blood vessel region using threshold processing. The threshold value may be a preset fixed value or may be arbitrarily set by a subject. Alternatively, the threshold value may be adaptively set based on a predetermined algorithm (e.g., histogram analysis) in accordance with an OCTA front image. In the blood vessel extraction processing, binary information representing blood vessel or non-blood vessel may be used, or a continuous value of likelihood of being a blood vessel (e.g., a distance from a threshold value) may be used. Specific color information may be added to a blood vessel region, or color information may be added with predetermined gradation in a case where a continuous value is employed. The color and gradation representing blood vessel information are not limited to red-based color and gradation, and may be made freely-selectable by the operator.

In addition, color may be added in accordance with the depth of a blood vessel based on OCTA data. By adding color to a blood vessel in this manner, an image to be used for the operator setting an ROI becomes easier to understand. As a matter of course, blood vessel extraction may be performed from OCTA data. By extracting a blood vessel as three-dimensional information, color information can be added based on the position and thickness of the blood vessel.

The display control unit 101-05 performs blood vessel measurement based on blood vessel information extracted by the extraction unit 101-462, and displays a measurement result on the display unit 104. In the blood vessel measurement, for example, a blood vessel density or a blood vessel area can be used. As a density of a blood vessel region, an area of a blood vessel per unit area is obtained by calculating, for example, a ratio of a blood vessel region in the entire region of an ROI. A value to be measured in the blood vessel measurement is not limited to this. A blood vessel total amount or a blood vessel meandering property may be measured.

Furthermore, an ROI may be divided into a plurality of regions, and a difference or a ratio between measured values of the respective regions may be calculated. By calculating the difference or the ratio, for example, a symmetric property of a blood vessel can be evaluated. A blood vessel density may be displayed as an analysis result as a color map image by associating a density of each predetermined area with color data. A color map image and an OCTA front image may be blended and displayed at a predetermined transmissivity (e.g., 50%). In addition, a blend image of an OCTA front image and an OCT front image, and a color map image may be blended and displayed. A transmissivity with respect to a color map image may be fixed, or may be made designatable by the operator.

A periodic inspection may be performed as follow-up of the subject, and a follow-up display screen on which analysis results are arranged in chronological order may be displayed. In this case, comparison of analysis results may be performed by the comparison unit 101-464, and furthermore, a changed result may be displayed with an emphasis by the emphasis unit 101-461.

(Analysis Processing Procedure of Optive Nerve Head)

Figure 5:
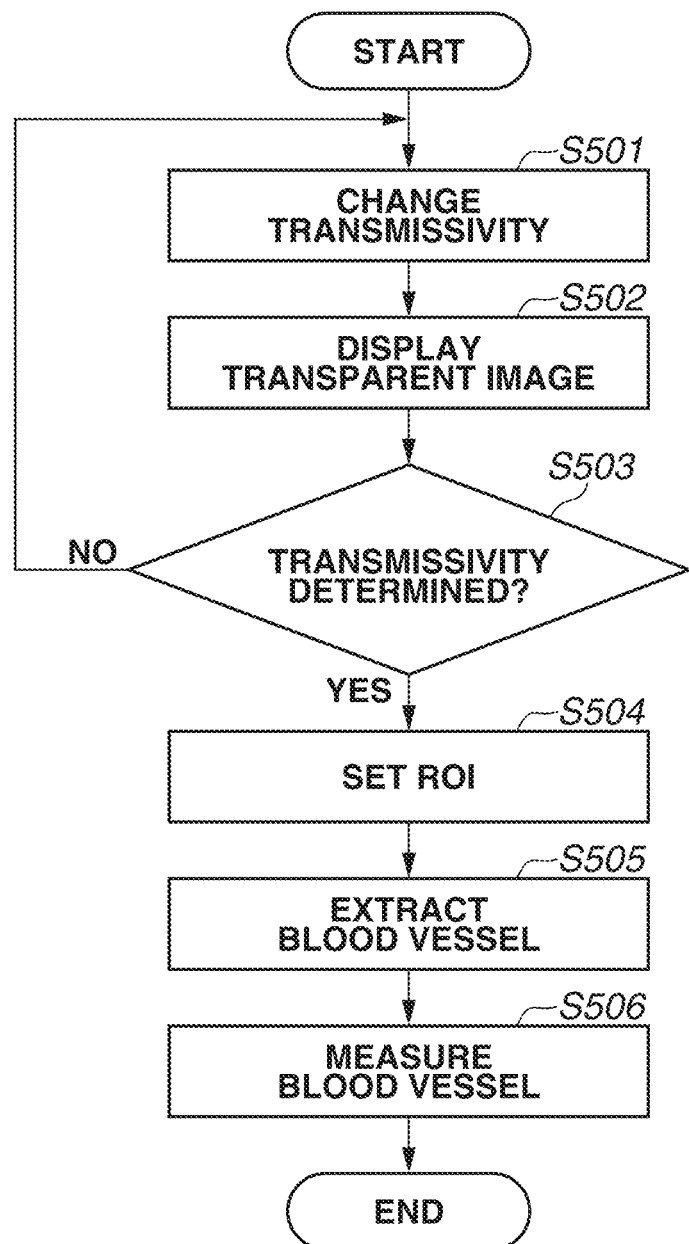
FIG. 5 is a flowchart illustrating analysis processing according to the first exemplary embodiment.

A processing procedure of the image processing apparatus 101 of the present exemplary embodiment will now be described with reference to FIG. 5. In step S501, a transmissivity a of an OCT front image with respect to an OCTA front image of an ONH is changed based on a setting value on a graphical user interface (GUI). In this example, α is assumed to be a real number ranging from 0 to 1. Nevertheless, a may be described in percent figures on the GUI. In step S502, transmission processing of two images is performed based on a changed transmissivity, and a transparent image is displayed on a screen. In step S503, the operator determines a transmissivity at which an ROI setting is easily performed while checking the transparent image. In step S504, an analysis position or an ROI being an analysis region is set. In step S505, an instruction to execute blood vessel extraction processing that is based on the set ROI information is issued. Lastly, in step S506, blood vessel measurement of an ONH is performed, and the measurement result is displayed on the screen.

Heretofore, the description has been given using an example of analysis of an ONH. However, analysis of a macular region of a subject's eye or detection of a foveal avascular zone may be performed. For example, when a neovascular vessel in a deep layer of a macular region is analyzed, an ROI setting of the macular region becomes easier by performing transmission processing on an OCT front image of a surface layer instead of a layer corresponding to an OCTA front image. That is, layers of the OCTA front image and the OCT front image need not be always consistent, and transmission processing may be performed between images for different layers.

(Analysis of Foveal Avascular Zone)

Hereinafter, the detection of a foveal avascular zone (FAZ) will be described. Because an FAZ is an avascular region and has low brightness, the FAZ is extracted, for example, by determining connectivity of brightness in a peripheral portion based on a center point of an FAZ analysis region. It is sufficient that any of known methods is used as an extraction method. There are, for example, extraction using a region expansion method, and extraction using a dynamic contour model such as Snake. The application of the above-described analysis processing is not limited to a blood vessel. The above-described analysis processing can also be applied to a vascular channel analysis (e.g., lymph channel) serving as a vascular channel analysis field. Furthermore, in the present exemplary embodiment, the description has been given using an example of an OCTA front image. However, an order of motion contrast data is not limited. For example, three-dimensional information obtained by performing weighted average from OCTA data and OCT may be generated, and a three-dimensional ROI may be set. As a matter of course, motion contrast data may be one-dimensional motion contrast data or two-dimensional motion contrast data.

Furthermore, a setting of an ROI can also be performed in a tomographic image. If a check button 305 illustrated in FIG. 3A is turned on, a line 306 is displayed on an OCTA front image. The operator can move the position of the line 306 while dragging this line using a mouse. In synchronization with the operation, a tomographic image 307 is updated to a corresponding tomographic image. Intersection points of the set ROI 304 and the line 306 may be displayed on the tomographic image 307 as a line 308 extending in a vertical direction. By horizontally moving the line 308 while dragging the line 308 using the mouse, the operator may adjust the ROI while checking the ROI in the tomographic image. In accordance with the adjustment using the line 308, the shape of the ROI 304 changes in such a manner as to smoothly become contiguous. In addition, a movable range of the line 308 may be suppressed to a range in which ROI adjustment in a tomographic image does not break the shape of the ROI 304.

An OCTA tomographic image and an OCT tomographic image may be blended and displayed in the tomographic image 307, which is not illustrated. In this case, the slide bar 302 may be used in common, or an individual slide bar may be added. Particular in data of an unhealthy eye, checking whether a blood vessel extracted on an OCTA tomographic image is appropriate can be sometimes performed to some extent, by increasing a transmissivity of an OCT tomographic image. In other words, a more detailed ROI may be set while performing transmission processing between the respective tomographic images of OCTA data and OCT data.

In addition, a second medical image used in transmission processing may be an image obtained by an SLO or a fundus camera. Alternatively, the second medical image may be an OCTA front image of another layer. In this case, positional registration is desirably performed between images to be subjected to transmission processing.

Furthermore, the number of images to be used in transmission processing is not limited to two. Depending on the case, it is considered that a third medical image is added by weighted addition. For example, a second blend image may be acquired by performing blend processing of a third medical image and a first blend image at a second transmissivity. The first blend image is a blend image obtained by performing blend processing of a first medical image and a second medical image at a first transmissivity.

Second Exemplary Embodiment

The description will be given of a case where an image processing apparatus according to the present exemplary embodiment performs analysis processing while setting an analysis position and an analysis region in OCT data with reference to an OCTA front image.

The thickness of an optive nerve fiber layer, a depression degree of an optive nerve head, and a curvature of an eyeball shape can be analyzed from OCT data. In this manner, it is possible to recognize the states of various diseases from layer thickness information and curvature information of an eyeball. In addition, the layer thickness information and the curvature information may be displayed as an image by converting the information into a color map representing a thickness and a curvature as color gradations, or an ROI may be divided into a plurality of regions and each average value of the regions may be displayed.

Alternatively, it is considered that analyzing the state of a cribriform plate is also beneficial to the diagnosis of glaucoma. Specifically, the thickness of a cribriform plate can also be measured by performing appropriate segmentation processing on a tomographic image of OCT data.

Depending on the subject's eye, effective analysis can be performed in some cases by setting an ROI while making a comparison with stricter blood vessel information. In a case of excessive myopia, for example, an eyeball shape has distortion, and it therefore becomes possible to set an ROI while simultaneously checking blood vessel information, by performing transmission processing of an OCTA front image on an OCT front image at a designated transmissivity. It becomes possible to analyze a layer thickness or a curvature based on the set ROI.

Alternatively, the present invention can be used in the case of making a complex determination by performing transmission processing of an OCTA front image on an OCT front image or an analysis result image, aside from the setting of an ROI.

Specifically, an operator can visually recognize the state of a blood vessel in a region, for example, with a low layer thickness by performing transmission processing of an OCTA front image on a color map image of a layer thickness. The same applies to a color map image of a curvature. Alternatively, the thickness of a cribriform plate and the state of a flow of blood entering the cribriform plate can be simultaneously checked, by adding blood vessel information at a designated transmissivity when an analysis result of a cribriform plate is checked.

In the case of motion contrast data, visual recognition of a blood vessel is relatively difficult in a location where leakage of a blood vessel or a blood flow amount is small. In a case where transmission processing of blood flow information is desired to be performed more strictly, an image obtained by fluorescent fundus contrast study using fluorescein or indocyanine green may thus be used as a second medical image.

Heretofore, analysis of OCT data has been described in the present exemplary embodiment. However, it is not limited to this. In addition, a first medical image to be subjected to transmission processing is not limited to an OCT front image, and may be an image visualizing an analysis result. Similarly to the first exemplary embodiment, a tomographic image may be used. Furthermore, a second medical image to be subjected to transmission processing is not limited to an OCTA front image, and is only required to be an image of a type different from the first medical image. At this time, the first medical image and the second medical image are only required to be images of mutually corresponding regions in a subject.

Third Exemplary Embodiment

The description will be given of a case where an image processing apparatus according to the present exemplary embodiment adaptively changes a transmissivity for each pixel for transmission processing performed in the above-described various exemplary embodiments. For example, in a case where transmission processing of an OCTA front image and an OCT front image is performed, information regarding a blood vessel becomes important.

In view of the foregoing, a method of transmission processing is switched by preliminarily allocating classification, as an attribute, of a blood vessel region or a non-blood vessel region to each pixel when transmission processing is performed. The extraction of a blood vessel region has been described in the first exemplary embodiment. The simplest way is to allocate an attribute of nonexecution of transmission processing to pixels of a blood vessel region, and allocate an attribute of execution of transmission processing to pixels of a non-blood vessel region. A threshold value for determining a blood vessel attribute may be made designatable by an operator on a screen. Attribute information is changed in accordance with a changed threshold value, and transmission processing is updated based on a changed attribute. A plurality of threshold values for determining an attribute may be made designatable. For example, an attribute may be allocated by separating a blood vessel region and a non-blood vessel region between a range of designated threshold values.

With this configuration, it becomes possible to perform transmission processing of a second medical image only on pixels of a non-blood vessel region without performing transmission processing of blood vessel information. Alternatively, transmission processing may be performed on pixels having an attribute of a blood vessel region, while suppressing a transmissivity of transmission processing. For example, in a case where the operator sets a transmissivity of a second medical image to $\alpha$, it is considered that transmission processing is performed on a non-blood vessel region at a transmissivity of $\alpha$, and transmission processing is performed on a blood vessel region while suppressing a transmissivity to $\alpha/2$. This suppression method may use a predetermined ratio or a function based on the transmissivity of $\alpha$ may be prepared.

In addition, whether a region is a blood vessel region or a non-blood vessel region may be separately held as a continuous value regarding a likelihood of being a blood vessel. In this case, for example, a largest transmissivity for a blood vessel attribute with respect to a largest transmissivity designated by an operator may be preset, and a transmissivity may be determined based on a numerical value indicating a likelihood of being a blood vessel, with respect to the transmissivity designated by the operator. A transmission processing method is not limited to this, and various modifications can be made as long as transmission processing can be performed based on attribute information of each pixel.

Furthermore, a plurality of attributes may be held. In the case of an OCTA front image, attributes of blood vessels are managed while separating into at least two ranges corresponding to, for example, a shallow portion and a deep portion in the depth direction of OCTA data. An operator may be enabled to instantaneously switch an attribute to be used, based on an instruction on a GUI.

In the above-described description, an attribute is allocated to a pixel based on a blood vessel region and a non-blood vessel region, but the attribute allocation is not limited to this, and various attributes can be applied. For example, an attribute of nonexecution of transmission processing may be allocated to a pixel having a specific signal value (e.g., 0) in a second medical image. Alternatively, an attribute may be allocated a preset partial region. For example, an attribute that is based on a bleeding region and a non-bleeding region may be allocated to each pixel by manually designating, on a GUI, a region in which bleeding is recognized.

Furthermore, because a depth information of a blood vessel is obtained from OCTA data, an attribute value may be set based on depth information of a blood vessel. It is sufficient to preliminarily determine whether to use a maximum value, a minimum value, or an average value in a case where a blood vessel overlaps when a motion contrast front image is displayed. In addition, because OCT data includes layer thickness information, an attribute based on a layer thickness may be set.

Attribute information may be individually allocated to a first medical image and a second medical image, or may be allocated only to either one of these images. In addition, a method of transmission processing is not limited to the above-described method, and a person skilled in the art can make various modifications as processing that is based on attribute information set to at least either one.

Heretofore, the description has been given using an example of medical image processing of an eye part in each of the above-described exemplary embodiments. However, the present invention can also be applied to medical image data (e.g., motion contrast data of skin tissue) acquired by an optical coherence tomography.

Fourth Exemplary Embodiment

Hereinafter, a medical image processing apparatus according to a fourth exemplary embodiment will be described with reference to FIGS. 6, 7, and 8. An image processing apparatus 101 according to the present exemplary embodiment includes, for example, an image quality improvement unit (not illustrated), as an image quality improvement means that improves the image quality of motion contrast data. The image quality improvement unit applies image quality improvement processing using machine learning, in place of the above-described synthesis unit 101-42. At this time, the image quality improvement unit in the image processing apparatus 101 (or the image processing unit 101-04) includes an image quality improvement engine. In an image quality improvement method included in the image quality improvement engine according to the present exemplary embodiment, processing that uses machine learning algorithm is performed.

In the present exemplary embodiment, teaching data is used for training of a machine learning model according to a machine learning algorithm. The teaching data includes a group of pairs each including input data that is a low quality image having a specific image capturing condition that is assumed to be a processing target, and output data that is a high quality image that corresponds to the input data. The specific image capturing condition specifically includes a predetermined image capturing region, an image capturing method, an image capturing field angle, and an image size.

In here, the machine learning model is a model obtained by preliminarily performing training (learning) using teaching data (learning data) appropriate for any machine learning algorithm. The teaching data includes a group of one or more pairs each including input data and output data (correct data). The formats and a combination of input data and output data of a pair group included in the teaching data may be those suitable for a desired configuration. For example, one of input data and output data may be an image and the other one may be a numerical value. One of input data and output data may include a group of a plurality of images, and the other one may be a character string. Both of input data and output data may be images.

Specifically, for example, teaching data (hereinafter, first teaching data) includes a group of pairs each including an image acquired by an OCT, and an image capturing region label corresponding to the image. The image capturing region label is a unique numerical value or a character string indicating a region. In addition, as another example of teaching data, teaching data (hereinafter, second teaching data) includes a group of pairs each including a low quality image containing many noises that have been acquired by normal image capturing of an OCT, and a high quality image on which image quality improvement processing has been performed by performing image capturing a plurality of times by an OCT.

At this time, if input data is input to a machine learning model, output data following the design of the machine learning model is output. The machine learning model outputs output data highly likely to correspond to input data, in accordance with the tendency trained using teaching data, for example. In addition, the machine learning model can output a possibility of corresponding to input data, as a numerical value for each type of output data, in accordance with the tendency trained using teaching data, for example. Specifically, for example, an image acquired by an OCT is input to a machine learning model trained using first teaching data, the machine learning model outputs an image capturing region label of an image capturing region captured in the image, or outputs a probability of each image capturing region label. In addition, for example, a low quality image with many noises that has been acquired by normal image capturing of an OCT is input to a machine learning model trained using second teaching data, the machine learning model outputs a high quality image equivalent to an image having been subjected to image quality improvement processing by performing image capturing a plurality of times by an OCT. A machine learning model can be configured not to use output data output by the machine learning model itself, as teaching data, from a view point of quality retention.

A machine learning algorithm includes a method related to deep learning such as a convolutional neural network (CNN). In the method related to deep learning, a degree at which tendency trained using teaching data can be reproduced in output data sometimes varies, if a setting of a parameter for a layer group or a node group included in a neural network varies. For example, in a machine learning model of deep learning that uses first teaching data, a probability of outputting a correct image capturing region label becomes higher in some cases if an appropriate parameter is set. In addition, for example, in a machine learning model of deep learning that uses second teaching data, higher quality image can be output in some cases if an appropriate parameter is set.

Specifically, parameters in the CNN can include, for example, a kernel size of a filter, the number of filters, a value of stride, and a value of dilatation that are to be set in a convolution layer, and the number of nodes output by an affine layer. A parameter group and an epoch number of training can be set to values desirable for a utilization form of a machine learning model, based on teaching data. For example, a parameter group and an epoch number that can output a correct image capturing region label at a high probability, or output a high quality image can be set, based on the teaching data.

One of determination methods of such a parameter group and an epoch number will be exemplified. First of all, 70 percent of a pair group included in teaching data is set as a pair group for training, and remaining 30 percent is set at random as a pair group for evaluation. Training of a machine learning model is then performed using the pair group for training, and a training evaluation value is calculated using the pair group for evaluation at the end of each epoch of training. The training evaluation value is, for example, an average value of a value group obtained by evaluating, using a loss function, an output obtained when input data included in each pair is input to a machine learning model being trained, and output data corresponding to the input data. Lastly, a parameter group and an epoch number that are obtained when a training evaluation value becomes the smallest are determined as a parameter group and an epoch number of the machine learning model. As described above, it is possible to prevent a machine learning model from performing overlearning for the pair group for training, by determining an epoch number by separating a pair group included in teaching data into a pair group for training and a pair group for evaluation.

An image quality improvement engine (learned model for image quality improvement) is a module that outputs a high quality image obtained by performing image quality improvement on an input low quality image. Image quality improvement described in this specification refers to converting an input image into an image with image quality suitable for image diagnosis, and a high quality image refers to an image converted into an image with image quality suitable for image diagnosis. In contrast, a low quality image refers to an image captured without specifically performing a setting for obtaining high image quality, such as a two-dimensional image or a three-dimensional image acquired by, for example, X-ray image capturing, computer tomography (CT), magnetic resonance imaging (MRI), OCT, positron emission computerized-tomography (PET), or single photon emission computed tomography (SPECT) or a continuously-captured three-dimensional moving image of CT. Specifically, a low quality image includes, for example, an image acquired by low-dose image capturing performed by an X-ray image capturing apparatus or a CT, image capturing performed by an MRI not using contrast agent, or short time image capturing by an OCT, and an OCTA image acquired by performing image capturing a small number of times.

In addition, content of image quality suitable for image diagnosis depends on what is desired to be diagnosed in various types of image diagnosis. Thus, image quality suitable for image diagnosis, which cannot be stated unconditionally, includes, for example, image quality with less noise, image quality with high contrast, image quality with color and gradation that make an image capturing target easy to observe, image quality with a large image size, and image quality with high resolution. The image quality suitable for image diagnosis can further include such image quality that an object and gradation that do not actually exist but are drawn in the process of image generation are removed from an image.

In addition, if a high quality image with less noise and high contrast is used for image analysis such as blood vessel analysis processing of an OCTA image, or region segmentation processing of a CT or OCT image, analysis can be performed, in many cases, more accurately than a case where a low quality image is used. Thus, a high quality image output by an image quality improvement engine is sometimes useful not only for image diagnosis but also for image analysis.

In an image processing method included in an image quality improvement method according to the present exemplary embodiment, processing that uses various machine learning algorithms such as deep learning is performed. In the image processing method, existing arbitrary processing may be performed in addition to processing that uses machine learning algorithms Examples of the existing arbitrary processing include, various types of image filter processing, matching processing that uses a database of high quality images corresponding to similar images, and knowledge base image processing.

Figure 6:
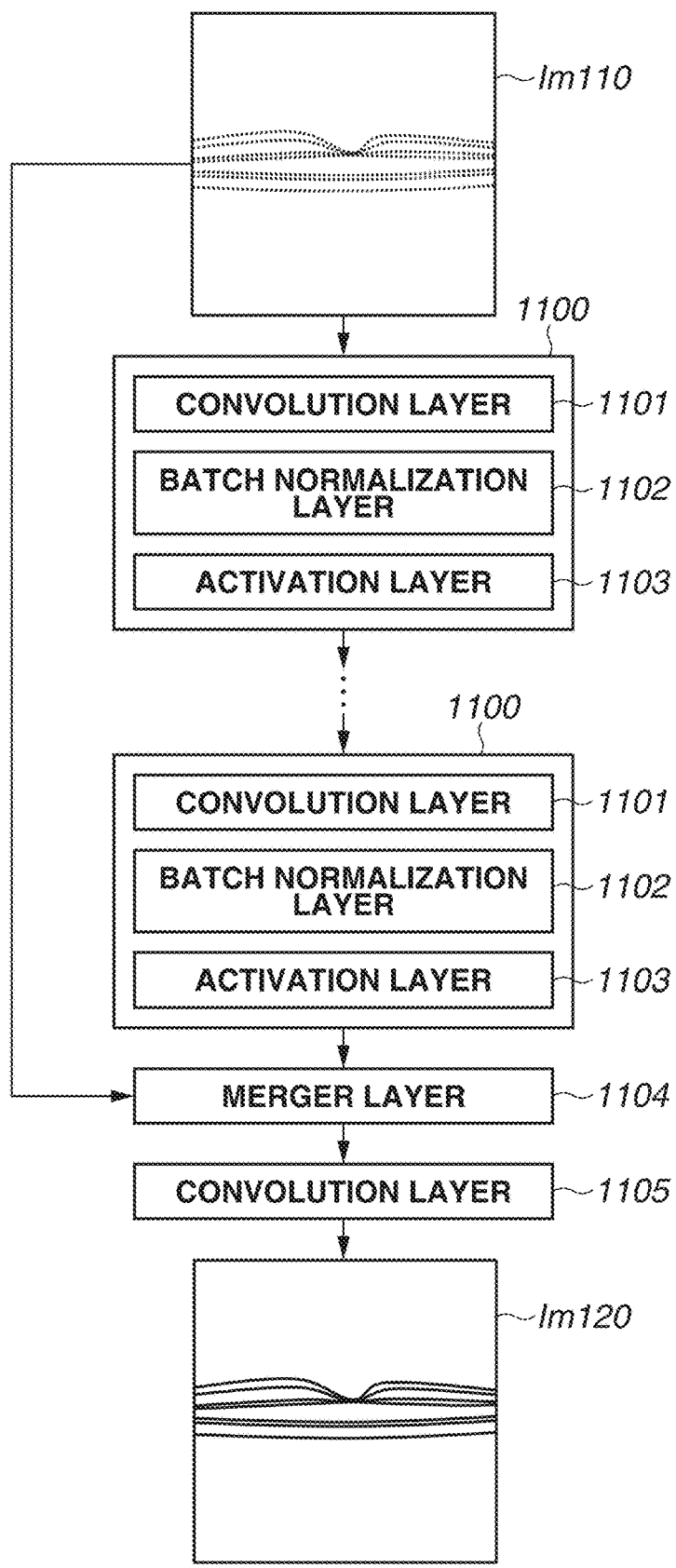
FIG. 6 illustrates an example of a configuration of a neural network related to image quality improvement processing according to a fourth exemplary embodiment.

In particular, a configuration example of a CNN that improves image quality of a two-dimensional image includes a configuration illustrated in FIG. 6. The configuration of the CNN includes a group of a plurality of convolution processing blocks 1100. A convolution processing block 1100 includes a convolution layer 1101, a batch normalization layer 1102, and an activation layer 1103 that uses a rectifier linear unit. The configuration of the CNN includes a merger layer 1104 and a last convolution layer 1105. The merger layer 1104 merges, by connecting or adding, an output value group of the convolution processing block 1100 and a pixel value group constituting an image. The last convolution layer 1105 outputs a pixel value group constituting a high quality image Im120 that has been merged by the merger layer 1104. In such a configuration, a pixel value group constituting an input image Im110 that has been output after passing through the group of the convolution processing block 1100 and the pixel value group constituting the input image Im110 are merged by the merger layer 1104. Thereafter, the merged pixel value group is formed into the high quality image Im120 by the last convolution layer 1105.

For example, by setting the number of convolution processing blocks 1100 to 16, and, as parameters of a group of the convolution layer 1101, setting a kernel size of a filter to a width of three pixels and a height of three pixels, and setting the number of filters to 64, a certain effect of image quality improvement is obtained. Nevertheless, it is actually possible to set a better parameter group using teaching data suitable for a utilization form of a machine learning model, as described in the description of the above-described machine learning model. In a case where a three-dimensional image or a four-dimensional image is processed, a kernel size of a filter may be extended to three or four dimension.

Figure 15:
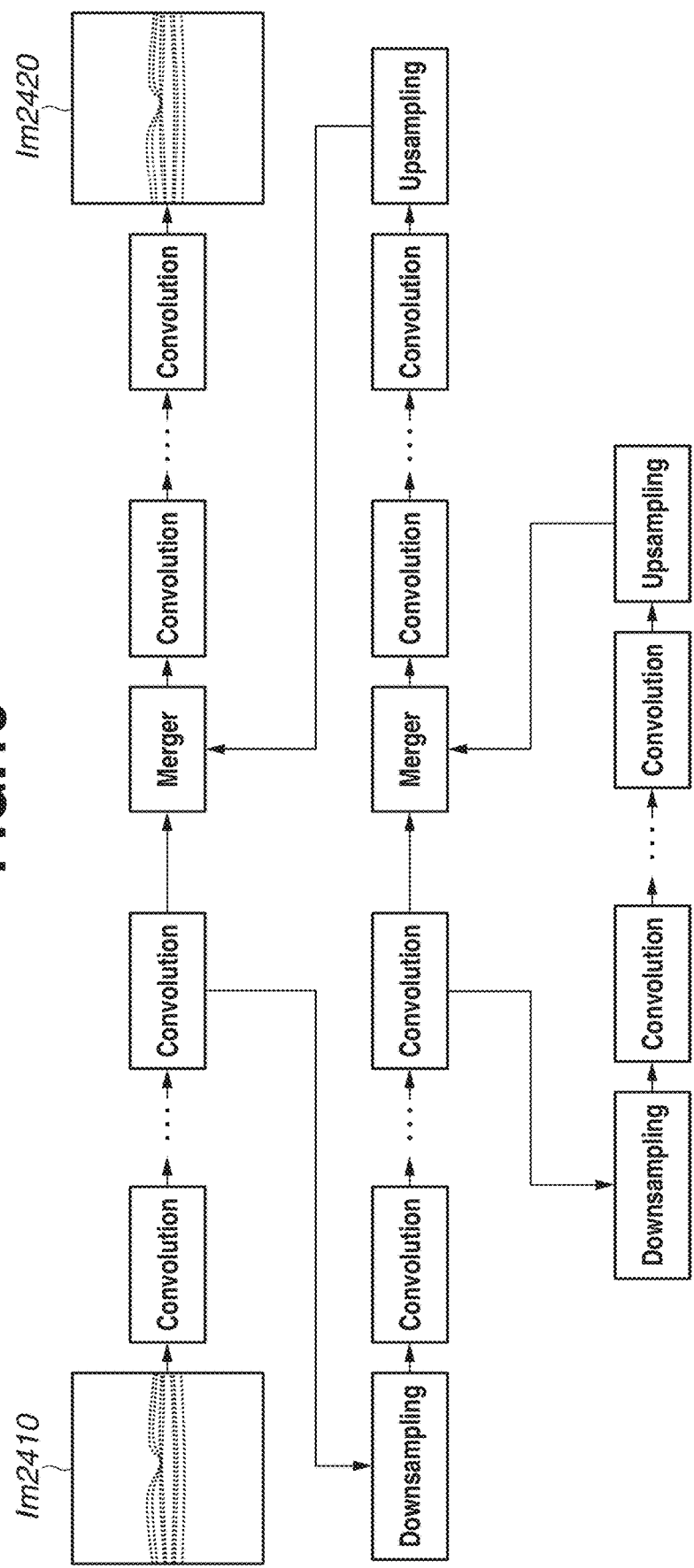
FIG. 15 illustrates an example of a configuration of a neural network related to image quality improvement processing according to the fourth exemplary embodiment.

Another example of a configuration of a CNN in an image quality improvement unit according to the present exemplary embodiment will be described with reference to FIG. 15. FIG. 15 illustrates an example of a machine learning model configuration in an image quality improvement unit. The configuration illustrated in FIG. 15 includes a group of a plurality of layers that performs processing of working an input value group and outputting the worked input value group. The types of layers included in the configuration include a convolution layer, a downsampling layer, an upsampling layer, and a merger layer as illustrated in FIG. 15. The convolution layer is a layer that performs convolution processing on an input value group in accordance with parameters, such as a kernel size of a set filter, the number of filters, a value of stride, and a value of dilatation. A dimension number of a kernel size of the filter may be changed in accordance with a dimension number of an input image. The downsampling layer performs processing of making the number of output value group smaller than the number of input value group by thinning or merging the input value group. Specifically, the processing includes, for example, Max Pooling processing. The upsampling layer performs processing of making the number of output value group larger than the number of input value group by copying an input value group, or adding a value interpolated from an input value group. Specifically, the processing includes, for example, linear interpolation processing. The merger layer is a layer that performs processing of inputting value group, such as an output value group of a certain layer or a pixel value group constituting an image, from a plurality of sources, and merging the value group by connecting or adding. In such a configuration, a pixel value group constituting an input image Im2410 that has been output after passing through convolution processing blocks, and a pixel value group constituting the input image Im2410 are merged by the merger layer. After that, the merged pixel value group is formed into a high quality image Im2420 by a last convolution layer. As a modification example of a configuration of a CNN, for example, a batch normalization layer or an activation layer that uses a rectifier linear unit may be added after the convolution layer, which are not illustrated in FIG. 15.

A GPU can perform efficient calculation by concurrently processing a larger amount of data. Thus, in the case of performing learning a plurality of times using a learning model such as deep learning, it is effective to perform processing using a GPU. In view of the foregoing, a GPU is used in addition to a CPU in processing to be performed by the image processing unit 101-04 serving as an example of a learning unit (not illustrated), according to the present exemplary embodiment. Specifically, learning is performed by the CPU and the GPU performing calculation in cooperation, in the case of executing a learning program including a learning model. In the processing of the learning unit, calculation may be performed only by the CPU or the GPU. The image quality improvement unit may also use a GPU similarly to the learning unit. The learning unit may also include an error detection unit and an update unit, which are not illustrated. The error detection unit obtains an error between correct data and output data that is output from an output layer of a neural network in accordance with input data input to an input layer. The error detection unit may calculate an error between correct data and output data from a neural network, using a loss function. Based on the error obtained by the error detection unit, the update unit updates an internode connection weighting coefficient of a neural network in such a manner that the error becomes smaller. The update unit updates a connection weighting coefficient using, for example, backpropagation. The backpropagation is a method of adjusting an internode connection weighting coefficient of each neural network such that the above-described error becomes smaller.

In the case of using a part of an image processing method such as image processing that uses a CNN, it is necessary to give attention to an image size. Specifically, it should be noted that an input low quality image and an output high quality image require different image sizes in some cases, for dealing with such a problem that the image quality of a peripheral portion of a high quality image is not improved sufficiently.

In a case where an image quality improvement engine that requires different image sizes between an image input to the image quality improvement engine and an output image is employed, image sizes are adjusted appropriately, which is not clearly described in the present exemplary embodiment for the sake of clear description. Specifically, image sizes are adjusted by performing padding on an input image, such as an image to be used in teaching data for training a machine learning model, or an image input to the image quality improvement engine, or connecting image capturing regions near the input image. A region on which padding is to be performed is filled with a certain pixel value, filled with a neighboring pixel value, or is subjected to mirror padding in accordance with the property of an image quality improvement method in such a manner that image quality improvement can be effectively performed.

While an image quality improvement method is executed using only one image processing method in some cases, an image quality improvement method is executed using two or more image processing methods in combination in other cases. Furthermore, a group of a plurality of images quality improvement methods is executed in parallel, a group of a plurality of high quality images is generated, and a high quality image having the highest image quality is finally selected as a high quality image. The selection of the high quality image with the highest image quality may be automatically performed using an image quality evaluation index, or may be performed based on an instruction of an examiner (user) by displaying a group of a plurality of high quality images on a user interface included in an arbitrary display unit.

In some cases, an input image not having been subjected to image quality improvement is more suitable for image diagnosis. Thus, the input image may be included in the final image selection target. In addition, parameters may be input to the image quality improvement engine together with a low quality image. For example, a parameter designating a degree of performing image quality improvement, or a parameter designating an image filter size to be used in an image processing method may be input to the image quality improvement engine together with the input image.

In the present exemplary embodiment, input data of teaching data is a low quality image acquired by an apparatus of the same model type as the tomographic image capturing apparatus 100 using the same setting as the tomographic image capturing apparatus 100. In addition, output data of teaching data is a high quality image acquired by image processing using a setting used in the same model type as the tomographic image capturing apparatus 100. Specifically, the output data is, for example, a high quality image (overlaid image) obtained by performing overlay processing, such as addition average, on an image (original image) group acquired by performing image capturing a plurality of times. The high quality image and the low quality image will be described using motion contrast data of OCTA as an example. The motion contrast data is data, which is used in, for example, an OCTA, indicating a temporal change in image capturing target that is detected by repeatedly capturing images of the same point of the image capturing target. At this time, an En-Face image (motion contrast front image) of OCTA can be obtained by generating a front image using data in a desired range in the depth direction of the image capturing target among calculated motion contrast data (an example of three-dimensional medical image data). Hereinafter, repeatedly performing image capturing of OCT data at the same point will be referred to as Number Of Repeat (NOR).

In the present exemplary embodiment, different two types of methods will be described with reference to FIGS. 12A and 12B as generation examples of a high quality image and a low quality image using overlay processing.

A first method will be described with reference to FIG. 12A, as an example of a high quality image, regarding motion contrast data generated from OCT data obtained by repeatedly performing image capturing of the same point of an image capturing target. FIG. 12A illustrates three-dimensional motion contrast data Im2810 and two-dimensional motion contrast data Im2811 included in the three-dimensional motion contrast data. FIG. 12A also illustrates OCT tomographic images (B scan) Im2811-1 to Im2811-3 for generating the two-dimensional motion contrast data Im2811. In FIG. 12A, the NOR indicates the number of OCT tomographic images in the OCT tomographic images Im2811-1, Im2811-2, and Im2811-3. In the example of FIG. 12A, the NOR is three. The number of OCT tomographic images Im2811-1, Im2811-2, and Im2811-3 are captured at predetermined time intervals ($\Delta t$). The same point indicates one line in a front direction (X-Y) of a subject's eye. In FIG. 12A, the same point corresponds to a point of the two-dimensional motion contrast data Im2811. The front direction is an example of a direction intersecting with the depth direction. Since motion contrast data is data indicating a detected temporal change, the NOR is set to at least two for generating the data. For example, in a case where an NOR is two, one piece of motion contrast data is generated. In a case where an NOR is three, two pieces of data are generated in the case of generating motion contrast data using only OCT data at neighboring time intervals (first and second times, and second and third times). In the case of generating motion contrast data also using OCT data at separated time intervals (first and third times), three pieces of data are generated in total. In other words, if an NOR is increased to three times, four times, and so on, the number of pieces of motion contrast data at the same point also increases. By aligning the positions of a plurality of motion contrast data pieces acquired by repeatedly performing image capturing of the same point, and performing overlay processing, such as addition average, motion contrast data with high image quality can be generated. Thus, an NOR is set to at least three times or more, and desirably set to five times or more. In contrast, as an example of a low quality image corresponding to the high image quality image, a motion contrast data not having been subjected to overlay processing, such as addition average, can be employed. In this case, a low quality image is desirably used as a reference image in performing overlay processing such as addition average. When overlay processing is performed, almost no spatial positional shift is generated between the reference image and an image having been subjected to overlay processing, if position alignment is performed by deforming the position or shape of a target image with respect to the reference image. It is therefore possible to easily make a pair of a low quality image and a high quality image. Instead of a reference image, a target image on which image deformation processing for position alignment has been performed may be used as the low quality image. By setting each image of an original image group (reference images and target images) as input data, and setting a corresponding overlaid image as output data, a group of a plurality of pairs can be generated. For example, in a case where one overlaid image is to be obtained from a group of 15 original images, a pair of the first original image in the original image group and an overlaid image, and a pair of the second original image in the original image group and an overlaid image can be generated. In this manner, in a case where one overlaid image is to be obtained from the group of 15 original images, a group of 15 pairs each pair including one image in the original image group and an overlaid image can be generated. By repeatedly performing image capturing of the same point in a main scanning (X) direction, and performing the scanning while shifting an image capturing position in a sub scanning (Y) direction, three-dimensional high image quality data can be generated.

A second method will be described with reference to FIG. 12B, in which a high quality image is generated by performing overlay processing on motion contrast data obtained by performing image capturing of the same region of an image capturing target a plurality of times. The same region refers to a region having a size such as 3 mm×3 mm or 10 mm×10 mm in the front direction (X-Y) of a subject's eye, and three-dimensional motion contrast data including the depth direction of a tomographic image is acquired. When performing overlay processing by performing image capturing of the same region a plurality of times, an NOR is desirably set to two or three times for making one image capturing time short. To generate three-dimensional motion contrast data with high image quality, at least two or more three-dimensional data pieces of the same region are acquired. FIG. 12B illustrates an example of a plurality of pieces of three-dimensional motion contrast data. Similarly to FIG. 12A, FIG. 12B illustrates three-dimensional motion contrast data pieces Im2820, Im2830, and Im2840. Using these two or more three-dimensional motion contrast data pieces, position alignment processing in the front direction (X-Y) and the depth direction (Z) is performed, data causing an artifact is removed from each piece of data, and then, averaging processing is performed. One piece of three-dimensional motion contrast data with high image quality from which an artifact is removed can thereby be generated. By generating an arbitrary plane from three-dimensional motion contrast data, a high quality image is obtained. In contrast, a low quality image corresponding to this is desirably set to an arbitrary plane generated from reference data in performing overlay processing such as addition average. As described in the first method, almost no spatial positional shift is generated between a reference image and an image having been subjected to addition average, it is therefore possible to easily make a pair of a low quality image and a high quality image. An arbitrary plane generated from target data on which image modification processing of position alignment has been performed, instead of reference data may be set as the low quality image.

Because image capturing performs image capturing once in the first method, a burden placed on a subject is small. Nevertheless, as the number of NOR increases, an image capturing time of one image capturing becomes longer. In addition, a good image is not always obtained in a case where opacification of an eye occurs or an artifact such as an eyelash enters an eye during image capturing. Because image capturing is performed a plurality of times in the second method, burden placed on a subject increases a bit.

Nevertheless, an image capturing time for one image can be short, and a good image with less artifacts can be finally obtained even if an artifact enters an eye in one image capturing as long as no artifact is included in another image capturing. In view of these features, an arbitrary method is selected in accordance with the status of a subject when data is collected.

In the present exemplary embodiment, motion contrast data has been described as an example, which is not limited to this. Because OCT data is captured for generating motion contrast data, the same processing can be performed in the OCT data using the above-described method. In the present exemplary embodiment, the description of tracking processing has been omitted. However, since images of the same point or the same region of the subject's eye are captured, it is desirable to perform image capturing while tracking a subject's eye.

Figure 13A:
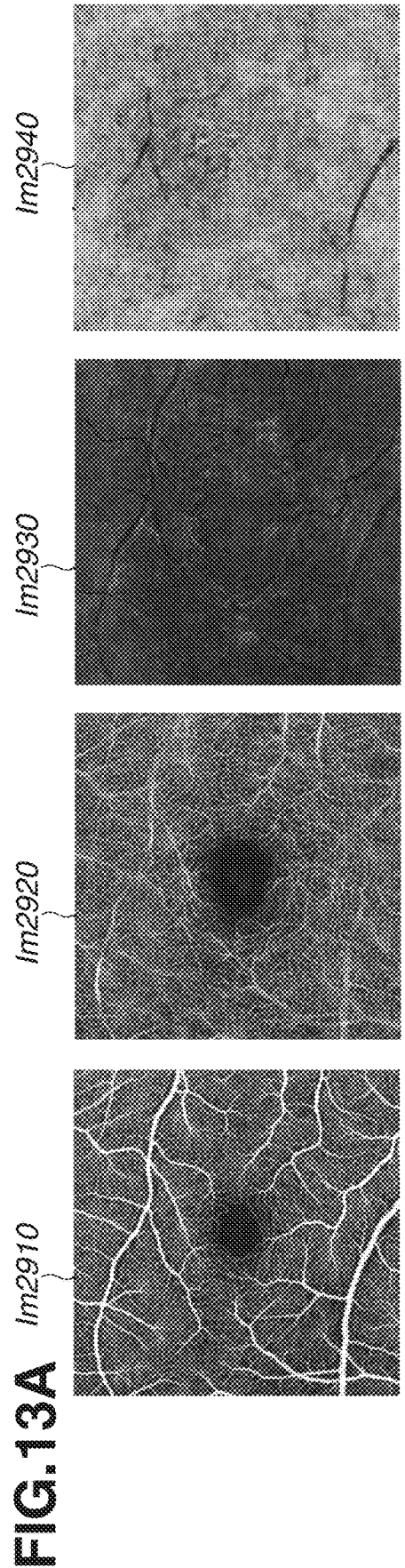
FIG. 13A illustrates an example of a teaching image related to image quality improvement processing.

In the present exemplary embodiment, since a pair of three-dimensional high image quality data and low image quality data has been made, a pair of arbitrary two-dimensional images can be generated from this. Regarding this, the description will be given with reference to FIG. 13A. For example, in a case where a target image is set to an En-Face image of OCTA, an En-Face image of OCTA is generated in a desired depth range from three-dimensional data. The desired depth range refers to a Z direction in FIG. 12A. FIG. 13A illustrates an example of an En-Face image of OCTA to be generated at this time. Learning is performed using, as En-Face images of OCTA, En-Face images of OCTA generated in different depth ranges, such as a surface layer (Im2910), a deep layer (Im2920), an outer layer (Im2930), and a choroid blood vessel network (Im2940). The types of En-Face images of OCTA are not limited to these. An En-Face image of OCTA for which a different depth range is set by varying a reference layer and an offset value may be generated and the number of types may be increased. When learning is performed, learning may be individually performed for each En-Face image of OCTA in a different depth, a plurality of images in different depth ranges may be learned in combination (e.g., divide into surface layer side and deep layer side), or En-Face images of OCTA in all depth ranges may be learned together. In the case of an En-Face image of brightness generated from OCT data, learning is performed using a plurality of En-Face images generated from arbitrary depth ranges, similarly to En-Face of OCTA. For example, a case will be considered where an image quality improvement engine includes a machine learning engine obtained using learning data including a plurality of motion contrast front images corresponding to different depth ranges of a subject's eye. At this time, an acquisition unit can acquire a motion contrast front image corresponding to a partial depth range of a long depth range including different depth ranges, as a first image. In other words, a motion contrast front image corresponding to a depth range different from a plurality of depth ranges corresponding to a plurality of motion contrast front images included in learning data can be used as an input image in image quality improvement. A motion contrast front image in the same depth range as a depth range at the time of learning may be used as an input image in image quality improvement. In addition, a part of depth ranges may be set in accordance with any button on a user interface being pressed by an examiner, or may be automatically set. The above-described content is not limited to a motion contrast front image, and can be applied to, for example, an En-Face image of brightness.

Figure 13B:
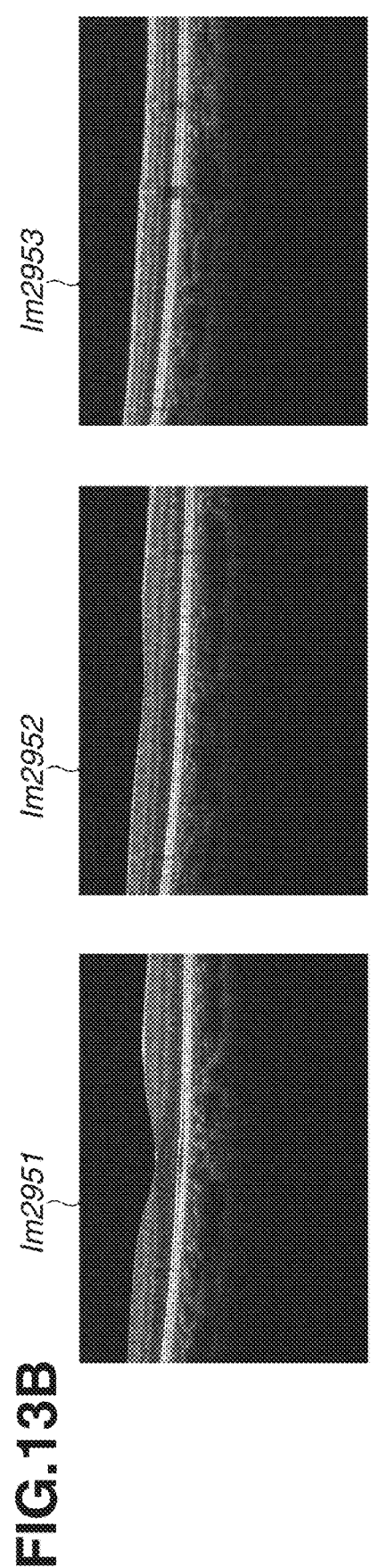
FIG. 13B illustrates an example of a teaching image related to image quality improvement processing.

In a case where a processing target image is a tomographic image, learning is performed using an OCT tomographic image being B scan or a tomographic image of motion contrast data. Regarding this, the description will be given with reference to FIG. 13B. FIG. 13B illustrates tomographic images Im2951, Im2952, and Im2953 of OCT. FIG. 13B illustrates different images because the tomographic images Im2951 to Im2953 are tomographic images of locations with different positions in the sub scanning (Y) direction. In tomographic images, learning may be performed together without regard to a difference in position in the sub scanning direction. Nevertheless, in the case of images obtained by performing image capturing of different image capturing regions (e.g., macular region center, and optive nerve head portion center), learning may be individually performed for each region, or learning may be performed together without regard to an image capturing region. Image feature amounts of an OCT tomographic image and a tomographic image of motion contrast data greatly differ from each other, it is desirable to individually perform learning.

Pixels drawn in common in an original image group are emphasized in an overlaid image having been subjected to overlay processing, the overlaid image thereby becomes an image with high quality suitable for image diagnosis. In this case, the generated high quality image becomes a high-contrast image in which a difference between a low brightness region and a high brightness region is clear, as a result of pixels drawn in common being emphasized. For example, in the overlaid image, random noise generated each time image capturing is performed can be reduced, and a region that has not been properly drawn in an original image at a certain time point can be interpolated by another original image group.

In a case where input data of a machine learning model is required to include a plurality of images, a required number of original images group can be selected from the original image group and used as input data. For example, in a case where one overlaid image is to be obtained from a group of 15 original images, if two images are required as input data of a machine learning model, a group of 105 ($_{15}C_2$=105) pairs can be generated.

Among a group of pairs including teaching data, a pair not contributing to image quality improvement can be excluded from the teaching data. For example, in a case where a high quality image being output data constituting a pair of teaching data has image quality unsuitable for image diagnosis, an image output by an image quality improvement engine learned using the teaching data may have image quality unsuitable for image diagnosis. It is thereby possible to reduce a probability of the image quality improvement engine generating the image with image quality unsuitable for image diagnosis, by excluding the pair of which output data has image quality unsuitable for image diagnosis, from the teaching data.

In addition, in a case where average brightness or brightness distribution of an image group of pairs greatly differs, an image quality improvement engine learned using the teaching data may output an image unsuitable for image diagnosis that has brightness distribution greatly different from that of a low quality image. Thus, a pair of input data and output data of which average brightness or brightness distribution greatly differs can be excluded from the teaching data.

Furthermore, in a case where a structure or a position of an image capturing target drawn in an image group of pairs greatly differs, an image quality improvement engine learned using the teaching data may output an image unsuitable for image diagnosis in which an image capturing target is drawn with a structure or at a position that is greatly different from that in a low quality image. Thus, a pair of input data and output data in which a structure or a position of a drawn image capturing target greatly differs can be excluded from the teaching data. In addition, the image quality improvement engine can be configured not to use a high quality image output by itself, as teaching data from an aspect of quality retention.

By using an image quality improvement engine that has performed machine learning in this manner, the image quality improvement unit in the image processing apparatus 101 (or the image processing unit 101-04) can output a high quality image on which contrast improvement or noise reduction is performed by overlay processing, in a case where a medical image acquired by one image capturing is input. The image quality improvement unit can thus generate a high quality image suitable for image diagnosis, based on a low quality image being an input image.

A series of image processing according to the present exemplary embodiment will now be described with reference to a flowchart illustrated in FIG. 7. FIG. 7 is a flowchart of a series of image processing according to the present exemplary embodiment. First of all, when a series of image processing according to the present exemplary embodiment is started, the processing proceeds to step S510.

In step S510, the image acquisition unit 101-01 acquires an image captured by the tomographic image capturing apparatus 100, as an input image from the tomographic image capturing apparatus 100 connected via a circuit or a network. The image acquisition unit 101-01 may acquire an input image in accordance with a request from the tomographic image capturing apparatus 100. Such a request may be issued, for example, when the tomographic image capturing apparatus 100 generates an image, when, before or after the tomographic image capturing apparatus 100 stores the generated image into a storage device included in the tomographic image capturing apparatus 100, the stored image is displayed on the display unit 104, or when a high quality image is used in image analysis processing.

The image acquisition unit 101-01 may acquire data for generating an image, from the tomographic image capturing apparatus 100, and acquire an image generated by the image processing apparatus 101 based on the data, as an input image. In this case, any existing image generation method may be employed as an image generation method for the image processing apparatus 101 generating various images.

In step S520, an image capturing condition acquisition unit (not illustrated) in the image processing apparatus 101 acquires an image capturing condition group of an input image. Specifically, the image capturing condition acquisition unit acquires an image capturing condition group stored in a data structure including an input image, in accordance with a data format of the input image. As described above, in a case where an image capturing condition is not stored in the input image, the image capturing condition acquisition unit can acquire an image capturing information group including an image capturing condition group from the tomographic image capturing apparatus 100 or an image management system (not illustrated).

In step S530, an image quality improvement executability determination unit (not illustrated) in the image processing apparatus 101 determines whether the image quality of an input image can be improved by an quality improvement engine included in an image quality improvement unit in the image processing apparatus 101 (or the image processing unit 101-04), using the acquired image capturing condition group. Specifically, the image quality improvement executability determination unit determines whether an image capturing region, an image capturing method, an image capturing field angle, and an image size of the input image satisfy a condition manageable by the image quality improvement engine.

In a case where the image quality improvement executability determination unit determines all image capturing conditions and determines that the image capturing conditions are manageable, the processing proceeds to step S540. In contrast, in a case where the image quality improvement executability determination unit determines that the image quality improvement engine cannot manage the input image, based on these image capturing conditions, the processing proceeds to step S550.

Depending on a setting or a mounting configuration of the image processing apparatus 101, the image quality improvement processing in step S540 may be executed, even if it is determined that the input image is unprocessable, based on a part of an image capturing region, an image capturing method, an image capturing field angle, and an image size. Such processing may be performed in a case, for example, where the image quality improvement engine is assumed to be exhaustively manageable any image capturing region of a subject, and mounted to be manageable even if input data includes an unknown image capturing region. In addition, the image quality improvement executability determination unit may determine whether at least one of an image capturing region, an image capturing method, an image capturing field angle, and an image size of the input image satisfies a condition manageable by the image quality improvement engine, in accordance with a desired configuration.

In step S540, the image quality improvement unit improves the image quality of the input image using the image quality improvement engine, and generates a high quality image more suitable for image diagnosis than the input image. Specifically, the image quality improvement unit inputs the input image to the image quality improvement engine, and causes the image quality improvement engine to generate a high quality image with improved image quality. The image quality improvement engine generates a high quality image on which overlay processing is performed using the input image, based on a machine learning model obtained by performing machine learning using teaching data. The image quality improvement engine can thereby generate a high quality image with reduced noise and emphasized contrast more than the input image.

The image quality improvement unit may input parameters to the image quality improvement engine together with the input image in accordance with an image capturing condition group, and adjust, for example, a degree of image quality improvement. In addition, the image quality improvement unit may input parameters corresponding to an input of an examiner, to the image quality improvement engine together with the input image, and adjust, for example, a degree of image quality improvement.

In step S550, if a high quality image is generated in step S540, the display control unit 101-05 outputs the high quality image and displays the high quality image on the display unit 104. In contrast, in a case where it is determined in step S530 that image quality improvement processing is inexecutable, the display control unit 101-05 outputs the input image and displays the input image on the display unit 104. The display control unit 101-05 may display or store an output image on or into the tomographic image capturing apparatus 100 or another apparatus instead of displaying an output image on the display unit 104. The display control unit 101-05 may process an output image to be available to the tomographic image capturing apparatus 100 or another apparatus, or convert a data format in such a manner that the output image can be sent to, for example, an image management system, depending on a setting or a mounting configuration of the image processing apparatus 101.

As described above, the image processing apparatus 101 according to the present exemplary embodiment includes the image acquisition unit 101-01 and the image quality improvement unit. The image acquisition unit 101-01 acquires an input image (first image) being an image of a predetermined region of a subject. The image quality improvement unit generates, from an input image, a high quality image (second image) of which at least one of noise reduction and contrast emphasis has been performed as compared with the input image, using the image quality improvement engine including a machine learning engine. The image quality improvement engine includes a machine learning engine that uses an image obtained by overlay processing, as learning data.

With this configuration, the image processing apparatus 101 according to the present exemplary embodiment can output a high quality image with reduced noise or emphasized contrast, from the input image. Thus, the image processing apparatus 101 can acquire an image suitable for image diagnosis such as a clear image or an image in which a region or a lesion desired to be observed is emphasized, with smaller sacrifice without increasing invasiveness of a photographer or a subject or increasing labors, as compared with the prior art.

In addition, the image processing apparatus 101 further includes the image quality improvement executability determination unit that determines, with respect to an input image, whether a high quality image can be generated using an image quality improvement engine. The image quality improvement executability determination unit performs the determination based on at least one of an image capturing region, an image capturing method, an image capturing field angle, and an image size of the input image.

With this configuration, the image processing apparatus 101 according to the present exemplary embodiment can omit an input image unprocessable by the image quality improvement unit, from a target of image quality improvement processing, and reduce a processing load on the image processing apparatus 101 and the occurrence of an error.

In the present exemplary embodiment, the display control unit 101-05 is configured to display a generated high quality image on the display unit 104, but an operation of the display control unit 101-05 is not limited to this. For example, the display control unit 101-05 can also output a high quality image to the tomographic image capturing apparatus 100 or another apparatus connected to the image processing apparatus 101. The high quality image can thus be displayed on user interfaces of these apparatuses, stored in an arbitrary storage device, used for arbitrary image analysis, or sent to an image management system.

In the present exemplary embodiment, the image quality improvement executability determination unit determines whether an input image is an input image of which image quality can be improved by the image quality improvement engine, and if an input image is an input image of which image quality can be improved, the image quality improvement unit performs image quality improvement. In contrast to this, the image quality of an image acquired from the tomographic image capturing apparatus 100 may be unconditionally improved, in a case where image capturing is performed by the tomographic image capturing apparatus 100 using only an image capturing condition under which image quality improvement can be performed. In this case, as illustrated in FIG. 8, the processing in steps S520 and S530 can be omitted, and step S540 can be executed subsequent to step S510.

In the present exemplary embodiment, the display control unit 101-05 is configured to display a high quality image on the display unit 104. Nevertheless, the display control unit 101-05 may display a high quality image on the display unit 104 in accordance with an instruction from an examiner. For example, the display control unit 101-05 may display a high quality image on the display unit 104 in accordance with an examiner pressing any button on a user interface of the display unit 104. In this case, the display control unit 101-05 may display the high quality image by switching a displayed image from an input image, or may display a high quality image next to the input image.

Furthermore, when displaying a high quality image on the display unit 104, the display control unit 101-05 may display, together with the high quality image, a display indicating that the displayed image is a high quality image generated by processing that uses a machine learning algorithm. In this case, the user can easily identify, based on the display, that the displayed high quality image is not an image acquired by image capturing, it is thereby possible to reduce wrong diagnosis and enhance diagnosis efficiency. The display indicating that the displayed image is a high quality image generated by processing that uses a machine learning algorithm may be any display as long as the display makes an input image and the high quality image generated by processing distinguishable.

The display control unit 101-05 may display, on the display unit 104, a display indicating teaching data used by a machine learning algorithm for performing learning, as a display indicating that the displayed image is a high quality image generated by processing that uses a machine learning algorithm. The display may include an arbitrary display regarding teaching data, such as explanation of types of input data and output data of teaching data, and an image capturing region included in the input data and the output data.

In the image quality improvement engine according to the present exemplary embodiment, an overlaid image is used as output data of teaching data, but teaching data is not limited to this. The output data of teaching data may use, for example, a high quality image obtained by performing at least one of overlay processing, processing group described below, and an image capturing method described below, which serve as means for obtaining a high quality image.

As output data of teaching data, a high quality image obtained by performing, for example, maximum a posteriori probability (MAP) estimation processing on an original image group may be used. In the MAP estimation processing, a likelihood function is obtained from a probability density of each pixel value in a plurality of low quality images, and a true signal value (pixel value) is estimated using the obtained likelihood function.

A high quality image obtained by the MAP estimation processing becomes a high-contrast image based on a pixel value close to the true signal value. Since the estimated signal value is obtained based on the probability density, a noise generated at random is reduced in the high quality image obtained by the MAP estimation processing. The image quality improvement engine can thereby generates, from an input image, a high quality image with reduced noise or high contrast that is suitable for image diagnosis, by using, as teaching data, the high quality image obtained by the MAP estimation processing. A generation method of a pair of input data and output data of teaching data may be a method similar to a method used in a case where an overlaid image is used as teaching data.

As output data of teaching data, a high quality image obtained by applying smoothing filter processing to an original image may be used. In this case, the image quality improvement engine can generate, from an input image, a high quality image in which random noise is reduced. Furthermore, as output data of teaching data, an image obtained by applying gradation conversion processing to an original image may be used. In this case, the image quality improvement engine can generate a high quality image with emphasized contrast from an input image. A generation method of a pair of input data and output data of teaching data may be a method similar to a method used in a case where an overlaid image is used as teaching data.

Input data of teaching data may be an image acquired from an image capturing apparatus having the same image quality tendency as the tomographic image capturing apparatus 100. Output data of teaching data may be a high quality image obtained by high-cost processing such as a successive approximation method, or may be a high quality image acquired by performing image capturing of a subject corresponding to input data, using an image capturing apparatus having higher performance than the tomographic image capturing apparatus 100. Furthermore, output data may be a high quality image acquired by performing rule-based noise reduction processing. The noise reduction processing can include, for example, processing of replacing a single high brightness pixel that is apparently noise and emerges in a low brightness region, with an average value of neighboring low brightness pixel values. The image quality improvement engine may therefore use, as learning data, an image captured by an image capturing apparatus having higher performance than an image capturing apparatus used for image capturing of an input image, or an image acquired by an image capturing process including a larger number of man-hours than that of an image capturing process of an input image. For example, in a case where a motion contrast front image is set as an input image, the image quality improvement engine may use, as learning data, an image obtained by performing OCTA image capturing by an OCT image capturing apparatus having higher performance than an OCT image capturing apparatus used in OCTA image capturing of the input image, or an image obtained in an OCTA image capturing process including a larger number of man-hours than that of an OCTA image capturing process of the input image.

Although description has been omitted in the present exemplary embodiment, a high quality image generated from a plurality of images that is to be used as output data of teaching data can be generated from a plurality of images having been subjected to position alignment. The position alignment processing may be performed in the following manner, for example. More specifically, one of a plurality of images is selected as a template, a degree of similarity to another image is obtained while changing a position and an angle of the template, a positional shift amount from the template is obtained, and each image is corrected based on the positional shift amount. Another type of arbitrary existing position alignment processing may also be performed.

In a case of aligning the position of a three-dimensional image, position alignment of a three-dimensional image may be performed by breaking down the three-dimensional image into a plurality of two-dimensional images, and integrating the two-dimensional images each of which has been individually subjected to position alignment. In addition, position alignment of a two-dimensional image may be performed by breaking down the two-dimensional image into one-dimensional images, and integrating the one-dimensional images each of which has been individually subjected to position alignment. Such position alignment may be performed not on an image but on data for generating an image.

In the present exemplary embodiment, in a case where the image quality improvement executability determination unit determines that an input image is manageable by the image quality improvement unit, the processing proceeds to step S540, and image quality improvement processing is started by the image quality improvement unit. In contrast to this, the display control unit 101-05 may display a determination result obtained by the image quality improvement executability determination unit, on the display unit 104, and the image quality improvement unit may start image quality improvement processing in accordance with an instruction from an examiner. At this time, the display control unit 101-05 can display an input image and an image capturing condition, such as an image capturing region that is acquired for the input image, on the display unit 104 together with the determination result. In this case, since image quality improvement processing is performed after an examiner determines whether the determination result is correct, it is possible to reduce image quality improvement processing that is based on erroneous determination.

The display control unit 101-05 may also display an input image and an image capturing condition, such as an image capturing region that is acquired for the input image, on the display unit 104, and the image quality improvement unit may start image quality improvement processing in accordance with an instruction from an examiner, without performing determination by using the image quality improvement executability determination unit.

Fifth Exemplary Embodiment

An image processing apparatus according to the fifth exemplary embodiment will now be described with reference to FIGS. 14A and 14B. In the present exemplary embodiment, the description will be given of an example in which the display control unit 101-05 displays a processing result of the image quality improvement unit in the image processing apparatus 101 (or the image processing unit 101-04) on the display unit 104. In the present exemplary embodiment, the description will be given with reference to FIGS. 14A and 14B, but a display screen is not limited to this. The image quality improvement processing can be similarly applied to a display screen that displays a plurality of images obtained on different dates and times, side by side as performed in follow-up. The image quality improvement processing can be similarly applied to a display screen for an examiner confirming an image capturing success/failure immediately after image capturing, like an image capturing confirmation screen.

Unless otherwise stated, a configuration and processing of an image processing apparatus according to the present exemplary embodiment are similar to those of the image processing apparatus 101 according to the first exemplary embodiment. Hereinafter, the image processing apparatus according to the present exemplary embodiment will thus be described mainly based on a difference from the image processing apparatus according to the first exemplary embodiment.

The display control unit 101-05 can display, on the display unit 104, a plurality of high quality images generated by the image quality improvement unit, and a low quality image not having been subjected to image quality improvement. A low quality image and a high quality image can be thereby output in accordance with an instruction of an examiner.

Figure 14A:
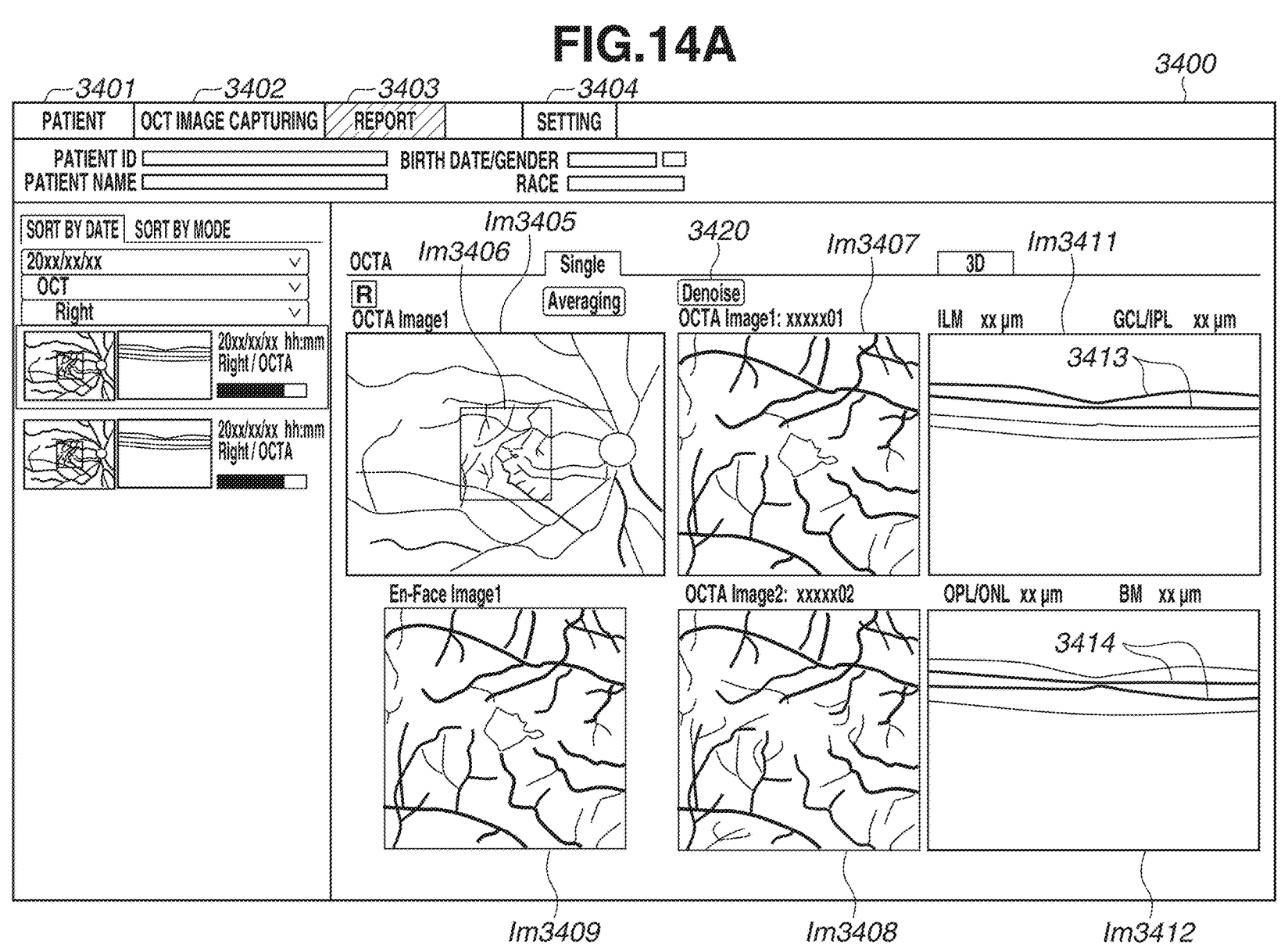

Hereinafter, FIG. 14A illustrates an example of an interface. FIG. 14A illustrates the entire screen 3400, a patient tab 3401, an image capturing tab 3402, a report tab 3403, and a setting tab 3404. Diagonal hatches of the report tab 3403 indicates an active state of a report screen. In the present exemplary embodiment, the description will be given of an example in which the report screen is displayed. In an Im3406, an En-Face image Im3407 of OCTA is displayed with being superimposed on an SLO image Im3405. An SLO image refers to a front image of a fundus that is acquired by a scanning laser ophthalmoscope (SLO) optical system (not illustrated). The report screen includes En-Face images Im3407 and Im3408 of OCTA, an En-Face image Im3409 of brightness, and tomographic images Im3411 and Im3412. Boundary lines 3413 and 3414 indicating vertical ranges of the En-Face images Im3407 and Im3408, respectively, of OCTA are displayed with being superimposed on the tomographic images. A button 3420 is a button for issuing an execution instruction of image quality improvement processing. As described below, the button 3420 may be a button for issuing a display instruction of a high quality image.

In the present exemplary embodiment, the execution of image quality improvement processing is performed by designating the button 3420, or whether or not image quality improvement processing is to be executed is determined based on information stored in a database. First of all, the description will be given of an example of switching between the display of a high quality image and the display of a low quality image by designating the button 3420 in accordance with an instruction from an examiner. The description will be given assuming that a target image of image quality improvement processing is an En-Face image of OCTA. When a screen transitions to the report screen by the examiner designating the report tab 3403, the En-Face images Im3407 and Im3408 of OCTA with low image quality are displayed. After that, by the examiner designating the button 3420, the image quality improvement unit executes image quality improvement processing on the images Im3407 and Im3408 displayed on the screen. After the completion of the image quality improvement processing, the display control unit 101-05 displays a high quality image generated by the image quality improvement unit, on the report screen. Since the Im3406 displays the image Im3407 with being superimposed on the SLO image Im3405, the image Im3406 also displays an image having been subjected to image quality improvement processing. Then, the display of the button 3420 is changed to an active state so that it can be seen that image quality improvement processing has been executed. An execution timing of processing in the image quality improvement unit is not be limited to a timing at which the examiner designates the button 3420. The types of the En-Face images Im3407 and Im3408 of OCTA to be displayed when the report screen is opened are preliminarily identified, image quality improvement processing may therefore be executed when a screen transitions to the report screen. The display control unit 101-05 may also display a high quality image on the report screen at a timing at which the button 3420 is pressed. Furthermore, the types of images on which image quality improvement processing is to be performed in accordance with an instruction from an examiner, or when a screen transitions to the report screen need not be two types. The processing may be performed on images highly likely to be displayed. For example, the processing may be performed on a plurality of En-Face images of OCTA, such as the surface layer (Im2910), the deep layer (Im2920), the outer layer (Im2930), and the choroid blood vessel network (Im2940) as illustrated in FIG. 13A. In this case, an image obtained by performing image quality improvement processing may be temporarily stored in a memory, or may be stored in a database.

The description will now be given of a case where image quality improvement processing is executed based on information stored in a database. In a case where an execution state of image quality improvement processing is stored in a database, image quality improvement processing is executed and an obtained high quality image is displayed by default when a screen transitions to the report screen. By displaying the button 3420 in the active state by default, the examiner can then recognize that image quality improvement processing has been executed and the obtained high quality image is displayed. In a case where the examiner displays a low quality image not having been subjected to image quality improvement processing, the low quality image can be displayed by designating the button 3420 and canceling the active state. In a case where the examiner returns the displayed image to the high quality image, the examiner designates the button 3420. Whether to execute image quality improvement processing that is to be stored in a database is designated by hierarchy by, for example, designating in common to the entire data stored in the database, or designating for each piece of image capturing data (each inspection). For example, in a case where a state of executing image quality improvement processing is stored for the entire database, in a case where an examiner stores a state of not executing image quality improvement processing, for an individual piece of image capturing data (individual inspection), when the image capturing data is displayed next time, display is performed with a state of not executing image quality improvement processing. To store an execution state of image quality improvement processing for each piece of image capturing data (each inspection), a user interface (not illustrated) (e.g., save button) may be used. In addition, when displayed data transitions to another image capturing data (another inspection) or another patient data (e.g., a screen is changed to a display screen other than the report screen in accordance with an instruction from an examiner), a state of executing image quality improvement processing may be stored based on a display state (e.g., state of the button 3420). With this configuration, in a case where whether to execute image quality improvement processing is not designated for each piece of image capturing data (for each inspection), the processing can be performed based on information designated for the entire database, and in a case where whether to execute image quality improvement processing is designated for each piece of image capturing data (for each inspection), the processing can be individually executed based on the information.

The images Im3407 and Im3408 are displayed as En-Face images of OCTA in the present exemplary embodiment, but En-Face images of OCTA to be displayed can be changed by the designation of an examiner. Thus, the change of images when the execution of image quality improvement processing is designated (the button 3420 is in the active state) will be described.

The change of images is performed using a user interface (not illustrated) (e.g., combo box). For example, when an examiner changes the type of an image from a surface layer to a choroid blood vessel network, the image quality improvement unit executes image quality improvement processing on a choroid blood vessel network image, and the display control unit 101-05 displays a high quality image generated by the image quality improvement unit, on the report screen. In other words, the display control unit 101-05 may change the display of a high quality image in a first depth range to the display of a high quality image in a second depth range different from the first depth range at least partially, in accordance with an instruction from an examiner. At this time, the display control unit 101-05 may change the display of the high quality image in the first depth range to the display of the high quality image in the second depth range, by the first depth range being changed to the second depth range in accordance with an instruction from an examiner. As described above, in a case where a high quality image has already been generated as for an image highly likely to be displayed when a screen transitions to the report screen, the display control unit 101-05 is only required to display the generated high quality image. A change method of the type of an image is not limited to the above-described method, and it is also possible to generate an En-Face image of OCTA with a different depth range set by changing a reference layer and an offset value. In this case, when a reference layer or an offset value is changed, the image quality improvement unit executes image quality improvement processing on an arbitrary En-Face image of OCTA, and the display control unit 101-05 displays a high quality image on the report screen. The change of a reference layer or an offset value can be performed using a user interface (not illustrated) (e.g., combo box or text box). In addition, by dragging any of the boundary lines 3413 and 3414 (moving a layer boundary) displayed with being superimposed on the tomographic images Im3411 and Im3412, a generation range of an En-Face image of OCTA can be changed. When a boundary line is changed by dragging, an execution command of image quality improvement processing is continuously executed. The image quality improvement unit may thereby constantly perform processing in response to the execution command, or may execute processing after a layer boundary is changed by dragging. Alternatively, an execution command of image quality improvement processing is continuously executed, but the last command may be canceled when a next command is issued and the most recent command may be executed. In some cases, image quality improvement processing takes a long time. Thus, even if a command is executed at any timing of the above-described timings, it sometimes takes a long time until a high quality image is displayed. In view of the foregoing, during a period from when a depth range for generating an En-Face image of OCTA is set in accordance with an instruction from an examiner, until a high quality image is displayed, an En-Face image of OCTA (low quality image) corresponding to the set depth range may be displayed. In other words, an En-Face image of OCTA (low quality image) corresponding to the set depth range may be displayed when the above-described depth range is set, and when image quality improvement processing ends, the display of the En-Face image of OCTA (the low quality image) may be changed to the display of a high quality image. Alternatively, information indicating that image quality improvement processing is being executed may be displayed during a period from when the above-described depth range is set until a high quality image is displayed. These can be applied not only to a case premised on a state in which execution of image quality improvement processing is already designated (button 3420 is in an active state), but also to a period until a high quality image is displayed when an execution instruction of image quality improvement processing is issued in accordance with an instruction from an examiner, for example.

In the present exemplary embodiment, the description has been given of an example in which the images Im3407 and Im3408 of different layers are displayed as En-Face images of OCTA, and a low quality image and a high quality image are switched to be displayed, but the configuration is not limited to this. For example, the images Im3407 and Im3408 may be adjacently displayed as a low quality En-Face image of OCTA and a high quality En-Face image of OCTA, respectively. In a case where the display of an image is switched, the image is switched at the same location, and thereby comparison of a changed portion can be easily performed. In a case where images are adjacently displayed, the images can be simultaneously displayed, and thus comparison of the entire images can be easily performed.

The analysis unit 101-46 may perform image analysis of a high quality image generated by image quality improvement processing. Image analysis of an En-Face image of OCTA of which image quality has been improved can detect, by applying arbitrary binarization processing, a location (blood vessel region) corresponding to blood vessels from the image. By obtaining a ratio of the detected location corresponding to blood vessels in the image, an area density can be analyzed. In addition, an image having a line width of one pixel can be obtained by thinning the location corresponding to blood vessels that has been subjected to binarization processing, and a ratio (also referred to as a skeleton density) of blood vessels that is independent of a thickness can also be obtained. Using these images, an area or a shape (e.g., degree of circularity) of an avascular region (FAZ) may be analyzed. The above-described numerical values may be calculated from the entire image as a method of analysis, or numerical values may be calculated for a designated region of interest (ROI) based on an instruction of an examiner (user) using a user interface (not illustrated). The setting of an ROI is not always designated by an examiner, and an automatically predetermined region may be designated. The above-described various parameters are examples of analysis results related to blood vessels, and parameters may be any parameters as long as the parameters are related to blood vessels. The analysis unit 101-46 may perform a plurality of types of image analysis processing. In other words, the description has been given of an example in which the analysis unit 101-46 analyzes an En-Face image of OCTA, but the analysis is not limited to this. The analysis unit 101-46 may simultaneously perform retinal layer segmentation, layer thickness measurement, head three-dimensional shape analysis, and cribriform plate analysis on an image acquired by an OCT. In relation to this, the analysis unit 101-46 may perform a part or all of a plurality of types of image analysis processing in accordance with an instruction issued from an examiner via an arbitrary input device.

At this time, the display control unit 101-05 displays a high quality image generated by the image quality improvement unit and an analysis result obtained by the analysis unit 101-46, on the display unit 104. The display control unit 101-05 may output a high quality image and an analysis result to separate display units or devices. The display control unit 101-05 may also display only an analysis result on the display unit 104. Furthermore, in a case where the analysis unit 101-46 outputs a plurality of analysis results, the display control unit 101-05 may output a part or all of the plurality of analysis results to the display unit 104 or another device. For example, the display control unit 101-05 may display an analysis result related to blood vessels in an En-Face image of OCTA on the display unit 104 as a two-dimensional map. The display control unit 101-05 may also display a value indicating an analysis result related to blood vessels in an En-Face image of OCTA, on the display unit 104 with being superimposed on the En-Face image of OCTA. In this manner, a high quality image is used for image analysis in the image processing apparatus 101 according to the present exemplary embodiment, the accuracy of analysis can thereby be improved.

The execution of image quality improvement processing in screen transition will now be described with reference to FIGS. 14A and 14B. FIG. 14B illustrates a screen example displaying an OCTA image illustrated in FIG. 14A in an enlarged manner. In FIG. 14B, the button 3420 is also displayed similarly to FIG. 14A. The screen illustrated in FIG. 14A transitions to the screen in FIG. 14B by, for example, double-clicking the OCTA image. The screen illustrated in FIG. 14B transitions to the screen in FIG. 14A by pressing a close button 3430. The screen transition method is not limited the method described here, and a user interface (not illustrated) may be used.

In a case where the execution of image quality improvement processing is designated (the button 3420 is in an active state) when a screen transitions, the state is maintained also in screen transition. More specifically, in a case where the screen transitions to the screen illustrated in FIG. 14A in a state in which a high quality image is displayed on the screen in FIG. 14B, a high quality image is displayed also on the screen illustrated in FIG. 14A. The button 3420 is then set to an active state. The same applies to a case where the screen in FIG. 14A transitions to the screen in FIG. 14B. The display can also be switched to a low quality image by designating the button 3420 on the screen in FIG. 14A.

Figure 14B:
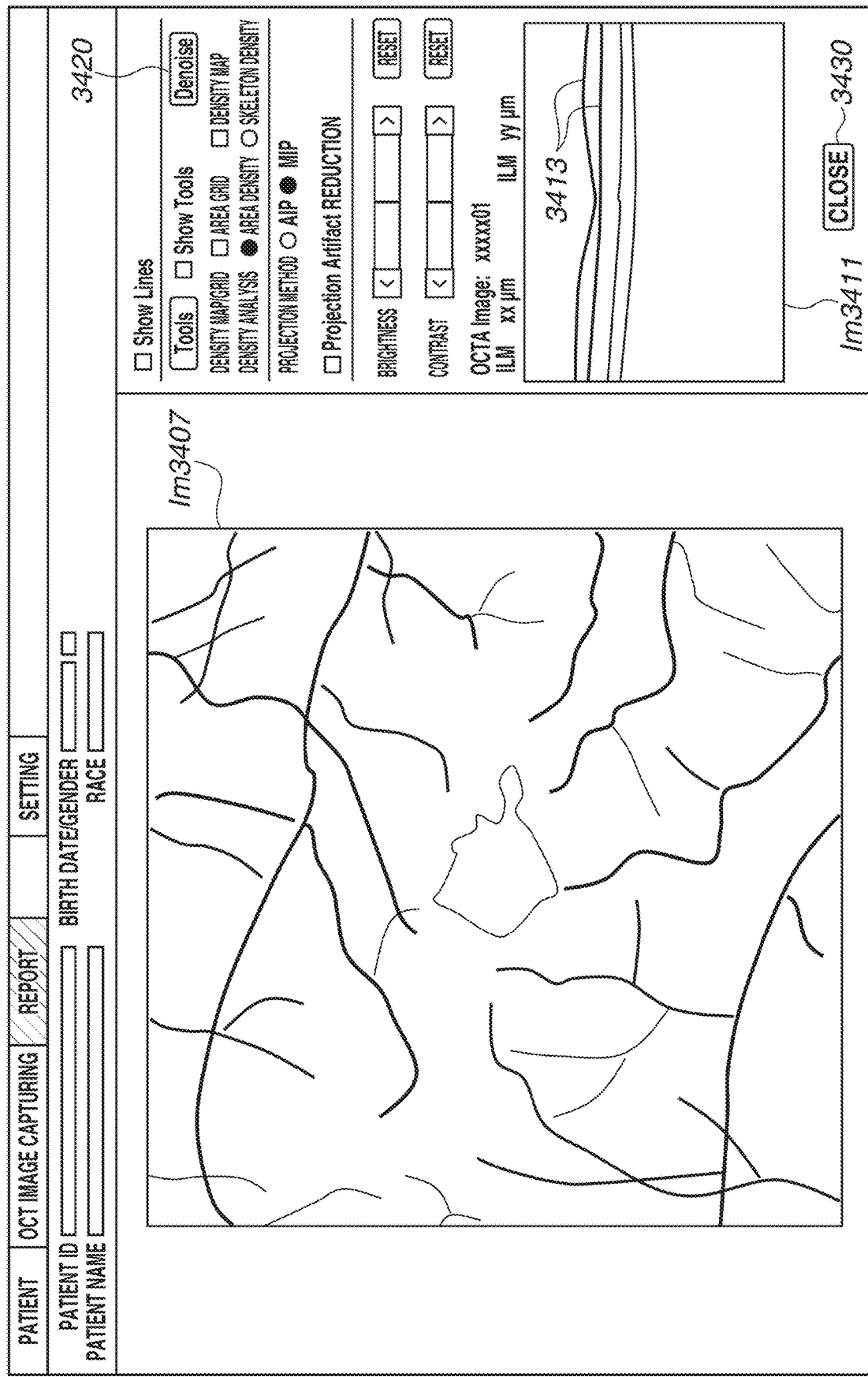
FIG. 14B illustrates an example of a user interface according to the fifth exemplary embodiment.

Screen transition is not limited to the screens illustrated in FIGS. 14A and 14B. The screen transitions, while maintaining a display state of a high quality image, as long as the screen transition is to a screen displaying the same image capturing data, such as a display screen for follow-up or a panorama display screen. In other words, an image corresponding to the state of the button 3420 on a display screen before transition is displayed on a display screen after transition. For example, if the button 3420 is in an active state on a display screen before transition, a high quality image is displayed on a display screen after transition. For example, if the active state of the button 3420 is canceled on a display screen before transition, a low quality image is displayed on a display screen after transition. If the button 3420 enters an active state on the display screen for follow-up, a plurality of images obtained on different dates and times (different inspection days) that is adjacently displayed on the display screen for follow-up may be switched to high quality images. In other words, if the button 3420 enters an active state on the display screen for follow-up, the active state may be entirely reflected in a plurality of images obtained on different dates and times.

Figure 11:
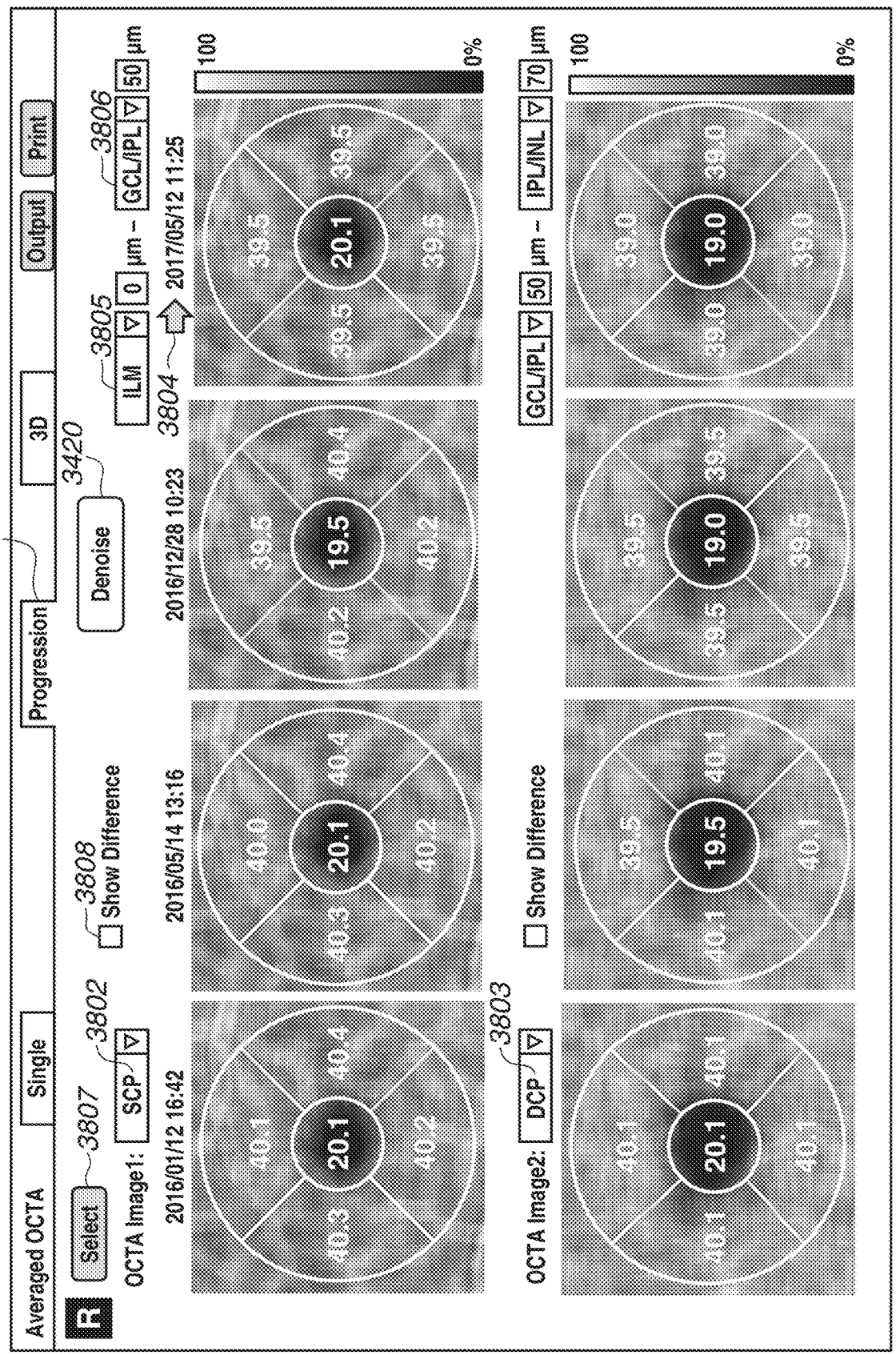
FIG. 11 illustrates an example of a user interface according to a fifth exemplary embodiment.

FIG. 11 illustrates an example of the display screen for follow-up. If a tab 3801 is selected in accordance with an instruction from an examiner, the display screen for follow-up is displayed as illustrated in FIG. 11. At this time, depth ranges can be changed by the examiner selecting depth ranges of a measurement target region from predetermined depth range sets (3802 and 3803) displayed in list boxes. For example, a retina surface layer is selected in the list box 3802, and a retina deep layer is selected in the list box 3803. An analysis result of a motion contrast image of the retina surface layer is displayed in an upper display region, and an analysis result of a motion contrast image of the retina deep layer is displayed in a lower display region. In other words, when a depth range is selected, the display of a plurality of images obtained on different dates and times is collectively changed to parallel display of analysis results of a plurality of motion contrast images in the selected depth range.

At this time, if the display of analysis results is set to an unselected state, the display may be collectively changed to parallel display of a plurality of motion contrast images obtained on different dates and times. If the button 3420 is designated in accordance with an instruction from an examiner, the display of a plurality of motion contrast images is collectively changed to the display of a plurality of high quality images.

In a case where the display of analysis results is in a selected state, when the button 3420 is designated in accordance with an instruction from an examiner, the display of analysis results of a plurality of motion contrast images is collectively changed to the display of analysis results of a plurality of high quality images. The display of analysis results may be superimpose display of analysis results on images at an arbitrary transparency. At this time, the change to the display of analysis results may be, for example, the change to a state in which analysis results are superimposed on displayed images with an arbitrary transparency. In addition, the change to the display of analysis results may be, for example, the change to the display of images (e.g., two-dimensional map) obtained by performing blend processing of analysis results and images at an arbitrary transparency.

A type and an offset position of a layer boundary to be used for designation of a depth range can collectively be changed from a user interface such as user interfaces 3805 and 3806. By displaying tomographic images together, and moving layer boundary data superimposed on the tomographic images in accordance with an instruction from an examiner, depth ranges of a plurality of motion contrast images obtained on different dates and times may be entirely changed. At this time, layer boundary data may be similarly moved also on the other tomographic images, if a plurality of tomographic images obtained on different dates and times is adjacently displayed and the above-described movement is performed on one tomographic image. An image projection method and the presence or absence of projection artifact suppression processing may be changed, for example, by making a selection from a user interface, such as a context menu. A selection screen may also be displayed by selecting a selection button 3807, and an image selected from an image list displayed on the selection screen may be displayed. An arrow 3804 displayed in an upper part in FIG. 11 is a mark indicating a currently-selected inspection, and a reference inspection (baseline) is an inspection (leftmost image in FIG. 11) selected in follow-up image capturing. A mark indicating a reference inspection may also be displayed on the display unit 104.

In a case where a "Show Difference" checkbox 3808 is designated, a measured value distribution (map or sector map) for a reference image is displayed on the reference image. In this case, a difference measured value map is displayed. The difference measured value map is based on a difference between a measured value distribution calculated for a reference image in a region corresponding to other inspection days, and a measurement distribution calculated for an image displayed in the region. As a measurement result, a trend graph (graph of measured values for images on the respective inspection days obtained by temporal change measurement) may be displayed on the report screen. In other words, time-series data (e.g., time-series graph) of a plurality of analysis results corresponding to a plurality of images obtained on different dates and times may be displayed. At this time, analysis results related to dates and times other than a plurality of dates and times corresponding to a plurality of displayed images may also be displayed as time-series data in a state of being distinguishable from a plurality of analysis results corresponding to the plurality of displayed images (e.g., the color of each point on the time-series graph varies depending on the presence or absence of the display of an image). A regression line (curve) of the trend graph and a corresponding formula may also be displayed on the report screen.

In the present exemplary embodiment, a motion contrast image has been described, but the present exemplary embodiment is not limited to the motion contrast image. An image related to processing according to the present exemplary embodiment, such as display, image quality improvement, and image analysis, may be a tomographic image. Furthermore, the image is not limited to a tomographic image, and may be a different image, such as an SLO image, a fundus photograph, or a fluorescein fundus photograph. In this case, a user interface for executing image quality improvement processing may include a user interface for designating execution of image quality improvement processing for a plurality of images of different types, and a user interface for selecting an arbitrary image from a plurality of images of different types and designating execution of image quality improvement processing.

With such a configuration, the display control unit 101-05 can display an image processed by the image quality improvement unit (not illustrated) according to the present exemplary embodiment, on the display unit 104. At this time, as described above, in a case where the display of high quality images, the display of analysis results, or at least one of a plurality of conditions related to a depth range of a front image to be displayed is in a selected state, the selected state may be maintained even if a display screen transitions.

In addition, in a case where at least one of the plurality of conditions is in the selected state, the selected state of the at least one condition may be maintained even if the state is changed to a state in which another condition is selected, as described above. For example, in a case where the display of analysis results is in the selected state, the display control unit 101-05 may change the display of analysis results of low quality images to the display of analysis results of high quality images in accordance with an instruction from an examiner (e.g., if the button 3420 is designated). In a case where the display of analysis results is in the selected state, the display control unit 101-05 may change the display of analysis results of high quality images to the display of analysis results of low quality images in accordance with an instruction from an examiner (e.g., if the designation of the button 3420 is canceled).

In a case where the display of high quality images is in an unselected state, the display control unit 101-05 may change the display of analysis results of low quality images to the display of low quality images in accordance with an instruction from an examiner (e.g., if the designation of the display of analysis results is canceled). In a case where the display of high quality images is in an unselected state, the display control unit 101-05 may change the display of low quality images to the display of analysis results of low quality images in accordance with an instruction from an examiner (e.g., if the display of analysis results is designated). In a case where the display of high quality images is in the selected state, the display control unit 101-05 may change the display of analysis results of high quality images to the display of high quality images in accordance with an instruction from an examiner (e.g., if the designation of the display of analysis results is canceled). In a case where the display of high quality images is in the selected state, the display control unit 101-05 may change the display of high quality images to the display of analysis results of high quality images in accordance with an instruction from an examiner (e.g., if the display of analysis results is designated).

A case will be considered where the display of high quality images is in the unselected state and the display of analysis results of a first type is in the selected state. In this case, the display control unit 101-05 may change the display of analysis results of the first type of low quality images to the display of analysis results of a second type of low quality images in accordance with an instruction from an examiner (e.g., if the display of analysis results of the second type is designated). A case will be considered where the display of high quality images is in the selected state and the display of analysis results of the first type is in the selected state. In this case, the display control unit 101-05 may change the display of analysis results of the first type of high quality images to the display of analysis results of the second type of high quality images in accordance with an instruction from an examiner (e.g., if the display of analysis results of the second type is designated).

In the display screen for follow-up, such these display changes may be entirely reflected in a plurality of images obtained on different dates and times, as described above. The display of analysis results may be superimpose display of analysis results on images at an arbitrary transparency. The display of analysis results may be superimpose display of analysis results on images at an arbitrary transparency. At this time, the change to the display of analysis results may be the change to a state in which analysis results are superimposed on displayed images at an arbitrary transparency, for example. The change to the display of analysis results may be, for example, the change to the display of images (e.g., two-dimensional map) obtained by performing blend processing of analysis results and images with an arbitrary transparency.

Modified Example 1

In the above-described exemplary embodiment, the display control unit 101-05 can display, on the display unit 104, an image selected in accordance with an instruction from an examiner from among high quality images generated by the image quality improvement unit and an input image. The display control unit 101-05 may also switch the display on the display unit 104 from a captured image (input image) to a high quality image in accordance with an instruction from an examiner. In other words, the display control unit 101-05 may change the display of low quality images to the display of high quality images in accordance with an instruction from an examiner. In addition, the display control unit 101-05 may change the display of high quality images to the display of low quality images in accordance with an instruction from an examiner.

Furthermore, the image quality improvement unit in the image processing apparatus 101 (or the image processing unit 101-04) may execute a start (input of an image to the image quality improvement engine) of image quality improvement processing performed by the image quality improvement engine (learned model for image quality improvement), in accordance with an instruction from an examiner, and the display control unit 101-05 may display a high quality image generated by the image quality improvement unit, on the display unit 104. In contrast to this, if an input image is captured by an image capturing apparatus (the tomographic image capturing apparatus 100), the image quality improvement engine may automatically generate a high quality image based on the input image, and the display control unit 101-05 may display the high quality image on the display unit 104 in accordance with an instruction from an examiner. The image quality improvement engine includes a learned model that performs the above-described image quality enhancement processing (image quality improvement processing).

These types of processing can be similarly performed also for an output of analysis results. In other words, the display control unit 101-05 may change the display of analysis results of low quality images to the display of analysis results of high quality images in accordance with an instruction from an examiner. In addition, the display control unit 101-05 may change the display of analysis results of high quality images to the display of analysis results of low quality images in accordance with an instruction from an examiner. The display control unit 101-05 may also change the display of analysis results of low quality images to the display of low quality images in accordance with an instruction from an examiner. The display control unit 101-05 may also change the display of low quality images to the display of analysis results of low quality images in accordance with an instruction from an examiner. The display control unit 101-05 may also change the display of analysis results of high quality images to the display of high quality images in accordance with an instruction from an examiner. The display control unit 101-05 may also change the display of high quality images to the display of analysis results of high quality images in accordance with an instruction from an examiner.

The display control unit 101-05 may also change the display of analysis results of low quality images to the display of analysis results of another type of low quality images in accordance with an instruction from an examiner. The display control unit 101-05 may also change the display of analysis results of high quality images to the display of analysis results of another type of high quality images in accordance with an instruction from an examiner.

The display of analysis results of high quality images may be superimpose display of analysis results of high quality images on the high quality images at an arbitrary transparency. The display of analysis results of low quality images may also be superimpose display of analysis results of low quality images on the low quality images at an arbitrary transparency. At this time, the change to the display of analysis results may be, for example, the change to a state in which analysis results are superimposed on displayed images at an arbitrary transparency. The change to the display of analysis results may also be, for example, the change to the display of images (e.g., two-dimensional map) obtained by performing blend processing of analysis results and images with an arbitrary transparency.

In the above-described various exemplary embodiments, processing to be executed on a set region of interest is not limited to analysis processing, and may be, for example, image processing. The image processing may be any image processing, such as contrast processing, gradation conversion processing, super-resolution processing, or smoothing processing. Even after a display screen transitions to another display screen, a blend image obtained by performing blend processing with a transmissivity set before transition may be displayed. For example, a plurality of blend images obtained by performing blend processing at a transmissivity set before transition may be adjacently displayed as a plurality of images obtained on different dates and times, after a display screen transitions to the display screen for follow-up. Furthermore, when a similar slide bar is displayed on the display screen for follow-up, and a transmissivity is set (changed) in accordance with an instruction from an examiner, the set transmissivity may be collectively reflected on a plurality of images obtained on different dates and times. In other words, if a transmissivity is set (changed), a plurality of blend images obtained by performing blend processing at the set transmissivity may be displayed. Screens on which the blend processing is executable are not limited to these display screens. The blend processing is only required to be executable on at least one display screen of the image capturing confirmation screen, the report screen, and a preview screen for various types of adjustment before image capturing (display screen on which various live moving images are displayed).

Modified Example 2

In the above-described various exemplary embodiments and the modified example, a transmissivity (transmission coefficient) to be used in blend processing needs not be always set in accordance with an instruction from an examiner, and may be automatically set, or may be semi-automatically set. For example, a learned model obtained by performing machine learning using learning data may be used; in the learning data, a medical image, such as at least one of an OCT image and an OCTA image of mutually corresponding regions, is set as input data, and a transmissivity set in accordance with an instruction from an examiner is set as correct data (teaching data). In other words, a transmissivity setting unit may be configured to generate a new transmissivity using the above-described learned model from a medical image such as at least one of an OCT image and an OCTA image of mutually corresponding regions. At this time, the above-described learned model may be, for example, a learned model obtained by additionally performing learning using learning data in which a transmissivity determined (changed) in accordance with an instruction from an examiner is set as correct data. The above-described learned model may be, for example, a learned model obtained by additionally performing learning using learning data in which a transmissivity changed from the new transmissivity (transmissivity obtained using a learned model) in accordance with an instruction from an examiner is set as correct data. With this configuration, it is possible to acquire, for example, a new transmissivity to be set in consideration of the tendency of a transmissivity desired by an examiner for a medical image. In other words, it is possible to accurately form a transmissivity setting unit customized by an examiner. It is thereby possible to enhance diagnosis efficiency of an examiner. An OCT image and an OCTA image of mutually corresponding regions may be, for example, images obtained by using at least part of a common interference signal.

The above-described learned model can be obtained by machine learning that uses learning data. The machine learning includes, for example, deep learning including a multi-hierarchical neural network. At least in part of the multi-hierarchical neural network, for example, a convolutional neural network (CNN) can be used as a machine learning model. Furthermore, at least in part of the multi-hierarchical neural network, a technique related to an autoencoder may be used. In addition, a technique related to back propagation may be used for learning. Nevertheless, the machine learning is not limited to deep learning, and may be any learning as long as the learning uses a model that can extract (represent) a feature amount of learning such as images, by performing learning for the model itself. In addition, a learned model is a model preliminarily trained (learned) using appropriate learning data for a machine learning model that is based on an arbitrary machine learning algorithm. Nevertheless, further learning of a learned model is not prohibited, and additional learning can also be performed. In addition, learning data includes a pair of input data and output data (correct data). While learning data is referred to as teaching data in some cases, correct data is referred to as teaching data in other cases. In addition, a learned model may be customized as a model suitable for, for example, an operator, by being updated by additional learning. A learned model in this modified example is not limited to a learned model obtained by additionally performing learning, and may be any learned model as long as the learned model is obtained by performing learning using learning data including a medical image and information regarding a transmissivity.

The above-described learned model may be a learned model obtained by performing learning using learning data including input data having a set of a plurality of medical images of different types of a predetermined region of a subject. At this time, examples of the input data included in the learning data include input data having a set of a motion contrast front image of a fundus and a brightness front image (or brightness tomographic image), and input data having a set of a tomographic image (B scan image) of a fundus and a color fundus image (or fluorescein fundus image). A plurality of medical images of the different types may be any medical images as long as the medical images are acquired by different modalities, different optical systems, or different principles. The above-described learned model may be a learned model obtained by performing learning using learning data including input data having a set of a plurality of medical images of different regions of the subject. At this time, examples of the input data included in the learning data include input data having a set of a tomographic image (B scan image) of a fundus and a tomographic image (B scan image) of an anterior eye segment, and input data having a set of a three-dimensional OCT image of a macula of a fundus and a circular scan (or raster scan) tomographic image of an optive nerve head of a fundus. Input data included in the learning data may be a plurality of medical images of different regions of a subject and different types. At this time, examples of the input data included in the learning data include input data having a set of a tomographic image of an anterior eye segment and color fundus image. The above-described learned model may be a learned model obtained by performing learning using learning data including input data having a set of a plurality of medical images at different image capturing field angles of a predetermined region of a subject. The input data included in the learning data may be an image obtained by combining a plurality of medical images obtained by time-dividing a predetermined region into a plurality of regions, like a panoramic image. The input data included in the learning data may be input data having a set of a plurality of medical images of a predetermined region of a subject obtained on different dates and times.

A transmissivity may be made changeable in accordance with an instruction from an examiner, from a default setting of a new transmissivity obtained using the above-described learned model. Furthermore, whether to use the changed transmissivity as learning data for additional learning may be made selectable in accordance with an instruction from an examiner. In addition, by an ROI being set on a blend image, the use of a transmissivity set (changed) when the ROI is set, as learning data for additional learning, may be selected in tandem with the setting.

Modified Example 3

The display control unit 101-05 in the above-described various exemplary embodiments and modified examples may display analysis results, such as a layer thickness of a desired layer and various blood vessel densities, on a report screen of a display screen. The display control unit 101-05 may also display, as an analysis result, a value (distribution) of a parameter related to a target region including at least one of the following portions: an optive nerve head portion, a macular region, a blood vessel region, a band of nerve fibers, a vitreum region, a macula region, a choroid region, a scleral region, a cribriform plate region, a retinal layer boundary, a retinal layer boundary end portion, a visual cell, a blood cell, a blood vessel wall, blood vessel inner wall boundary, a blood vessel outside boundary, a ganglion cell, a corneal region, an angle region, and a canal of Schlemm. At this time, by analyzing, for example, a medical image to which reduction processing of various artifacts is applied, it is possible to display an accurate analysis result. The artifact may be, for example, a pseudo image region generated by optical absorption caused by a blood vessel region, a projection artifact, or a belt-like artifact in a front image generated in the main scanning direction of measurement light depending on the state (e.g., motion, eyewink) of a subject's eye. The artifact may be any artifact as long as the artifact is, for example, an image capturing failure region generated at random on a medical image of a predetermined region of a subject each time image capturing is performed. In addition, a value (distribution) of a parameter related to a region including at least one of the above-described various artifacts (image capturing failure regions) may be displayed as an analysis result. In addition, a value (distribution) of a parameter related to a region including at least one of abnormal regions, such as drusen, a neovascular vessel, achromoderma (hard exudate), or a pseudo drusen, may be displayed as an analysis result.

The analysis result may be displayed by an analysis map or a sector indicating a statistical value corresponding to each divided region. The analysis result may be an analysis result generated using a learned model obtained by performing learning using an analysis result of a medical image as learning data (analysis result generation engine, a learned model for analysis result generation). At this time, the learned model may be a learned model obtained by learning that uses learning data including a medical image and an analysis result of the medical image, or learning data including a medical image and an analysis result of a medical image of a type different from the medical image. In addition, the learned model may be a learned model obtained by learning that uses learning data including input data having a set of a plurality of medical images of different types of a predetermined region, such as a brightness front image and a motion contrast front image. The brightness front image corresponds to an En-Face image of a tomographic image, and the motion contrast front image corresponds to an En-Face image of OCTA. In addition, an analysis result obtained using a high quality image generated by a learned model for image quality improvement may be displayed. The learned model for image quality improvement may be a learned model obtained by performing learning of learning data in which the first image is set as input data, and the second image having higher image quality than the first image is set as correct data. At this time, the second image may be a high quality image on which contrast improvement or noise reduction is performed by, for example, overlay processing of a plurality of first images (e.g., averaging processing of a plurality of first images obtained by performing position alignment).

Input data included in learning data may be a high quality image generated by the learned model for image quality improvement, or may be a set of a low quality image and a high quality image. The learning data may be data obtained by labeling (annotating) input data with information including at least one of, for example, an analysis value (e.g., average value, median value) obtained by analyzing an analysis region, a table including an analysis value, an analysis map, and a position of an analysis region such as a sector in an image, as correct data (of supervised learning). An analysis result obtained by a learned model for analysis result generation may be displayed in accordance with an instruction from an examiner. For example, the image processing unit 101-04 can generate, from at least one medical image of a plurality of medical images to be subjected to blend processing, an image analysis result related to the at least one medical image, using the learned model for analysis result generation (different from the learned model for image quality improvement). In addition, for example, the display control unit 101-05 can display an image analysis result obtained from the above-described at least one medical image using the learned model for analysis result generation, on the display unit 104.

The display control unit 101-05 in the above-described various exemplary embodiments and modified examples may display various diagnosis results, such as glaucoma or age-related macular degeneration, on a report screen of a display screen. At this time, by analyzing, for example, a medical image to which reduction processing of the above-described various artifacts is applied, it is possible to display an accurate diagnosis result. As the diagnosis result, a position of an identified abnormal region may be displayed on an image, or the state of the abnormal region may be displayed by characters. In addition, a classification result (e.g., Curtin classification) of an abnormal region may be displayed as the diagnosis result. As the classification result, information indicating, for example, a likelihood of each abnormal region (e.g., a numerical value indicating a percentage), may be displayed. Alternatively, information necessary for a doctor confirming diagnosis may be displayed as the diagnosis result. As the above-described necessary information, for example, an advice, such as additional image capturing, can be considered. For example, in a case where an abnormal region is detected in a blood vessel region in an OCTA image, it may be displayed that fluorescein image capturing that uses contrast agent and can observe blood vessels more minutely than an OCTA is to be additionally performed.

A diagnosis result may be generated using a learned model (diagnosis result generation engine, learned model for diagnosis result generation) obtained by learning using a diagnosis result of a medical image as learning data. The learned model may be a learned model obtained by learning that uses learning data including a medical image and a diagnosis result of the medical image, or learning data including a medical image and a diagnosis result of a medical image of a type different from the medical image. In addition, a diagnosis result obtained by using a high quality image generated by the learned model for image quality improvement may be displayed. For example, the image processing unit 101-04 can generate, from at least one medical image of a plurality of medical images to be subjected to blend processing, a diagnosis result related to the at least one medical image, using the learned model for diagnosis result generation (different from the learned model for image quality improvement). Furthermore, the display control unit 101-05 can display, for example, a diagnosis result obtained from the above-described at least one medical image using the learned model for generating diagnosis results, on the display unit 104.

Input data included in the learning data may be a high quality image generated by the learned model for image quality improvement, or may be a set of a low quality image and a high quality image. In addition, the learning data may be data obtained by labeling (annotating) input data with information including, for example, at least one of a diagnosis name, a type or a state (degree) of a lesion (abnormal region), a position of a lesion in an image, a position of a lesion with respect to a target region, findings (interpretation findings), a basis for diagnosis name (e.g., positive medical support information, etc.), and a basis for denying a diagnosis name (e.g., negative medical support information), as correct data (of supervised learning). A diagnosis result obtained by the learned model for diagnosis result generation may be displayed in accordance with an instruction from an examiner.

The display control unit 101-05 in the above-described various exemplary embodiments and modified examples may display an object recognition result (object detection result) or a segmentation result of the above-described target region, an artifact, or an abnormal region on a report screen of a display screen. At this time, for example, a rectangular frame may be displayed near an object on an image in a superimposed manner. Alternatively, for example, color may be displayed an object in an image in a superimposed manner. The object recognition result or the segmentation result may be a result generated using a learned model (object recognition engine, learned model for object recognition, segmentation engine, learned model for segmentation) obtained by performing learning using learning data obtained by labeling (annotating) a medical image with information indicating object recognition or segmentation, as correct data. The above-described analysis result generation or diagnosis result generation may be obtained by using the above-described object recognition result or segmentation result. For example, processing of analysis result generation or diagnosis result generation may be performed on a target region obtained by processing of object recognition or segmentation.

In a case where an abnormal region is detected, the image processing unit 101-04 may use a generative adversarial network (GAN) or a variational auto-encoder (VAE). For example, a deep convolutional GAN (DCGAN) including a generator obtained by learning generation of a tomographic image, and a discriminator obtained by learning discrimination between a new tomographic image generated by the generator and a real fundus front image can be used as a machine learning model.

In the case of using the DCGAN, for example, a latent variable is obtained by the discriminator encoding an input tomographic image, and the generator generates a new tomographic image based on the latent variable. Thereafter, a difference between the input tomographic image and the generated new tomographic image can be extracted as an abnormal region. In the case of using the VAE, for example, a latent variable is obtained by an encoder encoding an input tomographic image, and a new tomographic image is generated by a decoder decoding the latent variable. Thereafter, a difference between the input tomographic image and the generated new tomographic image can be extracted as an abnormal region. A tomographic image has been described as an example of input data, but a fundus image or a front image of an anterior eye may also be used.

Furthermore, the image processing unit 101-04 may detect an abnormal region using a convolutional auto-encoder (CAE). In the case of using the CAE, the same image is learned as input data and output data at the time of learning. With this configuration, if an image having an abnormal region at the time of estimation is input, an image without an abnormal region is output in accordance with the tendency of learning. After that, a difference between an image input to the CAE and an image output from the CAE can be extracted as an abnormal region. In addition, in this case, not only a tomographic image but also a fundus image and a front image of an anterior eye may be used as the input data.

In these cases, the image processing unit 101-04 can generate information regarding a difference between a medical image obtained using a generative adversarial network or an auto-encoder for each of different regions identified by segmentation processing, and a medical image input to the generative adversarial network or auto-encoder, as information regarding an abnormal region. With this configuration, the image processing unit 101-04 can be expected to quickly and accurately detect an abnormal region. The auto-encoder includes, for example, the VAE and the CAE. For example, the image processing unit 101-04 can generate, as information regarding an abnormal region, information regarding a difference between a medical image obtained from at least one medical image of a plurality of medical images to be subjected to blend processing, using a generative adversarial network or an auto-encoder, and the at least one medical image. In addition, for example, the display control unit 101-05 can display, as information regarding an abnormal region, information regarding a difference between a medical image obtained from the above-described at least one medical image using the generative adversarial network or the auto-encoder, and the at least one medical image, on the display unit 104.

In a case of a diseased eye, an image feature varies depending on the type of disease. Thus, a learned model used in the above-described various exemplary embodiments and modified examples may be generated or prepared for each type of disease or for each abnormal region. In this case, the image processing apparatus 101 can select, for example, a learned model to be used for processing, in accordance with an input (instruction) of the type of disease of a subject's eye or an abnormal region from an operator. A learned model prepared for each type of disease or for each abnormal region is not limited to a learned model to be used for detection of a retinal layer or generation of a region label image, and may be, for example, a learned model to be used by an engine for image evaluation or an engine for analysis. At this time, the image processing apparatus 101 may identify the type of disease of a subject's eye or an abnormal region from an image, using a separately-prepared learned model. In this case, the image processing apparatus 101 can automatically select a learned model to be used for the above-described processing, based on the type of disease or an abnormal region that has been identified using the separately-prepared learned model. The learned model for identifying the type of disease or an abnormal region of a subject's eye may perform learning using a pair of learning data in which a tomographic image or fundus image is set as input data, and the type of disease or an abnormal region in these images is set as output data. As input data of learning data, a tomographic image or a fundus image may be solely set as the input data, or a combination of these may be set as the input data.

In particular, the learned model for diagnosis result generation may be a learned model obtained by learning with learning data including input data having a set of a plurality of medical images of different types of a predetermined region of a subject. At this time, for example, input data including a set of a motion contrast front image of a fundus and a brightness front image (or brightness tomographic image) can be considered as the input data included in the learning data. Furthermore, for example, input data including a set of a tomographic image (B scan image) of a fundus and a color fundus image (or fluorescein fundus image) can also be considered as the input data included in the learning data. The plurality of medical images of different types may be any medical images as long as the medical images are acquired by different modalities, different optical systems, or different principles.

In particular, the learned model for diagnosis result generation may be a learned model obtained by learning with learning data including input data having a set of a plurality of medical images of different regions of a subject. At this time, for example, input data including a set of a tomographic image (B scan image) of a fundus and a tomographic image (B scan image) of an anterior eye segment can be considered as the input data included in the learning data. Furthermore, input data including a set of a three-dimensional OCT image (three-dimensional tomographic image) of a macula of a fundus and a circular scan (or raster scan) tomographic image of an optive nerve head of a fundus can also be considered as the input data included in the learning data.

Input data included in learning data may be a plurality of medical images of different regions of a subject and different types. At this time, for example, input data including a set of a tomographic image of an anterior eye segment and color fundus image can be considered as the input data included in the learning data, for example. The above-described learned model may be a learned model obtained by learning with learning data including input data having a set of a plurality of medical images at different image capturing field angles of a predetermined region of a subject. Input data included in the learning data may be an image obtained by combining a plurality of medical images obtained by time-dividing a predetermined region into a plurality of regions, like a panoramic image. At this time, by using a wide field angle image such as a panoramic image as the learning data, there is a possibility that a feature amount of an image can be accurately acquired for the reason that an information amount is larger than a narrow field angle image. Thus, a result of each piece of processing can be improved. For example, in a case where abnormal regions are detected at a plurality of positions in a wide field angle image at the time of estimation (at the time of prediction), enlarged images of the respective abnormal regions are sequentially displayable. With this configuration, abnormal regions at a plurality of positions can be efficiency checked, and thus, for example, the convenience of an examiner can be enhanced. At this time, for example, each position on a wide field angle image in which an abnormal region is detected may be selectable by an examiner, and an enlarged image of an abnormal region at the selected position may be displayed. The input data included in the learning data may be input data having a set of a plurality of medical images of a predetermined region of a subject obtained on different dates and times.

A display screen on which at least one result of the above-described analysis result, diagnosis result, object recognition result, and segmentation result is displayed is not limited to the report screen. Such a display screen may be displayed on at least one display screen of, for example, the image capturing confirmation screen, the display screen for follow-up, and the preview screen for various types of adjustment before image capturing (display screen on which various live moving images are displayed). For example, by displaying the above-described at least one result obtained using the above-described learned model on the image capturing confirmation screen, an examiner can checks an accurate result even immediately after image capturing. The above-described change in display between low quality images and high quality images may be a change in display between analysis results of low quality images and analysis results of high quality images, for example.

The above-described various learned models can be obtained by machine learning that uses learning data. Type of machine learning include, for example, deep learning consisting of a multi-hierarchical neural network. In at least part of the multi-hierarchical neural network, for example, a convolutional neural network (CNN) can be used as a machine learning model. In at least part of the multi-hierarchical neural network, a technique related to an autoencoder may be used. A technique related to back propagation may also be used for learning. Nevertheless, the machine learning is not limited to deep learning, and may be any learning as long as the learning uses a model that can extract (represent) a feature amount of learning data such as images, by performing learning by the model itself. The machine learning model refers to a learning model that is based on a machine learning algorithm such as deep learning. The learned model is a model preliminarily trained (learned) using appropriate learning data for a machine learning model that is based on an arbitrary machine learning algorithm. Nevertheless, further learning of the learned model is not prohibited, and additional learning can also be performed. The learning data constitutes a pair of input data and output data (correct data). While learning data is referred to as teaching data in some cases, correct data is referred to as teaching data in other cases.

A GPU can perform efficient calculation by concurrently processing a larger amount of data. It is thus effective to perform processing using a GPU, in a case of performing learning a plurality of times using a learning model such as deep learning. In view of the foregoing, a GPU is used in this modified example in addition to a CPU in processing to be performed by the image processing unit 101-04 serving as an example of a learning unit (not illustrated). Specifically, in the case of executing a learning program including a learning model, learning is performed by the CPU and the GPU calculating in a cooperated manner. In the processing of the learning unit, calculation may be performed only by the CPU or the GPU. A processing unit (estimation unit) that executes processing that uses the above-described various learned models may use a GPU similarly to the learning unit. The learning unit may include an error detection unit (not illustrated) and an update unit (not illustrated). The error detection unit obtains an error between correct data and output data output from an output layer of a neural network in accordance with input data input to an input layer. The error detection unit may calculate an error between correct data and output data from a neural network, using a loss function. The update unit updates, for example, an internode connection weighting coefficient of the neural network in such a manner that the error becomes small, based on the error obtained by the error detection unit. The update unit updates a connection weighting coefficient using, for example, a backpropagation. The backpropagation is a method of adjusting an internode connection weighting coefficient of each neural network such that the above-described error becomes small.

As a machine learning model used for image quality improvement or segmentation, a U-net type machine learning model can be applied. The U-net type machine learning model has a function of an encoder including a plurality of hierarchies including a plurality of downsampling layers, and a function of a decoder including a plurality of hierarchies including a plurality of upsampling layers. In the U-net type machine learning model, position information (space information) obscured in the plurality of hierarchies formed as the encoder is made usable (e.g., using skip connection) in hierarchies (mutually corresponding hierarchies) of the same dimension of the plurality of hierarchies formed as the decoder.

A machine learning model used for, for example, image quality improvement or segmentation can use, for example, a Fully Convolutional Network (FCN) or SegNet. The machine learning model can also use a machine learning model that performs object recognition for each region in accordance with a desired configuration. The machine learning model that performs object recognition can use, for example, a Region CNN (RCNN), fast RCNN, or faster RCNN. A machine learning model that performs object recognition for each region can also use You Only Look Once (YOLO), or Single Shot Detector or Single Shot MultiBox Detector (SSD).

The machine learning model may be, for example, a capsule network (CapsNet). In a typical neural network, each unit (each neuron) is configured to output a scalar value, and thereby space information regarding, for example, a spatial positional relationship (relative position) between features in an image is reduced. With this configuration, learning can be performed in such a manner as to reduce, for example, the influence of local distortion or a parallel movement of an image. In contrast, in the capsule network, space information is configured to be held by each unit (each capsule) being configured to output space information as a vector, for example. With this configuration, learning can be performed in consideration of, for example, a spatial positional relationship between features in an image.

The image quality improvement engine (the learned model for image quality improvement) may be a learned model obtained by additionally learning using learning data including at least one high quality image generated by the image quality improvement engine. At this time, whether to use a high quality image as learning data for additional learning may be made selectable by an instruction from an examiner. The application of these configurations is not limited to the learned model for image quality improvement, and these configurations can also be applied to the above-described various learned models. In the generation of correct data used for learning of the above-described various learned models, a learned model for correct data generation for generating correct data, such as labeling (annotation), may be used. At this time, the learned model for correct data generation may be a learned model obtained by additionally (sequentially) learning correct data obtained by an examiner performing labeling (annotation). In other words, the learned model for correct data generation may be a learned model obtained by performing additional learning of learning data in which unlabeled data is set as input data and labeled data is set as output data. In a plurality of consecutive frames such as a moving image, a result of a frame determined to have a result with low accuracy may be corrected in consideration of results of object recognition or segmentation of preceding and subsequent frames. At this time, a corrected result may be additionally learned as correct data in accordance with an instruction from an examiner.

In the above-described various exemplary embodiments and modified examples, predetermined image processing can also be applied for each detected region, in the case of detecting a region of a subject's eye using the learned model for object recognition or the learned model for segmentation. For example, a case of detecting at least two regions of a vitreum region, a retina region, and a choroid region will be considered. In this case, when image processing such as contrast adjustment is performed on detected at least two regions, adjustment suitable for the respective regions can be performed by using different image processing parameters. By displaying an image in which adjustment suitable for the respective regions has been performed, an operator can diagnose disease of each region appropriately. The configuration of using image processing parameters different for the respective detected regions may be similarly applied to a region of a subject's eye detected without using, for example, a learned model.

Modified Example 4

On the preview screen in the above-described various exemplary embodiments and modified examples, the above-described learned model may be used every at least one frame of a live moving image. At this time, in a case where a plurality of live moving images of different regions or different types is displayed on the preview screen, a learned model corresponding to each live moving image may be used. With this configuration, f a processing time can be shortened even for, for example, a live moving image, an examiner can thereby obtain highly accurate information before the start of image capturing. For example, a failure in rephotograph can be reduced, the accuracy and efficiency of diagnosis can thus be enhanced.

The plurality of live moving images may be, for example, moving images of an anterior eye segment for alignment in XYZ directions, or front moving images of a fundus for focus adjustment of a fundus observation optical system or an OCT focus adjustment. The plurality of live moving images may also be, for example, tomographic moving images of a fundus for coherence gate adjustment of OCT (adjustment of optical path length difference between measurement optical path length and reference optical path length). At this time, the above-described various types of adjustment may be performed in such a manner that a region detected using the above-described learned model for object recognition or the learned model for segmentation satisfies a predetermined condition. For example, various types of adjustment such as OCT focus adjustment may be performed such that a value (e.g., contrast value or intensity value) related to a predetermined retinal layer, such as a vitreum region or a retinal pigment epithelium (RPE), detected using the learned model for object recognition or the learned model for segmentation exceeds a threshold value (or reaches peak value). For example, coherence gate adjustment of OCT may be performed such that a predetermined retinal layer, such as a vitreum region or an RPE detected using the learned model for object recognition or the learned model for segmentation, is located at a predetermined position in the depth direction.

In these cases, the image quality improvement unit (not illustrated) in the image processing apparatus 101 (or the image processing unit 101-04) can generate a high quality moving image by performing image quality improvement processing on a moving image using a learned model. The imaging control unit 101-03 can perform drive control of an optical member, such as the reference mirror 221, that changes an image capturing range such that any of different regions identified by segmentation processing is located at a predetermined position in a display region, in a state in which a high quality moving image is displayed. In such a case, the imaging control unit 101-03 can automatically perform alignment processing such that a desired region is located at a predetermined position of a display region, based on highly-accurate information. The optical member that changes an image capturing range may be, for example, an optical member that adjusts a coherence gate position. Specifically, the optical member may be, for example, the reference mirror 221. The coherence gate position can be adjusted by an optical member that changes an optical path length difference between a measurement optical path length and a reference optical path length. The optical member may be, for example, a mirror (not illustrated) for changing an optical path length of measurement light. The optical member that changes an image capturing range may be, for example, the stage unit 100-2.

A moving image to which the above-described learned model can be applied is not limited to a live moving image. The moving image may be, for example, a moving image stored in the storage unit 101-02. At this time, for example, a moving image obtained by performing position alignment every at least one frame of a tomographic moving image of a fundus that is stored in the storage unit 101-02 may be displayed on a display screen. For example, in a case where a vitreum region is desired to be preferably observed, a reference frame that is based on a condition, such as a vitreum region existing on a frame as far as possible, may be selected. At this time, each frame is a tomographic image (B scan image) in XZ directions. Then, a moving image obtained by performing position alignment of another frame in the XZ directions with respect to the selected reference frame may be displayed on display screen. At this time, for example, high quality images (high quality frames) sequentially generated by the learned model for image quality improvement every at least one frame of a moving image may be consecutively displayed.

As a method of the above-described position alignment between frames, the same method may be applied to a method of position alignment in the X direction and a method of position alignment in the Z direction (depth direction), or different methods may be applied to all position alignment. Position alignment in the same direction may be performed a plurality of times using different methods. For example, after rough position alignment is performed, precise position alignment may be performed. Methods of position alignment include, for example, (rough) position alignment (in the Z direction) that uses a retinal layer boundary obtained by performing segmentation processing on a tomographic image (B scan image), (precise) position alignment (in the X direction or Z direction) that uses correlation information (similarity) between a reference image and a plurality of regions obtained by dividing a tomographic image, position alignment (in the X direction) that uses a one-dimensional projection image generated for each tomographic image (B scan image), and position alignment (in the X direction) that uses a two-dimensional front image. In addition, precise position alignment may be performed for each sub pixel after position alignment is roughly performed for each pixel.

During various types of adjustment, there is a possibility that an image of an image capturing target, such as a retina of a subject's eye, has not been successfully captured yet. There is thereby a possibility that a high quality image cannot be accurately obtained because a difference between a medical image input to a learned model and a medical image used as learning data is large. In view of the foregoing, if an evaluation value of image quality evaluation of a tomographic image (B scan) exceeds a threshold value, the display of a high quality moving image (continuous display of high quality frames) may be automatically started. If an evaluation value of image quality evaluation of a tomographic image (B scan) exceeds a threshold value, a state may be changed to a state (active state) in which an examiner can designate an image quality improvement button. The image quality improvement button is a button for designating the execution of image quality improvement processing. The image quality improvement button may be a button for designating the display of high quality images.

A learned model for image quality improvement different for each of image capturing modes having different scanning patterns may be prepared, and a learned model for image quality improvement corresponding to the selected image capturing mode may be selected. One learned model for image quality improvement obtained by performing learning of learning data including various medical images obtained in different image capturing modes may be used.

Modified Example 5

In the above-described various exemplary embodiments and modified examples, it may be difficult to perform output (estimation/prediction) using a learned model currently performing additional learning in a case where the learned model is performing additional learning. It is thus desirable to prohibit input of a medical image to a learned model currently performing additional learning. Another learned model being the same as a learned model currently performing additional learning may be prepared as an auxiliary learned model. At this time, it is desirable that the input of a medical image to the auxiliary learned model is made executable during additional learning. After additional learning is completed, the learned model having been subjected to additional learning is evaluated, and if the learned model bears no problem, the auxiliary learned model can be replaced with the learned model having been subjected to additional learning. If the learned model bears any problem, the auxiliary learned model may be used. For the evaluation of a learned model, for example, a learned model for classification for separating a high quality image obtained by the learned model for image quality improvement, from images of other types may be used. The learned model for classification may be, for example, a learned model obtained by learning using learning data including a plurality of images including a high quality image and a low quality image obtained by the learned model for image quality improvement as input data, and data labeled (annotated) with the types of these images, as correct data. At this time, the types of images of input data at the time of estimation (at the time of prediction) may be displayed together with information indicating a likelihood for each type of an image included in correct data at the time of learning (e.g., a numerical value indicating a percentage). Input data of the learned model for classification may include, aside from the above-described image, a high quality image on which contrast improvement or noise reduction is performed by overlay processing of a plurality of low quality images (e.g., averaging processing of a plurality of low quality images obtained by performing position alignment).

A learned model obtained by performing learning for each image capturing region may be selectively used. Specifically, a selection unit (not illustrated) that selects any of a plurality of learned models including a first learned model obtained using learning data including a first image capturing region (e.g., lung, subject's eye), and a second learned model obtained using learning data including a second image capturing region different from the first image capturing region may be included. At this time, the image processing unit 101-04 may include a control unit (not illustrated) that executes additional learning of a selected learned model. The control unit can search for data including a pair of an image capturing region corresponding to the selected learned model, and a captured image of the image capturing region in accordance with an instruction from an operator, and execute learning that uses data obtained by the search, as learning data, for the selected learned model as additional learning. The image capturing region corresponding to the selected learned model may be acquired from information regarding a header of the data, or manually input by an examiner. In addition, the search for the data may be performed via a network from a server of an external facility such as a hospital or a research station. With this configuration, additional learning can be efficiently performed for each image capturing region using a captured image of an image capturing region corresponding to a learned model.

The selection unit and the control unit may include a software module executed by a processor such as a CPU or a micro processing unit (MPU) of the image processing unit 101-04. The selection unit and the control unit may be formed by a circuit or an independent apparatus that has a specific function of an ASIC.

When learning data for additional learning is acquired via a network from a server of an external facility such as a hospital or a research station, it is desirable to reduce a decline in reliability that is caused by tampering or a system trouble in additional learning. In view of the foregoing, validity of learning data for additional learning may be detected by checking consistency by using digital signature or hashing. The learning data for additional learning can be thereby protected. At this time, in a case where validity of the learning data for additional learning cannot be detected as a result of the consistency check performed by digital signature or hashing, a warning indicating the detection result, and additional learning using the learning data is not performed. The installation location of the server is not limited, and the type of the server may be any one of, for example, a cloud server, a fog server, and an edge server.

Modified Example 6

In the above-described various exemplary embodiments and modified examples, an instruction from an examiner may be an instruction issued by voice, aside from a manually-issued instruction (e.g., instruction issued using a user interface). In this case, a machine learning engine including, for example, a speech recognition engine (speech recognition model, learned model for speech recognition) obtained by machine learning may be used. In addition, the manually-issued instruction may be an instruction issued by inputting characters using, for example, a keyboard or a touch panel. At this time, a machine learning engine including, for example, a character recognition engine (character recognition model, learned model for character recognition) obtained by machine learning may be used. The instruction from the examiner may be an instruction issued by gesture. In this case, a machine learning engine including a gesture recognition engine (gesture recognition model, learned model for gesture recognition) obtained by machine learning may be used.

The instruction from the examiner may be an eye-gaze detection result of the examiner on a display screen on the display unit 104. The eye-gaze detection result may be a pupil detection result that uses a moving image of the examiner obtained by performing image capturing from the periphery of the display screen on the display unit 104, for example. In this case, the above-described object recognition engine may be used for pupil detection from the moving image. The instruction from the examiner may be an instruction issued by, for example, brain waves or a weak electrical signal flowing in a body.

In such a case, the learning data may be learning data in which character data or voice data (waveform data) indicating an instruction to display a result obtained by processing of the above-described various learned models is set as input data, and an execution command for displaying a result obtained by processing of various learned models, on the display unit 104 is set as correct data. The learning data may be, for example, learning data in which character data or voice data indicating an instruction to display a high quality image obtained by the learned model for image quality improvement is set as input data, and an execution command of the display of the high quality image and an execution command for changing an image quality improvement button to an active state are set as correct data. The learning data may be any learning data as long as content of the instruction indicated by the character data or voice data and content of the execution command correspond to each other, for example. Voice data may be converted into character data using an acoustic model or a language model. Processing of reducing noise data superimposed on voice data may be performed using waveform data obtained by a plurality of microphones. An instruction issued by characters or voice, and an instruction issued using a mouse or a touch panel may be made selectable in accordance with an instruction from an examiner. In addition, on/off of an instruction issued by characters or voice may be made selectable in accordance with an instruction from the examiner.

The machine learning includes the above-described deep learning, and for example, a recurrent neural network (RNN) can be used in at least one layer of the multi-hierarchical neural network. As an example of a machine learning model according to this modified example, an RNN being a neural network that handles time-series information will be described with reference to FIGS. 9A and 9B. In addition, a long short-term memory (hereinafter, LSTM), which is one type of the RNN, will be described with reference to FIGS. 10A and 10B.

Figure 9A:
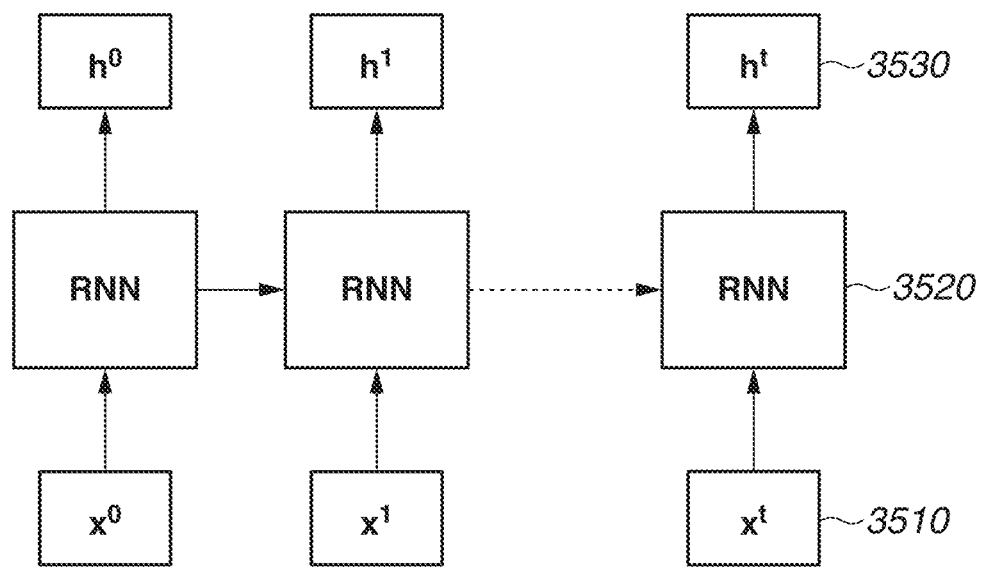
FIG. 9A illustrates an example of a configuration of a neural network used as a machine learning engine according to Modified Example 6.
Figure 9B:
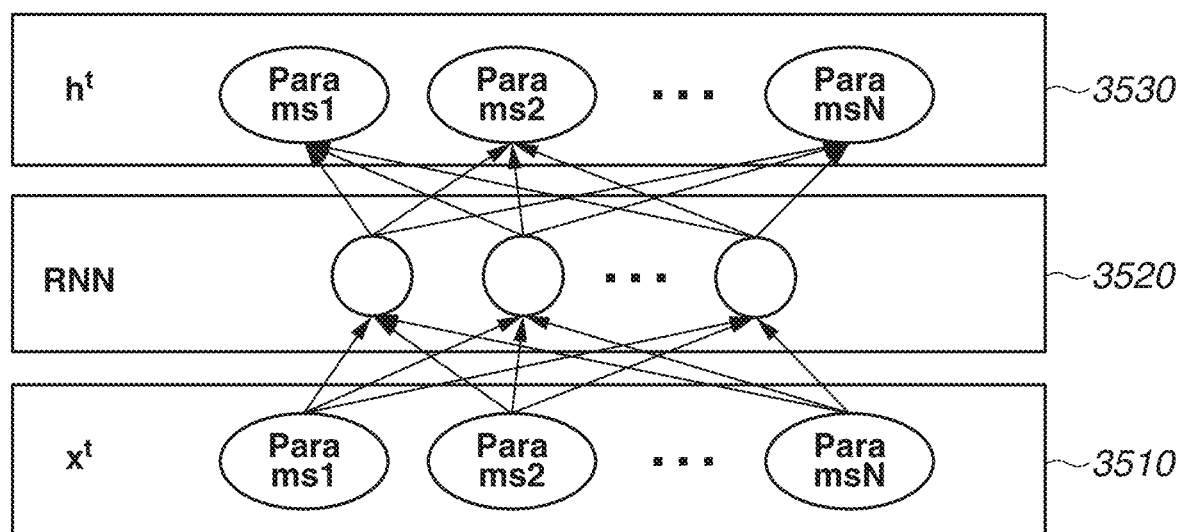
FIG. 9B illustrates an example of a configuration of a neural network used as a machine learning engine according to Modified Example 6.

FIG. 9A illustrates a structure of an RNN being a machine learning model. An RNN 3520 has a loop structure in a network, and at a time t, inputs data $x^t$ 3510 and outputs data $h^t$ 3530. The RNN 3520 has a loop structure in a network, and thereby a state at the current time can be taken over to the next state. Thus, time-series information can be handled. FIG. 9B illustrates an example of input-output of a parameter vector at the time t. The data $x^t$ 3510 includes N (Params1 to ParamsN) pieces of data. The data $h^t$ 3530 output by the RNN 3520 includes N (Params1 to ParamsN) pieces of data corresponding to the input data.

Figure 10A:
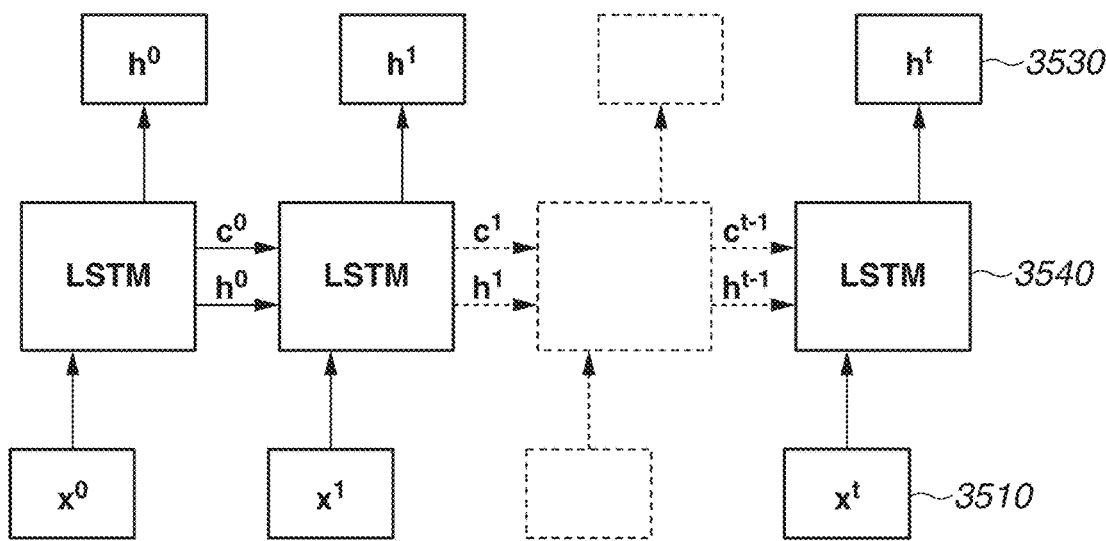
FIG. 10A illustrates an example of a configuration of a neural network used as a machine learning engine according to Modified Example 6.

Nevertheless, long-term information cannot be handled in an RNN at the time of backpropagation, and thereby the LSTM is sometimes used. The LSTM can learn long-term information by including a forget gate, an input gate, and an output gate. FIG. 10A illustrates a structure of the LSTM. In an LSTM 3540, information to be taken over to the next time t by a network includes an internal state $c^{t-1}$ of the network called a cell, and output data $h^{t-1}$. Lower-case characters (c, h, x) illustrated in FIG. 10A indicate vectors.

Figure 10B:
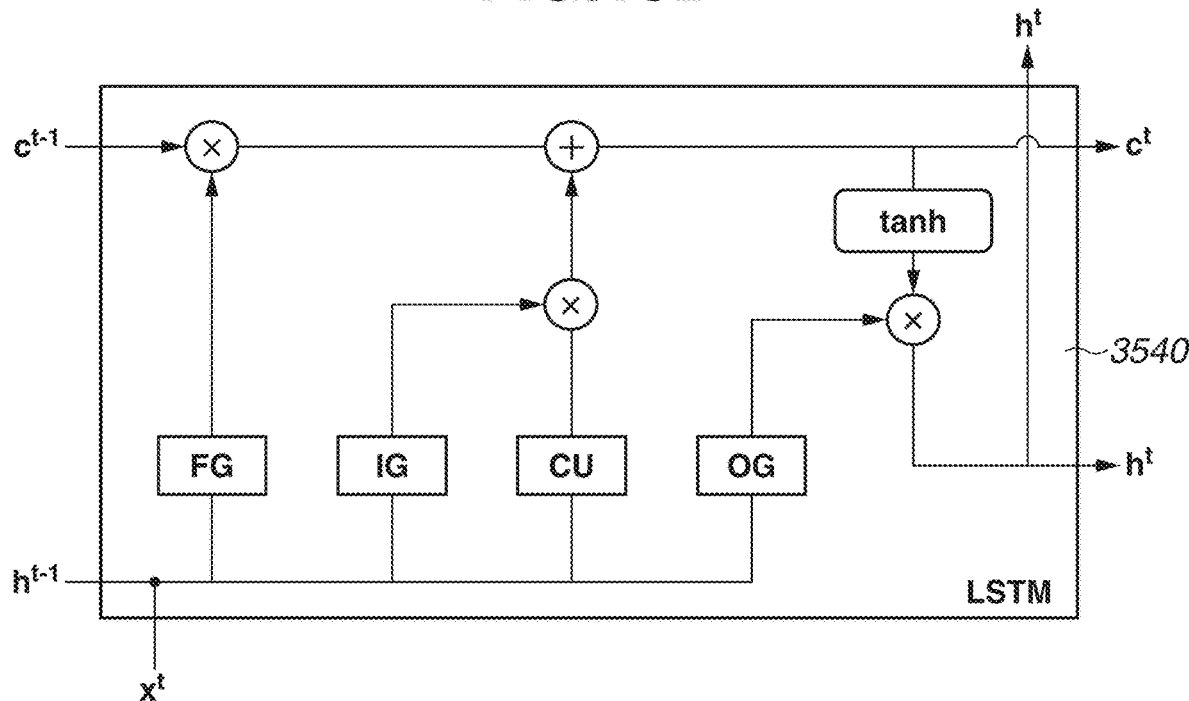
FIG. 10B illustrates an example of a configuration of a neural network used as a machine learning engine according to Modified Example 6.

FIG. 10B illustrates the details of the LSTM 3540. In FIG. 10B, the LSTM 3540 includes a forget gate network FG, an input gate network IG, and an output gate network OG, and each of these is a sigmoid layer. Thus, each element outputs a vector having a value ranging from 0 to 1. The forget gate network FG determines an amount of past information to be held, and the input gate network IG determines a value to be updated. A cell update candidate network CU is an activation function tan h layer. This creates a vector of a new candidate value to be added to a cell. The output gate network OG selects an element of cell candidates and selects an amount of information to be conveyed to the next time.

The model of the above-described LSTM has a basic form, and thus the network is not limited to the networks illustrated here. For example, connection between networks may be changed. A quasi recurrent neural network (QRNN) may be used in place of the LSTM. Furthermore, a machine learning model is not limited to a neural network, and boosting or a support vector machine may be used. In a case where an instruction from an examiner is an input performed by characters or voice, a technique (e.g., Sequence to Sequence) related to natural language processing may be applied. A dialogue engine (dialogue model, learned model for dialogue) that responds to the examiner by an output using characters or voice may be applied.

Modified Example 7

In the above-described various exemplary embodiments and modified examples, a high quality image may be stored into the storage unit 101-02 in accordance with an instruction from an examiner. In this case, after an instruction from an examiner for storing a high quality image, in registering a file name, a file name including information (e.g., characters) indicating that a displayed image is an image generated by processing (image quality improvement processing) that uses the learned model for image quality improvement, at any portion (e.g., foremost portion or rearmost portion) of the file name may be displayed in accordance with an instruction from the examiner as a recommended file name in an editable state.

On various display screens such as a report screen, a display indicating that the displayed image is a high quality image generated by processing that uses the learned model for image quality improvement may be displayed together with the high quality image, when a high quality image is displayed on the display unit 104. In this case, an examiner can easily identify, based on the display, that the displayed high quality image is not an image acquired by image capturing, it is therefore possible to reduce wrong diagnosis or enhance diagnosis efficiency. The display indicating that the displayed image is a high quality image generated by processing that uses the learned model for image quality improvement may take any form as long as the display makes an input image and the high quality image generated by the processing distinguishable. As for processing that uses the above-described various learned models as well as the processing that uses the learned model for image quality improvement, a display indicating that a displayed result is a result generated by processing that uses a learned model of the type may be displayed together with the result.

At this time, a display screen such as a report screen may be stored into the storage unit 101-02 as image data in accordance with an instruction from the examiner. For example, the report screen may be stored into the storage unit 101-02 as one image in which image quality improved images and a display indicating that these images are high quality images generated by processing that uses the learned model for image quality improvement are arranged.

As to a display indicating that the displayed image is a high quality image generated by processing that uses the learned model for image quality improvement, a display indicating the type of learning data used for learning by the learned model for image quality improvement may be displayed on the display unit 104. The display may include, for example, explanation of types of input data and correct data of learning data, and an arbitrary display regarding correct data such as an image capturing region included in input data and correct data. As for processing that uses the above-described various learned models as well as the processing that uses the learned model for image quality improvement, a display indicating a type of learning data used for learning by a learned model of the type may be displayed on the display unit 104.

Information (e.g., characters) indicating that the displayed image is an image generated by processing that uses the learned model for image quality improvement may be displayed or stored with being superimposed on, for example, a high quality image. In this case, the point at which the information is superimposed may be any point on the image as long as a region (e.g., edge of image) does not overlap a region in which a target region serving as an image capturing target is displayed. A region not overlapping is determined, and the information may be superimposed on the determined region.

In a case where an active state (image quality improvement processing is turned on) of the image quality improvement button is set by default on a default display screen of a report screen, a report image corresponding to a report screen including a high quality image may be sent to a server, such as the external storage unit 102, in accordance with an instruction from an examiner. In a case where the active state of the image quality improvement button is set by default, a report image corresponding to a report screen including a high quality image may be (automatically) sent to a server, at the time of an inspection end (e.g., when a display screen is changed to the report screen from the image capturing confirmation screen or the preview screen in accordance with an instruction from the examiner). At this time, a report image generated based on various settings in a default setting may be sent to a server. The various settings relate to at least one of a depth range for generating an En-Face image on a default display screen of a report screen, presence or absence of superimposition of an analysis map, whether the image is a high quality image, and whether the screen is the display screen for follow-up.

Modified Example 8

In the above-described various exemplary embodiments and modified examples, an image (e.g., a high quality image, an image indicating an analysis result such as an analysis map, an image indicating an object recognition result, and an image indicating a segmentation result) obtained by a learned model of a first type, among the above-described various learned models, may be input to a learned model of a second type different from the first type. At this time, a result (e.g., an analysis result, a diagnosis result, an object recognition result, and a segmentation result) obtained by processing of the learned model of the second type may be generated.

An image to be input to the learned model of the second type different from the first type may be generated from an image input to the learned model of the first type, by using a result (e.g., an analysis result, a diagnosis result, an object recognition result, a segmentation result) obtained by processing of the learned model of the first type among the above-described various learned models. At this time, the generated image is highly likely to be an image suitable as an image to be processed by the learned model of the second type. Thus, it is possible to improve the accuracy of an image (e.g., a high quality image, an image indicating an analysis result such as an analysis map, an image indicating an object recognition result, and an image indicating a segmentation result) obtained by inputting the generated image to the learned model of the second type.

In addition, the above-described various learned models may be a learned model obtained by learning using learning data including a two-dimensional medical image of a subject, or may be a learned model obtained by learning using learning data including a three-dimensional medical image of a subject.

In addition, similar case image search that uses an external database stored in a server may be performed using an analysis result or a diagnosis result obtained by the processing of the above-described learned model, as a search key. In a case where a plurality of images stored in the database is managed in a state where respective feature amounts of the plurality of images are already attached as accompanying information by machine learning, a similar case image search engine (similar case image search model, learned model for similar case image search) that uses an image itself as a search key may be used. For example, the image processing unit 101-04 (different from the learned model for image quality improvement) can search at least one medical image of a plurality of medical images to be subjected to blend processing, for a similar case image related to the at least one medical image, using the learned model for similar case image search. The display control unit 101-05 can display, for example, a similar case image obtained from the above-described at least one medical image using the learned model for similar case image search, on the display unit 104.

Modified Example 9

Generation processing of motion contrast data in the above-described various exemplary embodiments and modified examples is not limited to a configuration of being performed based on a brightness value of a tomographic image. The above-described various types of processing may be applied to an interference signal acquired by the tomographic image capturing apparatus 100, a signal obtained by performing Fourier transform on the interference signal, a signal obtained by performing arbitrary processing on the signal, and tomographic data including tomographic images based on these signals. Also in these cases, an effect similar to the above-described configuration can be obtained. For example, a fiber optical system that uses an optical coupler as a division unit is used, but a space optical system that uses a collimator and a beam splitter may be used. The configuration of the tomographic image capturing apparatus 100 is not limited to the above-described configuration, and a part of configurations included in the tomographic image capturing apparatus 100 may be made a configuration separated from the tomographic image capturing apparatus 100. In the above-described configuration, the Michelson interferometer is used as an interference optical system of the tomographic image capturing apparatus 100, but the configuration of the interference optical system is not limited to this. For example, the interference optical system of the tomographic image capturing apparatus 100 may include, for example, the Mach-Zehnder interferometer. A spectral domain OCT (SD-OCT) apparatus that uses an SLD as a light source has been described as an OCT apparatus, but the configuration of the OCT apparatus is not limited to this. For example, the present invention can also be applied to any type of an OCT apparatus, such as a swept source OCT (SS-OCT) apparatus that uses a wavelength swept light source and can sweep wavelength of emitted light. The present invention can also be applied to a Line-OCT apparatus (or SS-Line-OCT apparatus) that uses line light. The present invention can also be applied to a Full Field-OCT apparatus (or SS-Full Field-OCT apparatus) that uses area light. The image processing unit 101-04 acquires an interference signal acquired by the tomographic image capturing apparatus 100 and a three-dimensional tomographic image generated by the image processing unit 101-04, but a configuration in which the image processing unit 101-04 acquires such signals and images is not limited to this. For example, the image processing unit 101-04 may acquire these signals from a server or an image capturing apparatus connected via, for example, a local area network (LAN), a wide area network (WAN), or the Internet.

The learned model can be provided in the image processing unit 101-04. The learned model can be formed by a software module executed by a processor such as a CPU. The learned model may be provided in another server connected with the image processing unit 101-04. In this case, the image processing unit 101-04 can perform image quality improvement processing using a learned model by connecting to a server including a learned model, via any network such as the Internet.

During a process of generating motion contrast data, the image quality improvement engine can be appropriately applied. For example, the image quality of a tomographic image before a decorrelation value is obtained may be preliminarily improved by using the image quality improvement engine prepared for tomographic images. In a case where an NOR is three or more, at least two pieces of motion contrast data can be generated, and image quality can also be improved by averaging a plurality of pieces of motion contrast data. In this case, image quality of each piece of motion contrast data before averaging processing may be preliminarily improved by the image quality improvement engine. Alternatively, the image quality improvement engine may be applied to motion contrast data having been subjected to averaging. Image quality of volume data may be improved by the image quality improvement engine for three-dimensional data that is preliminarily formed by known 3D-UNet, by using volume data (three-dimensional motion contrast data) as motion contrast data. Moreover, in a case where an NOR is three or more, at least two pieces of three-dimensional motion contrast data can be generated, and final volume data may be obtained by averaging these. In this case, the image quality improvement engine may be applied to at least one of volume data not having been subjected to averaging and volume data having been subjected to averaging processing. Furthermore, after OCTA front images are respectively generated from a plurality of pieces of volume data, averaging processing can be performed on the OCTA front images. Similarly, the image quality improvement engine can be applied to at least one of an OCTA front image not having been subjected to averaging and an OCTA front image having been subjected to averaging processing. In this manner, when an OCTA front image is generated from motion contrast data, various modifications can be made especially in a case where an NOR is three or more, and the image quality improvement engine may be applied to any data irrespective of whether data is two-dimensional data or three-dimensional data.

Modified Example 10

Images to be processed by the image processing apparatus 101 or the image processing method according to the above-described various exemplary embodiments and modified examples include a medical image acquired using an arbitrary modality (image capturing apparatus, image capturing method). A medical image to be processed can include a medical image acquired by an arbitrary image capturing apparatus, and an image created by the image processing apparatus 101 or the image processing method according to the above-described exemplary embodiments and modified examples.

A medical image to be processed is an image of a predetermined region of a subject, and the image of the predetermined region includes at least part of the predetermined region of the subject. In addition, the medical image may include another region of the subject. The medical image may be a still image or a moving image, and may be a monochrome image or a color image. Furthermore, the medical image may be an image representing a structure (configuration) of the predetermined region, or may be an image representing a function thereof. An image representing a function includes an image representing a blood flow moving state (e.g., blood flow amount, and blood flow speed) such as an OCTA image, a Doppler OCT image, a functional magnetic resonance imaging (fMRI) image, and an ultrasonic Doppler image. The predetermined region of the subject may be determined in accordance with an image capturing target, and includes an organ, such as a human eye (subject's eye), brain, lung, intestine, heart, pancreas, kidney, and liver, and an arbitrary region, such as a head portion, a breast portion, a leg portion, and an arm portion.

The medical image may be a tomographic image of a subject, or may be a front image. The front image includes, for example, a fundus front image, a front image of an anterior eye segment a fundus image obtained by fluorescein image capturing, and an En-Face image generated using data in at least partial range in the depth direction of an image capturing target for data (three-dimensional OCT data)

acquired by OCT. The En-Face image may be an En-Face image of OCTA (motion contrast front image) generated using data in at least partial range in the depth direction of an image capturing target for three-dimensional OCTA data (three-dimensional motion contrast data). The three-dimensional OCT data and the three-dimensional motion contrast data are examples of three-dimensional medical image data.

The motion contrast data is data indicating a change between a plurality pieces of volume data obtained by controlling the same region (same position) of a subject's eye to be scanned with measurement light a plurality of times. At this time, volume data includes a plurality of tomographic images obtained at different positions. By obtaining data indicating a change between a plurality of tomographic images obtained at substantially the same position at each of the different positions, motion contrast data can be obtained as volume data. A motion contrast front image is also referred to as an OCTA front image (En-Face image of OCTA) related to OCT angiography (OCTA) for measuring a motion of a blood flow, and motion contrast data is also referred to as OCTA data. The motion contrast data can be obtained as, for example, a decorrelation value of two tomographic images or interference signals corresponding to the two tomographic images, a dispersion value, or a value obtained by dividing a maximum value by a minimum value (maximum value/minimum value), and the motion contrast data may be obtained by a known arbitrary method. At this time, two tomographic images can be obtained by, for example, controlling the same region (same position) of a subject's eye to be scanned with measurement light a plurality of times.

An En-Face image is a front image generated by, for example, projecting data of a range between two layer boundaries in XY directions. At this time, the front image is generated by projecting or integrating, on a two-dimensional plane, data corresponding to a depth range defined based on two reference surfaces, the depth range being at least part of volume data (three-dimensional tomographic image) obtained using optical interference. The En-Face image is a front image generated by projecting data of volume data that corresponds to a depth range determined based on a detected retinal layer, on a two-dimensional plane. As a method of projecting data corresponding to a depth range defined based on two reference surfaces, on a two-dimensional plane, for example, a method of setting a representative value of data within the depth range to a pixel value on the two-dimensional plane can be used. The representative value can include values such as an average value, a median value, or a maximum value of pixel values within the range in the depth direction of a region surrounded by the two reference surfaces. The depth range related to an En-Face image may be, for example, a range including a predetermined number of pixels in a deeper direction or a shallower direction based on one of the two layer boundaries related to the detected retinal layer. The depth range related to an En-Face image may be, for example, a range changed (offset) in accordance with an instruction of an operator from the range between the two layer boundaries related to the detected retinal layer.

An image capturing apparatus is an apparatus for capturing an image to be used for diagnosis. The image capturing apparatus includes, for example, an apparatus that obtains an image of a predetermined region by emitting light, radioactive rays such as X-rays, electromagnetic waves, or ultrasonic waves to a predetermined region of a subject, and an apparatus that obtains an image of a predetermined region by detecting radioactive rays emitted from a subject. More specifically, the image capturing apparatus according to the above-described various exemplary embodiments and modified examples at least includes an X-ray image capturing apparatus, a CT apparatus, an MRI apparatus, a PET apparatus, an SPECT apparatus, an SLO apparatus, an OCT apparatus, an OCTA apparatus, a fundus camera, and an endoscope.

The OCT apparatus may include a time domain OCT (TD-OCT) apparatus and a Fourier domain OCT (FD-OCT) apparatus. The Fourier domain OCT apparatus may include a spectral domain OCT (SD-OCT) apparatus and a swept source OCT (SS-OCT) apparatus. As an SLO apparatus and an OCT apparatus, an adaptive optics SLO (AO-SLO) apparatus and an adaptive optics OCT (AO-OCT) apparatus that use an adaptive optics optical system may be included. As an SLO apparatus and an OCT apparatus, a polarization-sensitive SLO (PS-SLO) apparatus and a polarization-sensitive OCT (PS-OCT) apparatus for visualizing a polarization phase difference and information regarding depolarization may be included.

Other Exemplary Embodiments

The present invention can also be implemented by executing the following processing. More specifically, the processing is processing of supplying software (program) for implementing one or more functions of the above-described various exemplary embodiments and modified examples, to a system or an apparatus via a network or various storage media, and a computer (or CPU, MPU. etc.) of the system or the apparatus reading and executing the program.

The present invention can also be implemented by processing of supplying software (program) for implementing one or more functions of the above-described various exemplary embodiments and modified examples, to a system or an apparatus via a network or a storage medium, and a computer of the system or the apparatus reading and executing the program. The computer includes one or a plurality of processors or circuits, and includes a network of a plurality of separated computers or a plurality of separated processors or circuits for reading and executing a computer executable command.

At this time, the processors or circuits can include a central processing unit (CPU), a micro processing unit (MPU), a graphics processing unit (GPU), an application specific integrated circuit (ASIC), or a field programmable gate array (FPGA). The processors or circuits can include a digital signal processor (DSP), a data flow processor (DFP), or a neural processing unit (NPU).

The present invention is not limited to the above-described exemplary embodiments, and various changes and modifications can be made without departing from the spirit and scope of the present invention. The following claims are therefore appended for setting forth the scope of the present invention.

According to an aspect of the present invention, a region of interest serving as a target of analysis processing can be made desirably settable.

OTHER EMBODIMENTS

Embodiment(s) of the present invention can also be realized by a computer of a system or apparatus that reads out and executes computer executable instructions (e.g., one or more programs) recorded on a storage medium (which may also be referred to more fully as a 'non-transitory computer-readable storage medium') to perform the functions of one or more of the above-described embodiment(s)

and/or that includes one or more circuits (e.g., application specific integrated circuit (ASIC)) for performing the functions of one or more of the above-described embodiment(s), and by a method performed by the computer of the system or apparatus by, for example, reading out and executing the computer executable instructions from the storage medium to perform the functions of one or more of the above-described embodiment(s) and/or controlling the one or more circuits to perform the functions of one or more of the above-described embodiment(s). The computer may comprise one or more processors (e.g., central processing unit (CPU), micro processing unit (MPU)) and may include a network of separate computers or separate processors to read out and execute the computer executable instructions. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

The invention claimed is:

1. An image processing apparatus comprising:
   one or more processors connected to one or more memories storing instructions executable by the one or more processors, wherein the one or more processors connected to the one or more memories are configured to function as:
   an obtaining unit configured to obtain an optical coherence tomography (OCT) image and an OCT angiography (OCTA) image of mutually corresponding regions in a subject that are acquired by an optical interferometer;
   a blend processing unit configured to generate a blend image obtained by performing blend processing at a transmissivity changeable in response to an instruction from an operator using the obtained OCT image and an OCTA image of high image quality obtained by inputting the obtained OCTA image as input data of a learned model for image quality improvement obtained by learning an OCTA image of the subject;
   a display control unit configured to control the display unit to display the generated blend image on the display unit; and
   a selection unit configured to select a type of analysis processing to be performed on the OCTA image of high image quality;
   wherein the display control unit controls the display unit to display a result of the selected type of the analysis processing on a region of interest in the OCTA image of high image quality set in response to an instruction from the operator in the displayed blend image.

2. The image processing apparatus according to claim 1, wherein at least either one image of the OCT image and the OCTA image has an attribute indicating two or more classifications, for each pixel, the attribute being set based on whether the pixel value exceeds a threshold value,
   wherein the blend processing unit generates a blend image based on the attribute and the predetermined transmissivity, and
   wherein the image having the attribute has an attribute of being classified based on a pixel value of the image.

3. The image processing apparatus according to claim 1, wherein at least either one image of the OCT image and the OCTA image has an attribute indicating two or more classifications, for each pixel,
   wherein the blend processing unit generates a blend image based on the attribute and the predetermined transmissivity, and
   wherein the image having the attribute has an attribute set in accordance with a preset partial region of the image.

4. The image processing apparatus according to claim 2, wherein, in a case where the image having the attribute is an OCTA image, the attribute is an attribute that is based on a likelihood of a pixel being a blood vessel.

5. The image processing apparatus according to claim 2, wherein, in a case where the attribute is an attribute indicating predetermined classification, the blend processing unit fixes the transmissivity corresponding to the pixel of the image having the attribute, to 0 or 1.

6. An image processing apparatus comprising:
   one or more processors connected to one or more memories storing instructions executable by the one or more processors, wherein the one or more processors connected to the one or more memories are configured to function as:
   an obtaining unit configured to obtain an optical coherence tomography (OCT) image and an OCT angiography (OCTA) image of mutually corresponding regions in a subject that are acquired by an optical interferometer; and
   a display control unit configured to control a display unit to display, on the display unit, a blend image obtained by performing blend processing at a variable transmissivity in accordance with an instruction from an operator using the obtained OCT image and an OCTA image of high image quality obtained by inputting the obtained OCTA image as input data of a learned model for image quality improvement obtained by learning an OCTA image of the subject.

7. The image processing apparatus according to claim 6, wherein the display control unit controls the display unit to display a result of analysis processing of a set region of interest.

8. The image processing apparatus according to claim 6, wherein a new transmissivity is set from at least one image of the OCT image and the OCTA image using a learned model obtained by performing learning using learning data in which a medical image is set as input data and a transmissivity to be used in the blend processing is set as correct data.

9. The image processing apparatus according to claim 6, wherein the blend processing is executed by performing weighted average processing on pixel values of mutually corresponding positions of the OCT image and the OCTA image.

10. The image processing apparatus according to claim 6, wherein the display control unit displays, on the display unit, at least one of (a) an image analysis result obtained from the at least one medical image using a learned model different from the learned model for image quality improvement, (b) a diagnosis result obtained from the at least one medical image using a learned model different from the learned model for image quality improvement, (c) information regarding a difference between a medical image obtained from the at least one medical image using a generative adversarial network or an auto-encoder and the at least one medical image, as information regarding an abnormal region, (d) a similar case image obtained from the at least one medical image using a learned model different from the learned model for image quality improvement, and (e) an object detection result or a segmentation result that is obtained from the at least one medical image using a learned model different from the learned model for image quality improvement.

11. The image processing apparatus according to claim 6, wherein the display control unit displays, on the display unit, an image, information, or a result that is obtained by inputting the plurality of medical images to a learned model.

12. The image processing apparatus according to claim 6, wherein an instruction of an operator regarding a change of the transmissivity is information obtained using at least one learned model of a learned model for character recognition, a learned model for speech recognition, and a learned model for gesture recognition.

13. The image processing apparatus according to claim 6, wherein the display control unit controls the display unit to display a result of the selected type of the analysis processing on a region of interest in the OCTA image of high image quality set in response to an instruction from the operator in the displayed blend image.

14. The image processing apparatus according to claim 13, wherein the display control unit controls the display unit to change display of the result of the analysis processing to display of a result of the selected type of analysis processing on the region of interest set in the obtained OCTA image in a case where an instruction from the operator regarding change from the OCTA image of high image quality to the obtained OCTA image.

15. The image processing apparatus according to claim 13, wherein the display control unit controls the display unit to change display of the result of the analysis processing to display of a result of another type of analysis processing selected in accordance with an instruction from the operator.

16. The image processing apparatus according to claim 6, wherein, in a case where an instruction from the operator regarding change from one of a display screen of the blend image and the display screen of a plurality of OCTA images including the obtained OCTA image to other is received, the display control unit controls the display unit to maintain a display state of the OCTA image of high image quality in a case of the display state of the OCTA image of high image quality and maintains a display state of the obtained OCTA image in a case of the display state of the obtained OCTA image.

17. The image processing apparatus according to claim 6, wherein the display control unit controls the display unit to display information for receiving an instruction from the operator regarding change of a depth range of each of the obtained OCT image and the obtained OCTA image and information for receiving an instruction from the operator regarding change of the transmissivity.

18. An image processing apparatus comprising:
one or more processors connected to one or more memories storing instructions executable by the one or more processors, wherein the one or more processors connected to the one or more memories are configured to function as:
a display control unit configured to control a display unit to display, on the display unit, a blend image obtained by performing blend processing at a variable transmissivity in accordance with an instruction of an operator using a first medical image and a second medical image of a type different from the first medical image of mutually corresponding regions in a subject;
a setting unit configured to set a region of interest in the displayed blend image; and
an execution unit configured to execute processing on the set region of interest in at least one image of the first medical image and the second medical image,
wherein the display control unit is configured to control to display, on the display unit, a medical image with higher image quality than at least one medical image of a first medical image and a second medical image, using a learned model for image quality improvement that is obtained by learning a medical image of a subject.

19. An image processing method comprising:
obtaining an OCT image and an OCTA image of mutually corresponding regions in a subject that are acquired by an optical interferometer; and
controlling a display unit to display, on the display unit, a blend image obtained by performing blend processing at a variable transmissivity in accordance with an instruction of an operator using the obtained OCT image and an OCTA image of high image quality obtained by inputting the obtained OCTA image as input data of a learned model for image quality improvement obtained by learning an OCTA image of the subject.

20. An image processing method comprising:
controlling a display unit to display, on the display unit, a blend image obtained by performing blend processing at a variable transmissivity in accordance with an instruction of an operator using a first medical image and a second medical image of a type different from the first medical image of mutually corresponding regions in a subject;
setting a region of interest in the displayed blend image; and
executing processing on the set region of interest in at least one image of the first medical image and the second medical image,
wherein the display unit is controlled to display a medical image with higher image quality than at least one medical image of a first medical image and a second medical image, using a learned model for image quality improvement that is obtained by learning a medical image of a subject.

* * * * *